United States Patent [19]

Gandolfi et al.

[11] 4,242,508
[45] Dec. 30, 1980

[54] CERTAIN THIACYCLIC PGI COMPOUNDS

[75] Inventors: Carmelo Gandolfi, Milan; Carlo Passarotti, Gallarate; Alessandro Andreoni, Cologno Monzese; Angelo Fumagalli, Monza; Franco Faustini, Milan; Roberto Ceserani, Milan; Maria M. Usardi, Milan, all of Italy

[73] Assignee: Farmitalia Carlo Erba S.p.A., Milan, Italy

[21] Appl. No.: 29,921

[22] Filed: Apr. 13, 1979

Related U.S. Application Data

[62] Division of Ser. No. 920,166, Jun. 29, 1978, which is a division of Ser. No. 859,703, Dec. 12, 1977, abandoned.

[30] Foreign Application Priority Data

Dec. 31, 1976 [IT] Italy .............................. 31401 A/76
Jan. 14, 1977 [IT] Italy .............................. 19283 A/77
Mar. 14, 1977 [IT] Italy .............................. 21171 A/77
Mar. 21, 1977 [IT] Italy .............................. 21412 A/77
Mar. 31, 1977 [IT] Italy .............................. 21863 A/77

[51] Int. Cl.³ .................. C07D 333/24; A61K 31/38

[52] U.S. Cl. ................................ 542/430; 542/426; 549/13; 549/28; 549/51; 549/58; 549/49; 549/60

[58] Field of Search ................. 549/49, 60, 51, 58, 549/13, 28; 542/426, 420

[56] References Cited

FOREIGN PATENT DOCUMENTS 1-270   4/1979  European Pat. Off. .
2009148 6/1979  United Kingdom .

Primary Examiner—Henry R. Jiles
Assistant Examiner—Bernard Dentz
Attorney, Agent, or Firm—Murray and Whisenhunt

[57] ABSTRACT

Bicyclic prostaglandins and pharmaceutical and veterinary compositions containing them having numerous pharmaceutical or veterinary utilities including, for example, hypotensive, vasodilatory, antiaggregating, luteolytic, and cytoprotective activities. Processes for preparing the compounds and compositions are also disclosed.

20 Claims, No Drawings

CERTAIN THIACYCLIC PGI COMPOUNDS

This is a divisional application of Ser. No. 920,166, filed June 29, 1978, which is a divisional of Ser. No. 859,703, filed Dec. 12, 1977, now abandoned.

The present invention relates to 2-oxa-bicyclic prostaglandins, to a method for their preparation and to pharmaceutical and veterinary compositions containing them.

The compounds of the invention are 2-oxa-bicyclic prostaglandins of formula (I)

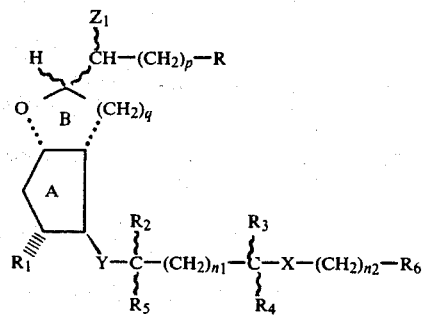

wherein

R is a member selected from the group consisting of
(a) a free or esterified carboxy group; (b)

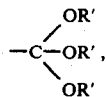

wherein each of the R' groups, which are the same or different, is $C_1$–$C_6$ alkyl or phenyl; (c) —CH$_2$OH; (d)

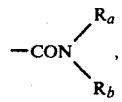

wherein $R_a$ and $R_b$ are independently selected from the group consisting of hydrogen, $C_1$–$C_6$ alkyl, $C_2$–$C_6$ alkanoyl and phenyl; (e) a radical

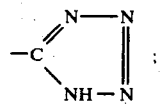

(f) —C≡N;
$Z_1$ is hydrogen or halogen;
p is zero or an integer of 1 to 7;
q is 1 or 2;
$R_1$ is hydrogen, hydroxy, $C_1$–$C_6$ alkoxy, ar-$C_1$–$C_6$-alkoxy, acyloxy;
Y is a member selected from the group consisting of —CH$_2$CH$_2$—; —C≡C—,

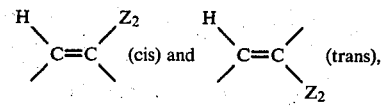

wherein $Z_2$ is hydrogen or halogen; one of $R_2$ and $R_5$ is hydrogen, $C_1$–$C_6$ alkyl, $C_2$–$C_6$ alkenyl, $C_2$–$C_6$ alkynyl or aryl, and the other is hydroxy, $C_1$–$C_6$ alkoxy, ar-$C_1$–$C_6$-alkoxy or $R_2$ and $R_5$, taken together, form an oxo group;

each of $R_3$ and $R_4$, which are the same or different, may be hydrogen, $C_1$–$C_6$alkyl or fluorine or $R_3$ and $R_4$, taken together with the carbon atom to which they are linked, form the radical

or the radical

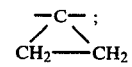

each of $n_1$ and $n_2$, which are the same or different, is zero or an integer of 1 to 6;

X is a member selected from the group consisting of —O—, —S— and —(CH$_2$)$_m$—, wherein m is zero or 1;

$R_6$ is a member selected from the group consisting of
(a') hydrogen;
(b') $C_1$–$C_4$ alkyl;
(c') a $C_3$–$C_9$ cycloaliphatic radical, unsubstituted or substituted by one or more substituents selected from the group consisting of $C_1$–$C_6$ alkyl and $C_1$–$C_6$ alkoxy;
(d') aryl, unsubstituted or substituted by one or more substituents selected from the group consisting of halogen, halo-$C_1$–$C_6$-alkyl, $C_1$–$C_6$ alkyl and $C_1$–$C_6$ alkoxy; and
(e') a saturated or unsaturated heterocyclic ring, unsubstituted or substituted by one or more substituents selected from the group consisting of halogen, halo-$C_1$–$C_6$-alkyl, $C_1$–$C_6$ alkyl and $C_1$–$C_6$ alkoxy.

Also the pharmaceutically or veterinarily acceptable salts as well as the optical antipodes, i.e. the enantiomers, the racemic mixtures of the optical antipodes, the geometric isomers and their mixtures and the mixtures of the diastereoisomers of the compounds of formula (I) are included in the scope of the present invention.

In the formulae of this specification the broken line (⫼⫼⫼⫼) indicates that a substituent bound to the cyclopentane ring is in the α-configuration, i.e. below the plane of the ring, a substituent bound to the 2-oxa-bicyclic system is in the endo-configuration and a substituent bound to a chain is in the S-configuration; the heavy solid line (—) indicates that a substituent bound to the cyclopentane ring is in the β-configuration, i.e. above the plane of the ring, a substituent bound to the 2-oxa-bicyclic system is in the exo-configuration and a substituent bound to a chain is in the R-configuration; the wavy line attachment ( $\}$ ) indicates that a substituent does not possess a definite stereochemical identity i.e. that a substituent bound to the cyclopentane ring may be both in the α- and in the β-configuration, a substituent bound to the 2-oxa-byciclic system may be both in the endo- or in the exo-configuration and a substituent bound to a chain may be both in the S- and in the R-configuration.

In the compounds of the above formula (1) the heterocyclic ring B is cis-fused with the cyclopentane ring A and the two bonds indicated by the dotted lines (...) are both in the α-configuration with respect to the ring A.

The side chain β-linked to the cyclopentane ring A is in trans-configuration with respect to the α-fused heterocyclic ring B and consequently it is an exo substituent with respect to the 2-oxa-bicyclic system.

The carbon atom of the heterocyclic ring B bearing the side chain

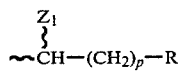

bears also an hydrogen atom.

When the side chain

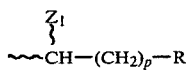

is in the endo-configuration with respect to the 2-oxabicyclic system, then said hydrogen atom is an exo-substituent and its absolute configuration is reported as β while when the chain

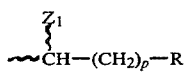

is in the exo-configuration, then said hydrogen atom is an endo-substituent and its absolute configuration is reported as α.

The compounds of the invention wherein the chain

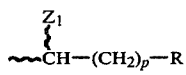

is in the exo-configuration, the hydrogen atom linked to the same carbon atom of the ring B having necessarily the α- absolute configuration, are reported as 6αH-6,9α-oxide (formula I; q=1) and 5αH-5,9α-oxide (formula I; q=2) prostanoic acid derivatives (prostaglandin numbering), while the compounds wherein the chain

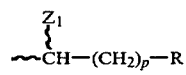

is in the endo-configuration, the hydrogen atom linked to the same carbon atom of the ring B having necessarily the β-absolute configuration, are reported as 6βH-6,9β-oxide (formula I; q=1) and 5αH-5,9α-oxide (formula I; q=2) prostanoic acid derivatives (prostaglandin numbering). Alternatively the 6αH-6,9α-oxide prostanoic acid derivatives are reported as (2'-oxa-bicyclo[3.3.0]octan-3'-exo-yl)-alkanoic acid derivatives, the 5αH-5,9α-oxide prostanoic acid derivatives as (2'-oxa-bicyclo[4.3.0]nonan-3'-exo-yl)-alkanoic acid derivatives, the 6βH-6,9α-oxide prostanoic acid derivatives as (2'-oxa-bicyclo[3.3.0]octan-3'-endo-yl)-akanoic acid derivatives and the 5βH-5,9α-oxide prostanoic acid derivative as (2'-oxa-bicyclo[4.3.0]nonan-3'-endo-yl)-alkanoic acid derivatives. The 6αH-6,9α-oxide and 5αH-5,9α-oxide prostanoic acid derivatives have a higher chromatographic mobility (i.e. a higher $R_f$) and a less positive rotatory power ($[α]_D$) than the corresponding 6βH-6,9α-oxide and 5βH-5,9α-oxide derivatives.

All the above notations refer to the natural compounds; the d,l-compounds are mixtures containing equimolar amounts of nat-compounds which possess the above reported absolute stereochemistry and of ent-compounds which are mirror-like images of the formers; in the ent-compounds the stereochemical configuration is the opposite at all the asymmetric centers with respect to the configuration of the natural compounds and the prefix ent indicates just this.

The alkyl, alkenyl, alkynyl, alkoxy, and alkanoyloxy groups are branched or straight chain groups.

Preferably R is a free, salified or esterified carboxy group.

An ar-$C_1$-$C_6$-alkoxy group is preferably benzyloxy.

An aryl group is preferably phenyl, α-naphtyl or β-naphtyl.

A halo-$C_1$-$C_6$-alkyl group is preferably trihalo-$C_1$-$C_6$-alkyl, in particular trifluoromethyl.

A $C_1$-$C_6$ alkyl group is preferably methyl, ethyl or propyl.

A $C_1$-$C_6$ alkoxy group is preferably methoxy, ethoxy or propoxy.

A $C_2$-$C_6$ alkenyl radical is preferably vinyl.

A $C_2$-$C_6$ alkynyl radical is preferably ethynyl.

When R is an esterified carboxy group it is preferably a —$COOR_c$ group wherein $R_c$ is a $C_1$-$C_{12}$ alkyl radical, in particular methyl, ethyl, propyl and heptyl, or a $C_2$-$C_{12}$ alkenyl radical, in particular allyl.

Preferably $Z_1$ is hydrogen.

When $Z_1$ is halogen, it is preferably chlorine or bromine.

p is preferably an integer of 1 to 3.

When $R_1$ is acyloxy, it is preferably $C_2$-$C_{12}$ alkanoyloxy (in particular $C_2$-$C_6$ alkanoyloxy, e.g., acetoxy, propionyloxy) or benzoyloxy.

When $Z_2$ is halogen, it is preferably chlorine, bromine or iodine.

Preferably $R_3$ and $R_4$ are independently selected from the group consisting of hydrogen, $C_1$-$C_6$ alkyl and fluorine.

$n_1$ is preferably zero or an integer of 1 to 3; $n_2$ is preferably an integer of 1 to 3.

When $R_6$ is a $C_3$-$C_9$ cycloaliphatic radical, it is preferably a $C_3$-$C_9$ cycloalkyl radical e.g. cyclopentyl, cyclohexyl and cycloheptyl or a $C_3$-$C_9$ cycloalkenyl radical, e.g. cyclopentenyl, cyclohexenyl and cycloheptenyl.

When $R_6$ is a heterocyclic ring, it may be either a heteromonocyclic ring or a heterobicyclic ring and contains at least one heteroatom selected from the group consisting of N, S and O.

Examples of preferred heteromonocyclic radicals are tetrahydrofuryl, tetrahydropyranyl, pyrrolyl, pyrazolyl, oxazolyl, isoxazolyl, pyridyl, pyrazinyl, pyrimidinyl, pyrizadinyl.

Examples of preferred heterobicyclic radicals are 2-oxa-bicyclo[3.3.0]octyl, 2-oxa-bicyclo[3.4.0]nonyl, 2-thia-bicyclo[3.3.0]octyl, 2-thia-bicyclo[3.4.0] nonyl and their aromatic analogs.

Pharmaceutically or veterinarily acceptable salts of the compounds of formula (I) are e.g. those with pharmaceutically and veterinarily acceptable bases. Pharmaceutically and veterinarily acceptable bases are either inorganic bases such as, for example, alkaline hydroxides and alkaline-earth hydroxides as well as aluminium and zinc hydroxides or organic bases e.g. organic amines such as, for example, methylamine, dimethylamine, trimethylamine, ethylamine, dibutylamine, N-methyl-N-hexylamine, decylamine, dodecylamine, allylamine, cyclopentylamine, cyclohexylamine, benzylamine, dibenzylamine, α-phenyl-ethylamine, β-phenyl-ethylamine, ethylenediamine, diethylenetriamine, morpholine, piperidine, pyrrolidine, piperazine, as well as the alkyl derivatives of the latter four bases, mono-, di- and tri-ethanolamine, ethyl-diethanolamine, N-methylethanolamine, 2-amino-1-butanol, 2-amino-2-methyl-1-propanol, N-phenyl-ethanolamine, galactamine, N-methyl-glucamine, N-methyl-glucosamine, ephedrine, procaine, dehydroabietilamine, lysine, arginine and other α or β amino acids.

Preferred salts of the invention are those of the compounds of formula (I) wherein R is —COOR$_d$ wherein R$_d$ is a pharmaceutically or veterinarily acceptable cation deriving from one of the above mentioned bases.

Particularly preferred compounds of the invention are 6βH-6,9α-oxide and 5βH-5,9α-oxide compounds of formula (I) wherein R is a free carboxy group and R$_6$ is $C_1$–$C_4$ alkyl, $C_5$–$C_7$ cycloalkyl or optionally substituted phenyl. The prefixes nor, dinor, trinor, tetranor- etc., are used to identify the compounds of formula (I) wherein the side chain bound to the cyclopentane ring A is one, two, three, four, etc. carbon atoms shorter than the analogous chain in the natural prostaglandins.

Specific examples of preferred compounds of the invention are the following:
13t-6βH-6,9α-oxide-11α,15S-dihydroxy-prost-13-enoic acid;
13t-6βH-6,9α-oxide-11α,15S-dihydroxy-prost-13-ynoic acid;
13t-6βH-6,9α-oxide-11α,15S-dihydroxy-prostanoic acid;
13t-6βH-6,9α-oxide-11α,15S-dihydroxy-15-methyl-prost-13-enoic acid;
13t-6βH-6,9α-oxide-11α,15S-dihydroxy-15-methyl-prost-13-ynoic acid;
13t-6βH-6,9α-oxide-11α,15S-dihydroxy-15-methyl-prostanoic acid;
13t-6βH-6,9α-oxide-11α,15S-dihydroxy-15,20-dimethyl-prost-13-enoic acid;
13t-6βH-6,9α-oxide-11α,15S-dihydroxy-15,20-dimethyl-prost-13-ynoic acid;
13t-6βH-6,9α-oxide-11α,15S-dihydroxy-15,20-dimethyl-prostanoic acid;
13t-6βH-6,9α-oxide-11α,15S-dihydroxy-20-methyl-prost-13-enoic acid;
13t-6βH-6,9α-oxide-11α,15S-dihydroxy-20-methyl-prost-13-ynoic acid;
13t-6βH-6,9α-oxide-11α,15S-dihydroxy-20-methyl-prostanoic acid;
13t-6βH-6,9α-oxide-15S-hydroxy-prost-13-enoic acid;
13t-6βH-6,9α-oxide-15S-hydroxy-prost-13-ynoic acid;
13t-6βH-6,9α-oxide-15S-hydroxy-prostanoic acid;
13t-6βH-6,9α-oxide-15S-hydroxy-15-methyl-prost-13-enoic acid;
13t-6βH-6,9α-oxide-15S-hydroxy-15-methyl-prost-13-ynoic acid;
13t-6βH-6,9α-oxide-15S-hydroxy-15-methyl-prostanoic acid;
13t-6βH-6,9α-oxide-15S-hydroxy-15,20-dimethyl-prost-13-enoic acid;
13t-6βH-6,9α-oxide-15S-hydroxy-15,20-dimethyl-prost-13-ynoic acid;
13t-6βH-6,9α-oxide-15S-hydroxy-15,20-dimethyl-prostanoic acid;
13t-6βH-6,9α-oxide-15S-hydroxy-20-methyl-prost-13-enoic acid;
13t-6βH-6,9α-oxide-15S-hydroxy-20-methyl-prost-13-ynoic acid;
13t-6βH-6,9α-oxide-15S-hydroxy-20-methyl-prostanoic acid;
13t-6βH-6,9α-oxide-11α,15S-dihydroxy-14-bromo-prost-13-enoic acid;
13t-6βH-6,9α-oxide-11α,15S-dihydroxy-14-chloro-prost-13-enoic acid;
13t-6βH-6,9α-oxide-11α,15S-dihydroxy-14-bromo-15-methyl-prost-13-enoic acid;
13t-6βH-6,9α-oxide-11α,15S-dihydroxy-14-bromo-20-methyl-prost-13 -enoic acid;
13t-6βH-6,9α-oxide-11α,15S-dihydroxy-14-bromo-15,20-dimethyl-prost-13-enoic acid;
13t-6βH-6,9α-oxide-11α,15S-dihydroxy-16,16-dimethyl-prost-13-enoic acid;
13t-6βH-6,9α-oxide-11α,15S-dihydroxy-16-methyl-16-butoxy-20,19,18-trinor-prost-13-enoic acid;
13t-6βH-6,9α-oxide-11α,15S-dihydroxy-16(S,R)-fluoro-17-cyclohexyl-20,19,18-trinor-prost-13-enoic acid and the single 16(S)- and 16(R)-fluoro isomer;
13t-6βH-6,9α-oxide-11α,15S-dihydroxy-17-cyclohexyl-20,19,18-trinor-prost-13-enoic acid;
13t-6βH-6,9α-oxide-11α,15S-dihydroxy-17-cyclohexyl-20,19,18-trinor-prost-13-ynoic acid;
13t-6βH-6,9α-oxide-11α,15S-dihydroxy-16-phenoxy-20,19,18,17-tetranor-13-enoic acid and the p-fluoro, p-chloro, p-methoxy, o-fluoro, m-fluoro, m-trifluoromethyl, m-chloro-phenoxy analogs thereof;
13t-6βH-6,9α-oxide-11α,15S-dihydroxy-17-(2'-tetrahydrofuryl)-20,19,18-trinor-prost-13-enoic acid;
13t-6βH-6,9α-oxide-11α,15S-dihydroxy-17-(2'-tetrahydrothienyl)-20,19,18-trinor-prost-13-enoic acid;
13t-6βH-6,9α-oxide-11α,15S-dihydroxy-20-ethyl-prost-13-enoic acid;
13t-6βH-6,9α-oxide-11α,15S-dihydroxy-16-benzyloxy-20,19,18,17-tetranor-13-enoic acid and the p-fluoro, p-chloro, p-methoxy, o-fluoro, m-fluoro, m-trifluoromethyl, m-chloro-benzyloxy analogs thereof;
13t-5βH-5,9α-oxide-11α,15S-dihyroxy-prost-13-enoic acid;
13t-5βH-5,9α-oxide-11α,15S-dihydroxy-prostanoic acid; 13t-5βH-5,9α-oxide-11α,15S-dihydroxy-prost-13-ynoic acid;
13t-5βH-5,9α-oxide-11α,15S-dihyroxy-16-methyl-prost-13-enoic acid;
13t-5βH-5,9α-oxide-11α,15S-dihydroxy-16R-methyl-prost-13-enoic acid;
13t-6βH-6,9α-oxide-11α,15S-dihydroxy-16S-methyl-prost-13-enoic acid;
13t-6βH-6,9α-oxide-11α,15S-dihydroxy-16R-methyl-prost-13-enoic acid;
13t-6βH-6,9α-oxide-11α,15S-dihydroxy-16S-methyl-prost-13-ynoic acid;
13t-6βH-6,9α-oxide-11α,15S-dihydroxy-16R-methyl-prost-13-ynoic acid,
as well as the 5-bromo, the 5-iodo, the 5-chloro analogs of all the 6βH-6,9α-oxide derivatives above listed, as well as the 4-bromo, the 4-iodo, the 4-chloro analogs of all the 5βH-5,9α-oxide derivatives above listed, as well as the 15R-epimers, the 15-oxo-derivatives and the 6αH- and the 5αH-diastereoisomers of all the compounds mentioned above.

The compounds of the invention are prepared by a process comprising:

(a) halocyclizing a compound of formula (II)

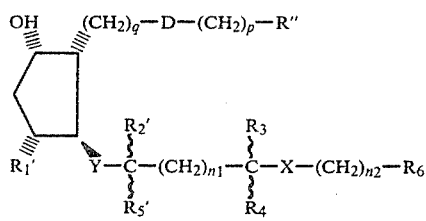

wherein p, q, Y, $n_1$, $n_2$, $R_3$, $R_4$, X and $R_6$ are as defined above, D is cis- or trans —CH=CH—, R" is (a") a free or esterified carboxy group; (b") a group

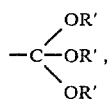

wherein each of the R' groups is as defined above; (c") the group —$CH_2$—$R_7$, wherein $R_7$ is hydroxy or a known protecting group bound to the —$CH_2$—group by an ethereal oxygen atom; (d")

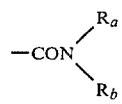

wherein $R_a$ and $R_b$ are as defined above; (e") a radical of formula

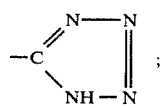

(f)—$R'_1$ is hydrogen, hydroxy, $C_1$-$C_6$ alkoxy, ar-$C_1$-$C_6$-alkoxy, acyloxy or a known protecting group bound to the ring by an ethereal oxygen atom; one of $R'_2$ and $R'_5$ is hydrogen, $C_1$-$C_6$ alkyl, $C_2$-$C_6$ alkenyl, $C_2$-$C_6$ alkynyl or aryl and the other is hydroxy, $C_1$-$C_6$ alkoxy, ar-$C_1$-$C_6$-alkoxy or a known protecting group bound to the chain by an ethereal oxygen atom, or $R'_2$ and $R'_5$, taken together, form an oxo group, so obtaining, after the removal of the known protecting groups, if present, a compound of formula (I) wherein $Z_1$ is halogen and, if necessary, deetherifying and/or, if desired, dehalogenating the obtained compound to give a compound of formula (I) wherein $Z_1$ is hydrogen; or (b) reducing a compound of formula (III)

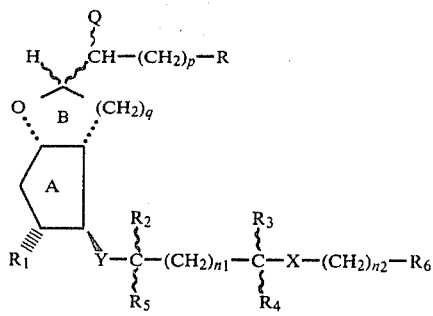

wherein Q is halogen or a group—$Hg^{(+)}Z^{(-)}$, wherein $Z^{(-)}$ is $OH^{(-)}$ or the anionic residue of an acid, R, p, q, $R_1$, Y, $R_2$, $R_5$, $R_3$, $R_4$, $n_1$, $n_2$, X and $R_6$ are as defined above, so obtaining a compound of formula (I) wherein $Z_1$ is hydrogen; or (c) reacting a compound of formula (IV)

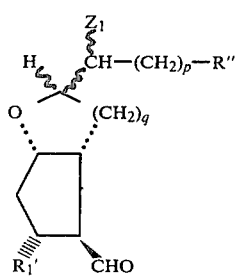

wherein R", p, $Z_1$, q, and $R_1'$ are as defined above, with a compound of formula (V)

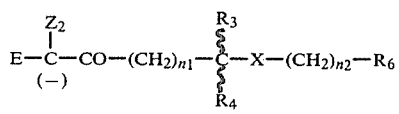

wherein E is a group

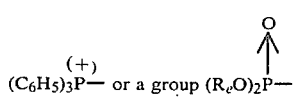

wherein each of the $R_e$ groups, which are the same or different, is alkyl or aryl and $Z_2$, $R_3$, $R_4$, $n_1$, $n_2$, X and $R_6$ are as defined above, so obtaining, after the removal of the known protecting groups, if present, a compound of formula (I) wherein $R_2$ and $R_5$, taken together, form an oxo group and Y is —CH=$CZ_2$— wherein $Z_2$ is as defined above and, if desired, reducing a compound of formula (I) wherein $R_2$ and $R_5$, taken together, form an oxo group and Y is —CH=$CZ_2$— wherein $Z_2$ is as defined above, to give a compound of formula (I) wherein one of $R_2$ and $R_5$ is hydrogen and the other is hydroxy and Y is —CH=$CZ_2$—, wherein $Z_2$ is as defined above, or, if desired, converting a compound of formula (I) wherein $R_2$ and $R_5$, taken together, form an oxo group and Y is —CH=$CZ_2$— wherein $Z_2$ is as defined above into a compound of formula (I) wherein one of $R_2$ and $R_5$ is hydroxy and the other is $C_1$-$C_6$ alkyl, $C_2$-$C_6$ alkenyl, $C_2$-$C_6$ alkynyl or aryl and, if desired, etherifying a compound of formula (I) wherein one of $R_2$ and $R_5$ is hydroxy and the other is hydrogen, $C_1$–$C_6$ alkyl, $C_2$–$C_6$ alkenyl, $C_2$–$C_6$ alkynyl or aryl and Y is —CH=$CZ_2$— wherein $Z_2$ is as defined above, to give a compound of formula (I) wherein one of $R_2$ and $R_5$ is $C_1$–$C_6$ alkoxy or ar-$C_1$–$C_6$-alkoxy and the other is hydrogen, $C_1$–$C_6$ alkyl, $C_2$–$C_6$ alkenyl, $C_2$–$C_6$ alkynyl or aryl and Y is —CH=$CZ_2$— wherein $Z_2$ is as defined above, and/or, if desired, hydrogenating a compound of formula (I) wherein Y is —CH=$CZ_2$— wherein $Z_2$ is hydrogen, to give a compound of formula (I) wherein Y is —$CH_2CH_2$— or, if desired, dehydrohalogenating a compound of formula (I) wherein $Z_1$ is hydrogen and Y is —CH=$CZ_2$— wherein $Z_2$ is halogen, to give a compound of formula (I) wherein Y is —C≡C— and $Z_1$ is hydrogen or, if desired, hydrogenating a compound of formula (I) wherein $R_2$ and $R_5$, taken together, form an oxo group and Y is —CH=$CZ_2$— wherein $Z_2$ is hydrogen, to give a compound of formula (I) wherein $R_2$ and $R_5$, taken together, form an oxo group and Y is —$CH_2CH_2$— or, if desired, dehydrohalogenating a compound of formula (I) wherein $Z_1$ is hydrogen, $R_2$ and $R_5$, taken together, form an oxo group, and Y is —CH=$CZ_2$— wherein $Z_2$ is halogen, to give a compound of formula (I) wherein $Z_1$ is hydrogen, $R_2$ and $R_5$, taken together, form an oxo group and Y is —C≡C— and, if desired, reducing a compound of formula (I) wherein $R_2$ and $R_5$, taken together, form an oxo group, to give a compound of formula (I) wherein one of $R_2$ and $R_5$ is hydrogen and the other is hydroxy, or, if desired, converting a compound of formula (I) wherein $R_2$ and $R_5$, taken together, form an oxo group, into a compound of formula (I) wherein one of $R_2$ and $R_5$ is hydroxy and the other is $C_1$–$C_6$ alkyl, $C_2$–$C_6$ alkenyl, $C_2$–$C_6$ alkynyl or aryl and, if desired, etherifying a compound of formula (I) wherein one of $R_2$ and $R_5$ is hydroxy and the other is hydrogen, $C_1$–$C_6$ alkyl, $C_2$–$C_6$ alkenyl, $C_2$–$C_6$ alkynyl or aryl, to give a compound of formula (I) wherein one of $R_2$ and $R_5$ is $C_1$–$C_6$ alkoxy or ar-$C_1$–$C_6$-alkoxy and the other is hydrogen, $C_1$–$C_6$ alkyl, $C_2$–$C_6$ alkenyl, $C_2$–$C_6$ alkynyl or aryl; and/or, if desired, converting a compound of formula (I) into another compound of formula (I) and/or, if desired, salifying a compound of formula (I) and/or, if desired, obtaining a free compound of formula (I) from a salt thereof and/or, if desired, separating a mixture of isomers into the single isomers. In the optional steps of the above processes when only one or a few substituents are specifically mentioned for a compound, it is understood that the other substituents have all the meanings previously indicated for formula (I).

The known protecting groups, i.e., ether groups, are convertible to hydroxy groups under mild reaction conditions, e.g., acid hydrolysis. Examples are acetal ethers, enol ethers and silyl ethers. The preferred groups are

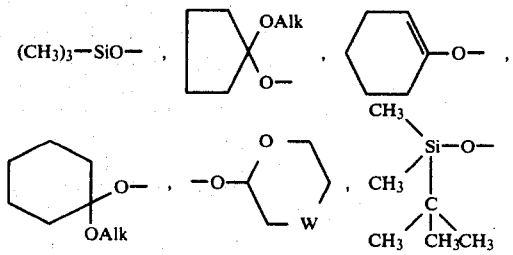

wherein W is —O— or —$CH_2$— and Alk is a lower alkyl group.

When in the compound of formula (III) Q represents a group $Hg^{(+)}Z^{(-)}$, wherein $Z^{(-)}$ is the anionic residue of an acid, $Z^{(-)}$ is preferably selected from the group consisting of $Cl^{(-)}$, $Br^{(-)}$, $I^{(-)}$, $R_8$—$COO^{(-)}$, wherein $R_8$ is an optionally halo-substituted $C_1$–$C_{12}$ alkyl group (preferably $C_1$–$C_6$ alkyl or trifluoromethyl) and

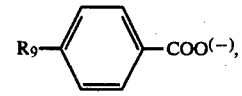

wherein $R_9$ is, e.g., hydrogen, $C_1$–$C_6$ alkyl, halogen, e.g., bromine, or trifluoromethyl.

Preferably $Z^{(-)}$ is $Cl^{(-)}$, $Br^{(-)}$, $CH_3COO^{(-)}$, $CF_3COO^{(-)}$ or

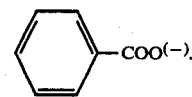

The halocyclization of a compound of formula (II) may be performed by reaction with either a stoichiometric amount or a small excess of a halogenating agent in an inert solvent, in either the presence or in absence of a base.

Preferred halogenating agents are, e.g., iodine, bromine, chlorine, bromodioxane, bromopyridine, $Br_2$.pyridine.HBr, $KI_3$, pyrrolidone-hydrotribromide, an N-haloamide such as N-chloro-succinimide, N-bromo-succinimide, N-iodo-succinimide, a cupric halide such as $CuCl_2$ or $CuBr_2$, a mixed halide such as ICl or IBr, as well as a mixture of an alkaline chloride with an alkaline chlorate, a mixture of an alkaline bromide with an alkaline bromate or a mixture of an alkaline iodide with an alkaline bromate. Suitable solvents are, for example, halogenated hydrocarbons such as $CHCl_3$, $CCl_4$, $CH_2Cl_2$; aliphatic hydrocarbons such as n-hexane, n-heptane; cycloaliphatic hydrocarbons such as cyclohexane; aromatic hydrocarbons such as benzene, toluene, pyridine, cyclic or linear ethers, e.g., dioxane, tetrahydrofuran, diethylether, dimethoxyethane; as well as mixtures thereof.

Preferred solvents are halogenated hydrocarbons, e.g. $CH_2Cl_2$, since both the compound of formula (II) and the halogenating agent are usually soluble in these solvents.

A stoichiometric amount of a base is necessary when a hydrohalic acid is formed during the halocyclization reaction.

Such a base may be an inorganic base, e.g., an alkaline or an alkaline-earth oxide, carbonate or bicarbonate, e.g., CaO, $CaCO_3$ and $K_2CO_3$, $NaHCO_3$, $Na_2CO_3$; an organic base such as a tertiary amine, e.g., triethylamine; or an aromatic base, e.g., pyridine or an alkyl-substituted pyridine; or an anionic ion-exchange resin.

The halocyclization reaction is preferably carried out at temperatures ranging from about −70° C. to about 100° C.; preferably the reaction is performed at room temperature.

The reaction times range from few minutes to several days, but usually do not exceed two hours and often a few minutes are sufficient to complete the reaction.

When other unsaturated bonds are present in the compound of formula (II) besides the double bond contained in the substituent D, those unsaturated bonds may add halogen during the halocyclization reaction. The added halogen may be easily removed to reobtain the original unsaturations, by treating the reaction product with an alkaline or alkaline-earth iodide in a suitable solvent such as, e.g., acetone at temperatures ranging from room temperature to reflux temperature but preferably at room temperature. Reaction time may range from about 2-3 hours to about 2-3 days.

The removal of the known protecting groups bound to the ring or to the chain by an ethereal oxygen atom is, whenever required, performed under conditions of mild acid hydrolysis, for example with a mono- or poly-carboxylic acid such as formic, acetic, oxalic, citric and tartaric acid, and in a solvent, which may be water, acetone, tetrahydrofuran, dimethoxyethane or a lower aliphatic alcohol, or with a sulphonic acid, e.g., p-toluenesulphonic acid in a solvent such as a lower aliphatic alcohol, dry methanol or dry ethanol, for example, or with a polystyrene-sulphonic resin. For example, 0.1 to 0.25 N poly-carboxylic acid (e.g., oxalic or citric acid) is used in the presence of a convenient low-boiling co-solvent which is misible with water and which can be easily removed in vacuo at the end of the reaction. All the cyclization reactions described in this specification such as e.g. the hereabove described halocyclization of a compound of formula (II) to give a compound of formula (I) wherein $Z_1$ is halogen, the herebelow described cyclization of a compound of formula (II) to give a compound of formula (III) wherein Q is $\sim$Hg(+)Z(−) and the herebelow described cyclization of a compound of formula (VI) are identical reactions as to their mechanism and the number of the isomers contained in the reaction mixture is the same for all the above cyclizations. Thus for example the above halocyclization reaction of a compound of formula (II) can give to a mixture of four components, i.e. compounds of formula (I) wherein $Z_1$ is halogen, consisting in a couple of diastereoisomers having the side chain

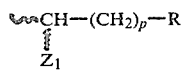

in the exo-configuration and differing each other for the S or R configuration of the halogen $Z_1$ and a couple of diastereoisomers having the side chain

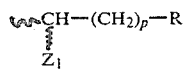

in the endoconfiguration and differing each other for the S or R configuration of the halogen $Z_1$.

While the chromatographic mobility ($R_f$) of the endo-isomer is clearly different from the chromatographic mobility of the exoisomer, the difference of $R_f$ between two endo- (or exo-) isomers differing each other only for the S or R configuration of the $Z_1$ substituent, is very small.

The couple of diastereoisomers wherein the chain

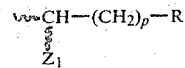

is in the exo-configuration may be separated from the couple of diastereoisomers wherein said chain is in the endo-configuration by fractional crystallization e.g. from diethylether but preferably by tin layer preparative chromatography, by column chromatography or by high speed liquid chromatography.

The separation by tin layer preparative chromatography or by column chromatography is preferably carried out on a support of silica gel or magnesium silicate with methylene chloride, diethylether, isopropylether, ethylacetate, benzene, methyl acetate, cyclohexane or their mixtures as elution solvents.

The reductive dehalogenation of a compound of formula (I) wherein $Z_1$ is halogen, to give a compound of formula (I) wherein $Z_1$ is hydrogen, is performed by reduction, e.g., with chromous acetate or a hydride such as tri(n-butyl)tin hydride, or by catalytic hydrogenation. When it is desired to obtain a compound of formula (I) wherein Y is $-C\equiv C-$ or $-CH=CZ_2-$ wherein $Z_2$ is as defined above, the dehalogenation is carried out only by reduction, e.g., with tri(n-butyl)tin hydride or chromous acetate.

When it is desired to obtain a compound of formula (I) wherein $R_2$ and $R_5$ taken together form an oxo group, by the dehalogenation of the compound of formula (I) wherein $Z_1$ is halogen, the reaction time should not exceed half an hour.

When the reductive dehalogenation is carried out with chromous acetate, this reagent is added, with stirring, to a cooled solution of the compound of formula (I) wherein $Z_1$ is halogen, in a mixture of ethanol and aqueous sodium or potassium hydroxide under an atmosphere of nitrogen. The reaction mixture is then stirred one to three days at room temperature, according to the method described in J.Am.Chem.Soc. 76, 5499 (1954).

When the dehalogenation is carried out with tri(n-butyl)tin hydride, about 1.2 equivalents of the reducing agent are used for each equivalent of the compound of formula (I) wherein $Z_1$ is halogen. Suitable solvents for the reaction are aromatic hydrocarbons such as benzene or toluene and the temperatures preferably are between room temperature and about 70° C.

Preferably the reaction is carried out at about 55° C. in benzene and lasts about 12 hours.

The catalytic hydrogenation of a compound of formula (I) wherein $Z_1$ is halogen to give a compound of formula (I) wherein $Z_1$ is hydrogen and Y is $-CH_2CH_2-$ may be performed eiher at room temperature or by heating this compound, e.g., at 30°-60° C. either at atmospheric pressure or under pressure, e.g., at 1.1-2 atm, in a solvent such as, e.g., a lower aliphatic alcohol, tetrahydrofuran, dioxane, benzene, toluene in the presence of a catalyst such as palladium or platinum on charcoal or $CaCO_3$ and optionally in the presence of an ammonium salt, e.g., ammonium acetate or proprionate.

The reductive dehalogenation converts a compound of formula (I) wherein $Z_1$ is halogen into a compound of formula (I) wherein $Z_1$ is hydrogen and therefore during the dehalogenation the carbon atom carrying the $Z_1$ substituent loses its asymmetry.

The number of the possible diastereoisomers consequently contained in the dehalogenation reaction mixture is lower than the number of diastereoisomers contained in the halocyclization reaction mixture. When the reductive dehalogenation is carried out directly on the mixture of four diastereoisomers obtained from the halocyclization process, a mixture of two only diastereoisomers of formula (I) wherein $Z_1$ is hydrogen is obtained, differing each other for the exo- or endo- configuration of the side chain ⌇CH$_2$—(CH$_2$)$_p$—R.

When the reductive dehalogenation is carried out on a single couple of diastereosiomers of formula (I) having the side chain

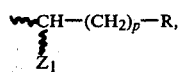

wherein $Z_1$ is halogen, in the exo- or in the endo-configuration and differing each other for the S or R configuration of $Z_1$, then only one isomer of formula (I) wherein $Z_1$ is hydrogen is obtained wherein the side chain ⌇CH$_2$—(CH$_2$)$_p$—R is in the exo- or in the endo-configuration.

If a mixture of the above diastereoisomers is obtained the single diastereoisomers may be easily separated by fractional crystallization or by column chromatography as described above for the separation of the diastereoisomers wherein $Z_1$ is halogen.

The reduction of the compound of formula (III) may be carried out by treatment with mixed hydrides such as alkaline, e.g., sodium, potassium or lithium, borohydrides, with alkaline-earth, e.g., calcium or magnesium, borohydrides in an inert solvent, preferably a solvent miscible with water, such as tetrahydrofuran, dimethoxyethane or lower aliphatic alcohols, e.g. methanol or ethanol; or with tri(n-butyl)tin hydride in benzene or toluene, preferably benzene; or also by treatment with hydrazine hydrate in a lower aliphatic alcohol, e.g., methanol or ethanol as solvent, at temperatures varying from room temperature to the reflux temperature of the solvent used.

When it is desired to obtain compounds of formula (I) wherein $Z_1$ is hydrogen and $R_2$ and $R_5$ taken together form an oxo group, the reduction of the compound of formula (III) is preferably carried out with tri(n-butyl)-tin hydride for a short reaction time, preferably a time varying from about 5 minutes to about half an hour.

During the above reduction of a compound of formula (III) the carbon atom carrying the Q substituent loses its asymmetry and therefore the number of the possible diastereoisomers contained in the reaction mixture at the end of the reduction process is half the number of the diastereoisomers contained in the starting material, analogously to what above reported with regards to dehalogenation of a compound of formula (I) wherein $Z_1$ is halogen.

When in the compound of formula (V) E is

wherein $R_e$ is aryl, it is preferably phenyl; when $R_e$ is alkyl, it is preferably $C_1$-$C_6$ alkyl. The reaction between an aldehyde of formula (IV) and a compound of formula (V) is carried out with an excess of the compound of formula (V), e.g., at least 1.01 molar equivalent of the compound of formula (V) for each mole of the compound of formula (IV).

Any inert solvent can be used, such as linear and cyclic ethers, e.g. ethyl ether, tetrahydrofuran, dioxane, dimethoxyethane, aliphatic or aromatic hydrocarbons, e.g., n-heptane, n-hexane, benzene, toluene or halogenated hydrocarbons, e.g. methylenechloride, tetrachloroethane and also mixtures of these solvents. The reaction temperature may vary between the freezing and the boiling points of the solvent.

When the reaction is carried out with a compound of formula (V) wherein E is

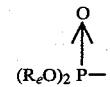

the preferred temperature is the room temperature i.e. from about 10° C. to about 25° C., when the reaction is carried out with a compound of formula (V) wherein E is

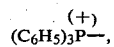

the preferred temperature is the reflux temperature of the solvent.

The product of the reaction between a compound of formula (IV) and a compound of formula (V) is a mixture of a compound of formula (I) wherein Y is trans-CH=CZ$_2$— wherein $Z_2$ is as defined above and a compound of formula (I) wherein Y is cis-CH=CZ$_2$— wherein $Z_2$ is as defined above, in a ratio varying between approximately 90:10 and 95:5.

The compound of formula (I) wherein Y is trans-CH=CZ$_2$— wherein $Z_2$ is as defined above, may be separated from the mixture by crystallization with a suitable solvent, while the compound of formula (I) wherein Y is cis-CH=CZ$_2$— wherein $Z_2$ is as defined above, may be obtained by concentration of the mother liquor and subsequent chromatographic separation of the residue, either by column or preparative TLC chromatography using silica gel or magnesium silicate as support and e.g. methylene chloride, diethylether, isopropylether, ethylacetate, benzene, cyclohexane or their mixtures as elution solvents.

The removal of the protecting groups, if present, may be performed by mild acid hydrolysis as described above for the compounds obtained by the halocyclization and the reduction processes.

Either the optional reduction of a compound of formula (I) wherein $R_2$ and $R_5$, taken together form an oxo group, and Y is —CH=CZ$_2$—, wherein $Z_2$ is as defined above, to give a compound of formula (I) wherein Y is —CH=CZ$_2$—, wherein $Z_2$ is as defined above and wherein one of $R_2$ and $R_5$ is hydrogen and the other is hydroxy or the optional conversion of a compound of formula (I) wherein $R_2$ and $R_5$, taken together form an oxo group and Y is —CH=CZ$_2$— wherein $Z_2$ is as defined above, into a compound of formula (I) wherein Y is —CH=CZ$_2$—, wherein $Z_2$ is as defined above, and wherein one of $R_2$ and $R_5$ is hydroxy and the other is $C_1$-$C_6$ alkyl, $C_2$-$C_6$ alkenyl, $C_2$-$C_6$ alkynyl or aryl must be regarded as different applications of one only reaction which is a 1.2 polar addition to the carbonyl group. The optional reduction of an obtained compound of formula (I) wherein $R_2$ and $R_5$ taken together form an oxo group, and Y is —CH=CZ$_2$—, wherein Z$_2$ is as defined above, to give a compound of formula (I) wherein Y is —CH=CZ$_2$—, wherein Z$_2$ is as defined above, and wherein one of R$_2$ and R$_5$ is hydrogen and the other is hydroxy, is preferably carried out with alkaline or alkaline-earth metal borohydrides, preferably sodium, lithium, calcium, magnesium or zinc borohydride, using from 0.5 to 6 moles of the reducing agent for each mole of the compound of formula (I). The reduction may be performed either in aqueous or anhydrous inert solvents such as linear or cyclic ethers, e.g., ethyl ether, tetrahydrofuran, dimethoxyethane, dioxane or aliphatic or aromatic hydrocarbons, e.g., n-heptane or benzene, or halogenated hydrocarbons, e.g. methylene dichloride, or hydroxylated solvents, e.g., ethyl, methyl or isopropyl alcohol, or mixtures of these solvents.

The reaction temperature may vary between approximately −40° C. and the boiling point of the solvent used, but the preferred temperature ranges from about −20° C. to about 25° C.

This reduction leads to a mixture of the two epimeric

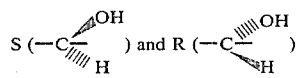

alcohols from which the single epimers can be separated, if desired, by fractional crystallization, e.g. with diethylether, n-hexane, n-heptane, cyclohexane but preferably by chromatography either on silica gel or magnesium silicate columns or preparative TLC chromatography with, for example, silica gel, eluting, e.g., with CH$_2$Cl$_2$, ethyl ether, isopropyl ether, ethyl acetate, methyl acetate, benzene, cyclohexane or mixtures of these, or by high speed liquid chromatography.

The optional conversion of a compound of formula (I) wherein R$_2$ and R$_5$ taken together form an oxo group and Y is —CH=CZ$_2$—, wherein Z$_2$ is as defined above, into a compound of formula (I) wherein one of R$_2$ and R$_5$ is hydroxy and the other is C$_1$-C$_6$ alkyl, C$_2$-C$_6$ alkenyl, C$_2$-C$_6$ alkynyl or aryl and Y is —CH=CZ$_2$— wherein Z$_2$ is as defined above, may be carried out by treatment with a Grignard reagent of formula R'''-MgHal, wherein Hal is halogen, preferably bromne or iodine and R''' is C$_1$-C$_6$ alkyl, C$_2$-C$_6$ alkynyl, C$_2$-C$_6$ alkenyl or aryl, preferably methyl, vinyl, ethynyl, phenyl. The Grignard reaction is carried out with 1.05 to 2 moles of the magnesium derivative for each mole of ketone, operating in anhydrous solvents which may be linear or cyclic ethers, e.g., ethyl ether, tetrahydrofuran, dioxane, dimethoxyethane or aliphatic or aromatic hydrocarbons, e.g., n-heptane, n-hexane, benzene, toluene, at temperatures varying from approximately −70° C. to the boiling point of the solvent used. The preferred temperatures range between −60° C. and 10° C.

The optional etherification of a compound of formula (I) wherein Y is —CH=CZ$_2$—; wherein Z$_2$ is as defined above, and one of R$_2$ and R$_5$ is hydroxy and the other is hydrogen, C$_1$-C$_6$ alkyl, C$_2$-C$_6$ alkenyl, C$_2$-C$_6$ alkynyl or aryl to give a compound of formula (I) wherein Y is —CH=CZ$_2$—, wherein Z$_2$ is as defined above, and one of R$_2$ and R$_5$ is C$_1$-C$_6$ alkoxy or aralkoxy and the other is hydrogen, C$_1$-C$_6$ alkyl, C$_2$-C$_6$ alkenyl, C$_2$-C$_6$ alkynyl or aryl, may be carried out, for example, by reaction with an optionally aryl-substituted diazoalkane in the presence of a catalyst such as fluoboric acid or borotri-fluoride and in an organic solvent such as dichloromethane or by reaction of the free or salified hydroxy group with an alkyl or aralkyl halide in presence of a base such as silver oxide and in a solvent such as dimethylsulphoxide or dimethylformamide.

The optional hydrogenation of a compound of formula (I) wherein Y is —CH=CZ$_2$—, wherein Z$_2$ is hydrogen, to give a compound of formula (I) wherein Y is —CH$_2$—CH$_2$— is carried out e.g., catalytically, preferably in an alcoholic solvent, in the presence of platinum or palladium on charcoal as catalyst at temperatures varying from about −40° C. to the reflux temperature of the solvent. When it is desired to obtain compounds of formula (I) wherein Z$_1$ is halogen and Y is —CH$_2$—CH$_2$— the hydrogenation is preferably carried out at temperatures ranging from about −40° C. to about −20° C.

The optional dehydrohalogenation of a compound of formula (I) wherein Z$_1$ is hydrogen, and Y is —CH=CZ$_2$—, wherein Z$_2$ is halogen, so as to obtain the corresponding compounds of formula (I) wherein Z$_1$ is hydrogen and Y is —C≡C—, may be carried out using a dehydrohalogenating agent preferably selected from the group consisting of a dimethylsulfinylcarbanion of formula CH$_3$SOCH$_2{}^{(-)}$, diazabicycloundecene, diazabicyclononene, the amide or the alkoxide of an alkaline metal. From 1 to 5, and preferably from 1.5 to 1.8, molar equivalents of the basic dehydrohalogenating agent may be employed for each mole of the compound of formula (I) wherein Y is —CH=CZ$_2$—, wherein Z$_2$ is halogen.

This dehydrohalogenation process is preferably carried out in the absence of atmospheric oxygen, in an inert solvent such as dimethylsulphoxide, dimethylformamide, hexamethylphosphoramide; a linear or cyclic ether, e.g., dimethoxyethane, tetrahydrofuran, dioxane; an aromatic hydrocarbon, e.g., benzene, toluene; or liquid ammonia or a mixture of these solvents. The reaction temperature may vary between the liquefaction point of the ammonia and approximately 100° C., but the preferred temperature is room temperature.

Depending on the solvent, the reaction temperature and the molar ratio used between the reagent and the compound, the reaction time may vary from a few minutes to several hours.

The optional reduction of a compound of formula (I) wherein R$_2$ and R$_5$ taken together form an oxo group and Y is —CH$_2$—CH$_2$— or —C≡C— to give a compound of formula (I) wherein one of R$_2$ and R$_5$ is hydrogen and the other is hydroxy and Y is —CH$_2$—CH$_2$— or —C≡C— may be carried out as described above for the analogous reduction of a compound of formula (I) wherein R$_2$ and R$_5$ taken together form an oxo group and Y is —CH=CZ$_2$—, wherein Z$_2$ is as defined above. The optional conversion of a compound of formula (I) wherein R$_2$ and R$_5$ taken together form an oxo group and Y is —CH$_2$—CH$_2$ or —C≡C— into a compound of formula (I) wherein one of R$_2$ and R$_5$ is hydroxy and the other is C$_1$-C$_6$ alkyl, C$_2$-C$_6$ alkenyl, C$_2$-C$_6$ alkynyl or aryl may be effected under the same reaction conditions described above for the analogous conversion of the compounds of formula (I) wherein Y is —CH=CZ$_2$—, wherein Z$_2$ is as defined above.

Also the optional etherification of a compound of formula (I) wherein one of R$_2$ and R$_5$ is hydroxy and the other is hydrogen or C$_1$-C$_6$ alkyl, C$_2$-C$_6$ alkenyl, C$_2$-C$_6$ alkynyl or aryl and Y is —CH$_2$—CH$_2$— or —C≡C— may be carried out as described above for the etherification of a compound of formula (I) wherein one of $R_2$ and $R_5$ is hydroxy and the other is hydrogen, $C_1$–$C_6$ alkyl, $C_2$–$C_6$ alkenyl, $C_1$–$C_6$ alkynyl or aryl and Y is —CH=$CZ_2$—, wherein $Z_2$ is as defined above.

The optional conversion of a compound of formula (I) into another compound of formula (I) as well as the salification of a compound of formula (I), the preparation of a free compound from a salt and the separation of the isomers from a mixture may be carried out by known methods.

Thus, for example, a compound of formula (I) wherein one of $R_2$ and $R_5$ is hydrogen and the other is hydroxy may be converted into a compound of formula (I) wherein $R_2$ and $R_5$ taken together form an oxo group by oxidation. The oxidation may be carried out by treatment with an excess of activated manganese dioxide in an inert solvent preferably a halogenated inert solvent such as dichloromethane or chloroform at room temperature for a reaction time varying between several hours and one or more days.

Alternatively, the oxidation may be carried out by reaction with a 1.1–1.2 molar equivalent of dichlorodicyanobenzoquinone (DDQ) in an inert solvent such as dioxane, tetrahydrofuran, benzene or a mixture of these at temperatures ranging from about 40° C. to the boiling point of the solvent. A compound of formula (I) wherein R is a free carboxy group may be converted into a compound of formula (I) wherein R is an esterified carboxy group, e.g., a $C_1$–$C_{12}$carbalkoxy group, by known methods, e.g., by reaction with the appropriate alcohol, e.g., a $C_1$–$C_{12}$ aliphatic alcohol, in the presence of an acid catalyst, e.g., p-toluenesulphonic acid and also by treatment with a diazoalkane. The optional conversion of a compound of formula (I) wherein $R_1$ is hydroxy into a compound of formula (I) wherein $R_1$ is acyloxy, if desired, may be performed in a conventional manner, e.g., by treatment with an anhydride or a halide, such as a chloride of the appropriate carboxylic acid in the presence of a base. When one of $R_2$ and $R_5$ is hydroxy, this hydroxy group may be protected before the acylation by one of the known protecting group mentioned above.

The optional conversion of a compound of formula (I) wherein R is an esterified carboxy group into a compound of formula (I) wherein R is a free carboxy group, if desired, may be carried out by the usual methods of saponification, e.g., by treatment with an alkaline or alkaline-earth hydroxide in aqueous or alcoholic aqueous solution followed by acidification. In a compound of formula (I) wherein R is an esterified carboxy and $R_1$ is acyloxy, the optional saponification may be carried out selectively with respect to the esterified carboxy, if desired, by transesterification, i.e., by reacting it in the same alcohol which esterifies the carboxy groups and in the presence of a base such as an alkaline or alkaline-earth alkoxide or $K_2CO_3$.

The optional conversion of a compound of formula (I) wherein $R_1$ is hydroxy into a compound of formula (I) wherein $R_1$ is $C_1$–$C_6$ alkoxy or aralkoxy, if desired, may be carried out by the usual methods of the etherification, for example as described above for the etherification of a compound of formula (I) wherein one of $R_2$ and $R_5$ is hydroxy.

When it is desired to etherify only one of several hydroxyl functions present it is useful to protect before the etherification the hydroxy groups which it is desired to not etherify, e.g., with the known protecting groups above mentioned, then removing these at the end of the etherification by the procedures already described above.

The optional conversion of a compound of formula (I) wherein R is a free or esterified carboxy group into a compound of formula (I) wherein R is —$CH_2$—OH, if desired, may be carried out, e.g., by reducing the ester with $LiAlH_4$ in ethyl ether or tetrahydrofuran at reflux temperature.

The optional conversion of a compound of formula (I) wherein R is a free carboxy group into a compound of formula (I) wherein R is

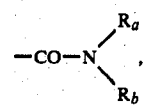

wherein $R_a$ and $R_b$ are as defined above, may be performed by treatment with an amine of formula $NHR_aR_b$ in the presence of a condensing agent, e.g., a carbodiimide such as dicyclohexylcarbodiimide, and the optional conversion of a compound of formula (I) wherein R is an esterified carboxy into a compound of formula (I) wherein R is

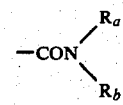

may be effected by treatment with an amine of formula $NHR_aR_b$ in a suitable organic solvent at reflux temperature for 2–3 hours.

The optional conversion of a compound of formula (I) wherein R is a free carboxy group into a compound of formula (I) wherein R is a radical

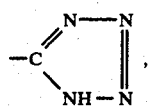

may be carried out by converting the carboxy group into the corresponding halide, preferably chloride, e.g., by reaction with thionyl chloride or oxalyl chloride in dioxane or dichloroethane at reflux temperature, then reacting the halide, e.g., with ammonia, to give the amide, dehydrating the amide to nitrile, e.g., with p-toluenesulphonylchloride in pyridine at approximately 90°–100° C., and finally reacting the nitrile with sodium azide and ammonium chloride in dimethylformamide at a temperature varying between the room temperature and 100° C. But preferably the hereabove reported conversions of the carboxy group into -CN or

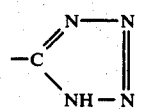

are performed on the starting materials i.e. for example of the compounds of formula (II) and (VI).

The optional salification of a compound of formula (I) may be performed in a conventional manner.

Also the optional separation of the optically active compounds from a racemic mixture as well as the optional separation of the diastereoisomers or of the geometrical isomers from their mixtures may be effected by conventional methods.

The compounds of formula (II) are already known compounds and may be prepared, e.g., as described by E. J. Corey et al, Ann. of New York Acad. of Sciences, 180, 24 (1971), By J. Fried et al, J.Med.Chem. 16, 429 (1973), G. L. Bundy et al, Amer.Chem.Soc. 94, 2124 (1972), by Gandolfi et al, Il Farmaco Ed.Sc. 27, 1125 (1972), in the U.S. Pat. No. 3,935,254, Derwent Farmdoc 20717 X, in the German Offenlegunsschrift No. 26 11 788 (Derwent Farmdoc 61615X), in the German Offenlegungschrift No. 26 10 503 (Derwent Farmdoc 59715X), in the German Offenlegungsschrift No. 26 27 422 (Derwent Farmdoc 85028X), in the U.S. Pat. No. 3,706,789, in the U.S. Pat. No. 3,728,382, in the U.S. Pat. No. 3,903,131, in the U.S. Pat. No. 3,962,293, in the U.S. Pat. No. 3,969,380, Derwent Farmdoc 73279U, Derwent Farmdoc 31279T, in the U.S. Pat. No. 3,890,372, in the U.S. Pat. No. 3,636,120, in the U.S. Pat. No. 3,883,513, in the U.S. Pat. No. 3,932,389, in the U.S. Pat. No. 3,932,479, Derwent Farmdoc 19594W, Derwent Farmdoc 54179 U and in the British Pat. No. 1,483,880.

The compound of formula (III) wherein Q is halogen may be obtained by the same reaction described above for the synthesys of the compound of formula (I) wherein $Z_1$ is halogen. The compound of formula (III) wherein Q is a group $\sim$Hg$^{(+)}Z^{(-)}$ wherein $Z^{(-)}$ is as defined above may be prepared by cyclizing a compound of formula (II) in the presence of a source of Hg$^{(++)}$ ions. Suitable sources of Hg$^{(++)}$ ions may be, e.g., either compounds of formula Hg(Z)$_2$ or compounds of formula Hg(OH)Z. The above cyclization may be performed, e.g., using 1.01 to 1.5, preferably 1.2, equivalents of the mercuric compound for each mole of the compound of formula (II), in an organic solvent miscible with water, e.g., tetrahydrofuran, methanol, ethanol or in a mixture of the organic solvent and water. The reaction temperature may vary between 0° C. and the boiling point of the reaction mixture and the reaction time ranges from about 5 minutes to about 2 hours. The cyclization gives a mixture of four diastereoisomers of formula (III) differing from each other for the configuration (endo or exo) of the side chain linked to the heterocyclic ring B or for the configuration (S or R) of the Q substituent.

The separation of the diastereoisomers from their mixture, which may be carried out according to known methods, e.g., those already described above, may be effected at this point or, if desired, after the reduction of the compound of formula (III).

The compound of formula (IV) wherein $Z_1$ is halogen may be prepared by halocyclization of a compound of formula (VI)

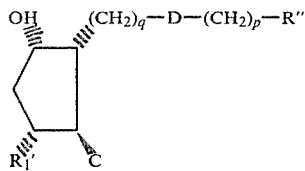
(VI)

wherein R", p, q, D and R'$_1$ are as defined above and G is a protected aldehydic group or a protected —CH- $_2$OH group, preferably a member selected from the group consisting of

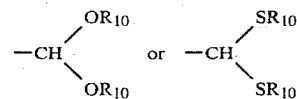

wherein R$_{10}$ is C$_1$–C$_6$ alkyl;

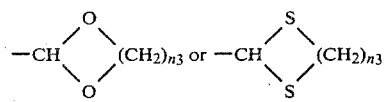

wherein $n_3$ is an integer of 2 to 4, preferably 2 or 3; —CH$_2$—O—CH$_2$—C$_6$H$_5$ or —CH$_2$—O—CH$_2$SCH$_3$, followed by the removal of the protecting groups and by the selective oxidation of —CH$_2$OH, when obtained, to —CHO.

The halocyclization of the compound of formula (VI) may be performed using the same reaction conditions described above for the conversion of a compound of formula (II) into a compound of formula (I) wherein $Z_1$ is halogen.

The removal of the protecting group from the aldehydic or alcoholic functions may be carried out by mild acid hydrolysis in the same conditions already described in this specification for the removal of the protecting groups (i.e. ether groups) of the hydroxylic functions. The selective oxidation of —CH$_2$OH to —CHO may be effected in a conventional manner, e.g. by treatment with an excess of at least 3 moles per mole of primary alcohol of dicyclohexylcarbodiimide in benzene-dimethylsulphoxide and in the presence of an acid catalyst, e.g., pyridine trifluoroacetate or phosphoric acid.

The compound of formula (IV) wherein $Z_1$ is hydrogen may be prepared either by the dehalogenation of a compound of formula (IV) wherein $Z_1$ is halogen according to the method reported above for the conversion of a compound of formula (I) wherein $Z_1$ is halogen into a compound of formula (I) wherein $Z_1$ is hydrogen or by a process comprising the cyclization of a compound of formula (VI) in the presence of a source of Hg$^{(++)}$ ions [as already described for the preparation of a compound of formula (III) wherein Q is $\sim$Hg$^{(+)}Z^{(-)}$] and the subsequent reduction of the obtained compound using the same reaction conditions employed for the reduction of a compound of formula (III).

The compound of formula (V) wherein E is

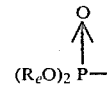

may be prepared by treatment of a phosphonate of formula (VII)

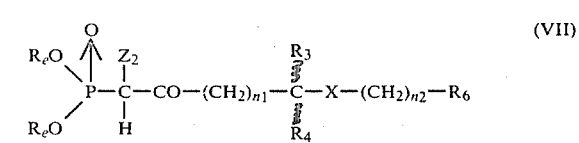
(VII)

wherein R$_e$, Z$_2$, n$_1$, R$_3$, R$_4$, X, n$_2$ and R$_6$ are as defined above, with at least an equivalent of a base preferably selected from the group consisting of an alkaline or alkaline-earth hydride, e.g., sodium, potassium, lithium or calcium hydride; an alkaline alkoxide, e.g., sodium or potassium tert.butoxide; an alkaline or alkaline-earth metal amide, e.g., sodium amide; an alkaline or alkaline-earth derivative of a carboxy-amide, e.g., sodium acetamide or sodium succinimide.

The compound of formula (V) wherein E is

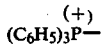

may be prepared by reacting a compound of formula (VIII)

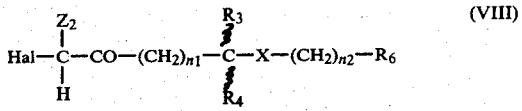

wherein $Z_2$, $n_1$, $R_3$, $R_4$, X, $n_2$, $R_6$ are as defined above and Hal is a halogen atom, with 1–1.2 molar equivalent of triphenylphosphine in an inert organic solvent such as e.g. benzene, acetonitrile, diethylether, then treating the triphenylphosphonium halide so obtained with an equivalent amount of an inorganic base such as, for example, NaOH, KOH, $Na_2CO_3$, $NaHCO_3$.

The compound of formula (VI) may be prepared, e.g., according to Tetrahedron Letters No. 42, 4307–4310 (1972).

The compound of formula (VII) wherein $Z_2$ is halogen may be obtained by halogenating a compound of formula (VII) wherein $Z_2$ is hydrogen in a conventional manner, operating substantially as in the halogenation of β-ketoesters.

The compounds of formula (VII) wherein $Z_2$ is hydrogen may be prepared by known methods, e.g. according to E. J. Corey et al, J. Am. Chem. Soc. 90, 3247 (1968) and E. J. Corey and G. K. Kwiatkowsky, J. Am. Chem. Soc., 88, 5654 (1966).

The compounds of formula (VIII) are known compounds or may be prepared by known methods.

The compounds of the invention can be used, in general, for the same therapeutic indications as the natural prostaglandins in either human or veterinary medicine.

In particular, those having an acetylene bond in the 13,14-position instead of an ethylene and those with mono and di-substituents such as methyl and fluorine groups have the advantages of superior resistance to degradation by the 15-PG-dehydrogenase enzymes, which quickly inactivate natural compounds, and, of a more selective therapeutic action, as indicated below.

In order to obtain a preliminary biological profile, i.e., to assess whether the compounds of the invention possess PG-like or thromboxane (TXA$_2$)-like or PGX-like activity, they were at first tested by a superfusion cascade technique by the method of Piper and Vane, Nature 223, 29 (1969).

In order to increase the sensitivity of the bioassay, a mixture of antagonists [Gilmore et al. Nature 218, 1135 (1968)] is added to the Krebs-Henseleit and indomethacin (4 μg/ml) is also added to prevent the endogenous biosynthesis of prostaglandins.

Contraction of rat colon (RC), rat stomach strip (RSS) and bovine coronary artery (BCA), and relaxation of rabbit mesentery artery (RbMA) are assumed to represent prostaglandin-like activity. TXA$_2$-like activity is indicated when RbMA is contracted and must be confirmed by in vitro platelet pro-aggregation activity, since PGF$_{2\alpha}$-like compounds also contract RbMA, as opposed to PGE. Finally, PGX-like activity is indicated by the relaxation of BCA, and is confirmed by in vitro platelet anti-aggregation activity. Synthetic PGE$_2$ and both the biosynthetic TXA$_2$ and PGX are utilized as standard compounds.

They are active at a range of concentrations from 1–5 μg/ml. The compounds of the invention were dissolved in a few drops of ethanol just before testing; the stock solution was prepared in 0.1 M tris-buffer, pH 9.0, (1 mg/ml) and diluted with Krebs-Henseleit to the required concentration.

The compound 13-trans-11α,15S-dihydroxy-6βH-6,9α-oxide-prostenoic acid was taken as the parent compound and is called 6βH-6,9α-oxide; the diastereoisomer 13-trans-11α,15S-dihydroxy-6αH-6,9α-oxide-prostenoic acid is then referred to as 6αH-6,9α-oxide. The chemical names of the other tested compounds are also referred to those of the parent compounds. The compounds were tested at concentrations up to 100 ng/ml.

The results obtained showed that, in general, the 6βH-diastereoisomers, e.g., the compounds 6βH-6,9α-oxide, dl-6βH-5-bromo-6,9α-oxide, 6βH-6,9β-oxide-16-m-CF$_3$-phenoxy-ω-tetranor and 6βH-6,9α-oxide-16-m-chloro-phenoxy-ω-tetranor possess BCA-relaxing activity and therefore have PGX-like activity.

Among the 6βH-derivatives, only the compound dl-6βH-6,9α-oxide-16-methyl-16-butoxy-ω-tetranor showed a BCA-contracting activity. The 6αH-derivatives, e.g. the compound 6αH-6,9α-oxide, dl-6αH-5-bromo-6,9α-oxide, dl-6αH-6,9α-oxide-16-methyl-16-butoxy-ω-tetranor, 6αH-6,9α-oxide-16-m-CF$_3$-phenoxy-ω-tetranor and 6αH-6,9α-oxide-16-m-chloro-phenoxy-ω-tetranor also showed BCA-contracting activity.

In general, the exo-configuration is associated with BCA contraction. Furthermore, the compounds of the invention have hypotensive activity in mammals as does the natural compound PGX. However, as compared to PGX, they have the great advantage of a higher chemical stability and can be used in pharmaceutical formulations.

The hypotensive activity was demonstrated by the limb perfusion test. During the perfusion of the rat's left leg, through the left femoral artery, with a constant perfusion pressure, both the 6βH- and 6αH-6,9α-oxide compounds caused a lowering of the values of the mean perfusion pressure at all the doses, over the range from 0.05–1 μg (to −42,5% for 6βH and −32% for 6αH). Moreover, the systemic pressure, both systolic and diastolic, was depressed from 0.05 μg/kg up to 5 μg/kg (about −45%).

Because of their hypotensive and vasodilatory activity, the compounds of the invention are useful for treatment of cases of gangrene of the lower limbs. For this therapeutic use they have been found to be more active than PGE$_1$ and PGE$_2$. They are also useful in disturbances of the peripheral vasculature and, therefore in the prevention and treatment of diseases such as phlebitis, hepato-renal syndrome, ductus arteriosus, non-obstructive mesenteric ischemia, arteritis and ischemic ulcerations of the leg.

Among the compounds of the invention, in particular, the 6βH-derivatives also have a high anti-aggregating activity.

Among the 6βH compounds, the more important ones are, in order of increasing potency, compounds dl-6βH-5-bromo-6,9α-oxide, 6βH-6,9α-oxide-16-m-CF$_3$-phenoxy-ω-tetranor, dl-6βH-6,9α-oxide, and 6βH-6,9α-oxide.

Using platelet-rich plasma (PRP) from healthy human donors who had not taken any drugs for at least one week, and monitoring platelet aggregation by continous recording of light transmission in a Born aggregometer [Born G.V.R., Nature (London) 194, 927 (1962)] there is evidence that the compounds 6βH-6,9α-oxide, dl-6βH-5-bromo-6,9α-oxide, 6βH-6,9α-oxide-16-m-CF$_3$-phenoxy-ω-tetranor and 6βH-6,9α-oxide-16-m-chloro-phenoxy-ω-tetranor mimic the biosynthetic PGX in its platelet-antiaggregating properties.

The compounds investigated were incubated for 2–3 minutes at 37° C. in the PRP prior to the addition of the aggregating agents, arachidonic acid (0.4 mM), ADP (10 μM), collagen (38 μM) or adrenaline (15 μM). The potency ratio for the compound is, e.g., 1:10 for arachidonic acid-induced aggregation and 1:100 for ADP-induced aggregation, as compared with biosynthetic PGX.

A very interesting increase in the anti-aggregating potency follows 20-methyl substitution in both the 6βH- and 6αH-6,9α-oxide parent compounds. Similarly, 6βH-5-bromo-20-methyl, 6βH-5,14-dibromo, 6βH-13,14-didehydro-20-methyl and finally 6βH-5-bromo-13,14-didehydro compounds and their 6βH-5-iodo (but not 6αH-5-iodo isomers) are very active compounds as anti-aggregating agents. The compounds of the invention are, therefore, particularly useful in mammals for inhibiting platelet aggregation, for preventing and inhibiting thrombus formation and for decreasing the adhesiveness of platelets.

Therefore, they are useful in treatment and prevention of thromboses and myocardial infarct, in treatment of atherosclerosis, and in general in all syndromes etiologically based on or associated with lipid imbalance or hyperlipidemia, as well as in treatment of geriatric patients for prevention of cerebral ischemic episodes, and in long-term treatment after myocardial infarct.

When the compounds of the invention are given as anti-aggregating agents, the routes of administration are the usual ones, oral, intravenous, subcutaneous, intramuscular. In emergency situations, the preferred route is intravenous, with doses that can vary from 0.005 to about 10 mg/kg/day. The exact dose will depend on the condition of the patient, his weight, his age and the route of administration.

The compound of the invention were also studied for their uterine contractile activity, both in vitro and in vivo, against PGF$_{2\alpha}$ as standard.

For example, in vitro, on the uterus of the estrogenized rat, compounds 6αH-6,9α-oxide-16-m-chloro-phenoxy-ω-tetranor and 6βH-6,9α-oxide-16-m-CF$_3$-phenoxy-ω-tetranor, were 1.3 and 3.1 times as active as PGF$_{2\alpha}$.

In the in vivo assay, measuring the intrauterine pressure of the ovariectomized rabbit, the same compounds were 5.9 and 8.25 times as active as PGF$_{2\alpha}$ (see the following Table)

| | in vitro | | in vivo |
|---|---|---|---|
| | Uterus | Ileum | |
| PGF$_{2\alpha}$ | 1 | 1 | 1 |
| 6αH-6,9α-oxide-16-m-chloro-phenoxy-ω-tetranor | 1.3 | 0.05 | 5.9 |
| 6βH-6,9α-oxide-16-m-CF$_3$-phenoxy-ω-tetranor | 3.1 | 0.1 | 8.25 |

The table shows that the compounds have greater activity on the uterus than on the gastrointestinal tract.

These compounds, which are useful for induction of labor, for expulsion of dead fetuses from the pregnant female, in either human or veterinary medicine, are without the undesirable side effects of the natural prostaglandins, such as vomiting and diarrhea.

For this purpose the compounds of the invention can be given by intravenous infusion, at a dose of about 0.01 μg/kg/minute until the end of labor. At the same dosage, the compounds of the invention dilate the uterine cervix, facilitating therapeutic abortion and, in that situation are given preferably in the form of vaginal tablets or suppositories.

The compounds of the invention, in particular the compound dl-6βH-6,9α-oxide-16-m-chloro-phenoxy-ω-tetranor also have luteolytic activity and are therefore of use for control of fertility.

The 6βH-6,9α-oxide and their 6αH-isomers were also investigated for their action on the gastrointestinal tract, in order to know: (a) cytoprotective activity against lesions induced by non-steroid anti-inflammatory drugs; (b) ability to prevent the ulcers induced by the method of Togagi-Okabe[(Japan J. Pharmac. vol. 18, 9 (1968)] and (c) antisecretory activity, according to Shay et al Gastroenter. 26, 906 (1954).

The cytoprotective ability is a common feature of all the compounds. For example, given subcutaneously, the 6βH-6,9α-oxide is slightly more active (1.5–2 times than the standard PGE$_2$ as a gastric antisecretory agent.

In general, the cytoprotective activity of the 6βH compounds is doubled when an acetylene bond is present in the 13,14-position; it is quadrupled when a 16-alkyl group, usually a methyl, is positioned in the 16(S)-configuration. As an ulcer-preventing substance, the parent 6βH-6,9α-oxide analog is at least equipotent with PGE$_2$ and the following substitutions, 13,14-acetylene bond; 16S, or R methyl; 16S, or R fluoro, highly increase (up to 30 times) the potency ratio.

Furthermore, a significant oral antisecretory activity appears when a methyl group is in the C-15-position of the parent 6βH-6,9α-oxide or in the 16,16-dimethyl compounds, such as the 6βH-6,9α-oxide-16-methyl-16-butoxy-ω-tetranor derivative.

For this purpose the compounds are preferably given by intravenous injection or infusion, subcutaneously or intramuscularly. For intravenous infusion, the doses vary from about 0.1 μg to about 500 μg/kg/body weight/minute. The total daily dose, either by injection or by infusion, is of the order of 0.1 to 20 mg/kg, the exact dose depending on the age, weight and condition of the patient or of the animal being treated and on the route of administration. In addition, the compounds are also useful for treatment of obstructive pulmonary diseases such as bronchial asthma, since they have considerable bronchodilatory activity.

For treatment of the obstructive pulmonary disorders, for example bronchial asthma, the compounds of the invention can be given by different routes; orally in the form of tablets, capsules, coated tablets or in liquid form as drops or syrups; rectally in suppositories; intravenously, intramuscularly or subcutaneously; by inhalation, as aerosols or solutions for the nebulizer; by insufflation, in powdered form.

Doses of the order of 0.01-4 mg/kg can be given from 1 to 4 times a day, with the exact dose depending on the age, weight, and condition of the patient and on the route of administration. For use as an antiasthmatic, the compounds of the invention can be combined with other antiasthmatic agents, such as sympathicomimetic drugs like isoproterenol, ephedrine, etc., xanthine derivatives, such as theophylline and aminophylline, or corticosteriods.

The dosages when used as hypotensive and vasodilatory agents are about the same as those used for the anti-aggregating effects.

As previously stated, the compounds of the invention can be given, either to humans or animals in a variety of dosage forms, e.g., orally in the form of tablets, capsules or liquids; rectally, in the form of suppositories; parenterally, subcutaneously or intramuscularly, with intravenous administration being preferred in emergency situations; by inhalation in the form of aerosols or solutions for nebulizers; in the form of sterile implants for prolonged action; or intravaginally in the form, e.g., of bougies. The pharmaceutical or veterinary compositions containing the compounds of the invention may be prepared in conventional ways and contain conventional carriers and/or diluents.

For example, for intravenous injection or infusion, sterile aqueous isotonic solutions are preferred. For subcutaneous or intramuscular injection, sterile solutions or suspensions in aqueous or non-aqueous media may be used; for tissue implants, a sterile tablet or silicone rubber capsule containing or impregnated with the compound is used.

Conventional carriers or diluents are, for example, water, gelatine, lactose, dextrose, saccharose, mannitol, sorbitol, cellulose, talc, stearic acid, calcium or magnesium stearate, glycol, starch, gum arabic, tragacanth gum, alginic acid or alginates, lecithin, polysorbate, vegetable oils, etc.

For administration by nebulizer, a suspension or a solution of the compound of the invention, preferably in the form of a salt, such as the sodium salt in water, can be used. Alternatively, the pharmaceutical preparation can be in the form of a suspension or of a solution of the compound of the invention in one of the usual liquefied propellants, such as dichlorodifluoromethaneordichlorotetrafluoroethane, administered from a pressurized container such as an aerosol bomb. When the compound is not soluble in the propellant it may be necessary to add a co-solvent, such as ethanol, dipropylene glycol and/or a surfactant to the pharmaceutical formulation.

The invention is illustrated by the following examples, wherein the abbreviations "THF", "DME", "DMSO", "THP", "Et$_2$O" refer to tetrahydrofuran, dimethoxyethane, dimethylsulphoxide, tetrahydropyranyl, and ethyl ether, respectively.

The following examples illustrate but do not limit the present invention.

EXAMPLE 1

To a solution of 1.0 g of dl-5$\beta$-hydroxymethyl-2$\alpha$,4$\alpha$-dihydroxy-cyclopentan-1$\alpha$-acetic acid-$\gamma$-lactone-4-p-phenyl benzoate in 8 ml of benzene/DMSO (75/25) is added with stirring 0.89 g of dicyclohexylcarbodiimide. At room temperature, 1.42 ml of a solution of pyridinium trifluoroacetate is added (prepared from 1 ml of trifluoroacetic acid and 2 ml of pyridine brought to 25 ml with 75/25 benzene/DMSO). After 3 hours 19 ml of benzene is added and the mixture is treated dropwise with an oxalic acid dihydrate solution, 0.3 g in 3.8 ml of water. After approximately 15 minutes of stirring, the mixture is filtered, and the organic phase is washed with water until neutral, concentrated to 2 ml, and then diluted with 5 ml of isopropyl ether. The product is isolated by filtration and crystallized from isopropyl ether to give 0.8 g of dl-5$\beta$-formyl-2$\alpha$,4$\alpha$-dihydroxy-cyclopentan-1$\alpha$-acetic acid-$\gamma$-lactone-4-p-phenylbenzoate, m.p.=129°-131° C. A solution of 800 mg of this in 2.8 ml of anhydrous methanol is treated with 0.62 ml of methyl orthoformate and 18 mg of p-toluenesulfonic acid monohydrate. After 1 hour, 0.01 ml of pyridine is added and the solution is evaporated to dryness. The residue is dissolved in ethyl acetate; it is washed with 1.0 N NaOH and then saturated NaCl until neutral. The solvent is removed at reduced pressure and the residue is crystallized from methanol to give 800 mg of dl-5$\beta$-dimethoxymethyl-2$\alpha$,4$\alpha$-dihydroxy-cyclopentan-1$\alpha$-acetic acid-$\gamma$-lactone-4-p-phenylbenzoate, m.p.=108°-110° C.

60 mg of K$_2$CO$_3$ is added to a solution of this in 5.6 ml of anhydrous methanol. After 4 hours of stirring at room temperature, the solution is filtered; it is then reduced to small volume and acidified with a saturated NaH$_2$PO$_4$ solution. The methanol is removed and the residue taken up in ethyl acetate. This is washed with saturated NaCl until neutral, is dried over anhydrous Na$_2$SO$_4$, is filtered, and evaporated under reduced pressure to give 480 mg of dl-5$\beta$-dimethoxymethyl-2$\alpha$,4$\alpha$-dihydroxy-cyclopentan-1$\alpha$-acetic acid-$\gamma$-lactone.

A solution of this in 4 ml of CH$_2$Cl$_2$ is treated with 0.32 ml of 2,3-dihydropyran and 4.8 mg of p-toluenesulfonic acid. After 4 hours at room temperature, pyridine is added and the solution is evaporated at reduced pressure. The crude reaction product is filtered on 5 g of silica gel, with cyclohexane:ethylether (50:50) as eluent, to give 380 mg of dl-5$\beta$-dimethoxymethyl-2$\alpha$,4$\alpha$-dihydroxy-cyclopentan-1$\alpha$-acetic acid-$\gamma$-lactone-4-tetrahydropyranyl ether. Starting from a 4-ester of 5$\beta$-dimethoxymethyl-2$\alpha$,4$\alpha$-dihydroxy-cyclopentan-1$\alpha$-acetic acid$\gamma$-lactone (for example: 4-p-phenylbenzoate, m.p. 128°-130° C., $[\alpha]_D = -85°$) or from a 4-ester of 5$\alpha$-hydroxymethyl-2$\beta$,4$\beta$-dihydroxy-cyclopentan-1$\beta$-acetic-$\gamma$-lactone (for example: the 4-p-phenylbenzoate, m.p.=127°-129° C., $[\alpha] = +84.5°$), the same procedure was used to prepare the following compounds: 5$\beta$-dimethoxymethyl-2$\alpha$,4$\alpha$-dihydroxy-cyclopentan-1$\alpha$-acetic acid-$\gamma$-lactone-4-tetrahydropyranyl ether and 5$\alpha$-dimethoxymethyl-2$\beta$,4$\beta$-dihydroxy-cyclopentan-1$\beta$-acetic acid-$\gamma$-lactone-4-tetrahydropyranyl ether. If 1,4-diox-2-ene is used instead of 2,3-dihydropyran, the corresponding 4-dioxanyl ether derivatives are obtained.

EXAMPLE 2

A solution of 216 mg of 5$\beta$-dimethoxymethyl-2$\alpha$,4$\alpha$-dihydroxy-cyclopentan-1$\alpha$-acetic acid-$\gamma$-lactone $[\alpha]_D = -16°$, $[\alpha]_{365°} = -48°$ (C=1.0 CHCl$_3$) in 1.6 ml of dimethylformamide is treated with 0.3 ml of triethylamine followed by 291 mg of dimethyl-tert-butylchlorosilane. After one hour, the mixture is diluted with 8.3 ml of water and extracted with hexane. The organic phase is washed with water and dried over $Na_2SO_4$ to give 310 mg of 5β-dimethoxymethyl-2α,4α-dihydroxycyclopentan-1α-acetic acid-γ-lactone-4-dimethyl-tert-butylsilyl ether.

EXAMPLE 3

To a solution of dl-5β-hydroxymethyl-2α,4α-dihydroxycyclopentan-1α-propanoic acid-δ-lactone-4p-phenylbenzoate (1 g) in 8 ml of benzene:DMSO (75:25) is added 0.86 g of dicyclohexyl carbodiimide followed by 1.37 ml of a freshly prepared pyridinium trifluoroacetate (see example 1). After three hours, 18 ml of benzene is added; a solution of 0.29 g of oxalic acid dihydrate in 3.7 ml of water is then added dropwise. After 15 minutes of stirring, the dicyclohexylurea is removed by filtration and the organic phase is washed with water until neutral. This is then reduced to volume to approximately 2 ml and isopropyl ether is added. One obtains 0.793 g of dl-5β-formyl-2α,4α-dihydroxycyclopentan-1α-propionic acid-δ-lactone-4-p-phenylbenzoate.

A solution of 780 mg of this in 2.7 ml of anhydrous methanol is treated with 0.59 ml of methylorthoformate and 17.3 mg of p-toluenesulfonic acid. After approximately one hour, 0.01 ml of pyridine is added and the solution is evaporated to dryness. The residue is taken up in ethyl acetate; the organic phase is washed with 1 N NaOH and then saturated NaCl until neutral. Evaporation to dryness gives 769 mg of dl-5β-dimethoxymethyl-2α,4α-dihydroxycyclopentan-1α-propionic acid-δ-lactone-4p-phenylbenzoate. This is then dissolved in 5.4 ml of anhydrous methanol and 75 mg of $K_2CO_3$ is added. After four hours of stirring at room temperature and filtration, the solution is reduced in volume and acidified with a saturated solution of $NaH_2PO_4$. The methanol is evaporated and the aqueous phase treated with ethyl acetate; the organic phase is then washed with a saturated NaCl solution until neutral, dried over $Na_2SO_4$, and evaporated under vacuum to give crude dl-5β-dimethoxymethyl-2α,4α-dihydroxycyclopentan-1α-propanoic acid-δ-lactone. A solution of this in 4 ml of $CH_2Cl_2$ is treated with 0.3 ml of 2,3-dihydropyran and 4.5 mg of p-toluenesulfonic acid. After four hours at room temperature, 0.01 ml of pyridine is added and the solution is evaporated to dryness. The reaction product is purified on silica gel with cyclohexane: ethyl ether (50:50) as eluent to give 480 mg of dl-5β-dimethoxymethyl-2α,4α-dihydroxycyclopentan-1α-propanoic acid-δ-lactone-4-tetrahydropyranyl ether.

From a 4-ester of 5β-hydroxymethyl-2α,4α-dihydroxycyclopentan-1α-propanoic acid-δ-lactone and from a 4-ester of 5α-hydroxymethyl-2β,4β-dihydroxycyclopentan-1β-propanoic acid-δ-lactone (for example, the 4-p-phenylbenzoate), using the same procedure, the following compounds were obtained:

5β-dimethoxymethyl-2α,4α-dihydroxycyclopentan-1α-propanoic acid-δ-lactone-4-tetrahydropyranyl ether;
5α-dimethoxymethyl-2β,4β-dihydroxycyclopentan-1β-propanoic acid-δ-lactone-4-tetrahydropyranyl ether.

If 1,4-diox-2-ene is used instead of 2,3-dihydropyran, the corresponding 4-dioxanyl ether derivatives are obtained.

EXAMPLE 4

A solution of 1 g of 5β-formyl-2α-hydroxycyclopentan-1α-acetic acid-γ-lactone in 6.5 ml of anhydrous methanol is treated with 1.74 ml of methylorthoformate and 52 mg of p-toluenesulfonic acid. After approximately one hour, 0.04 ml of pyridine is added and the solution is evaporated to dryness. The residue is taken up in ethyl acetate, and the washed with 1 N NaOH and then saturated NaCl until neutral. Evaporation under vacuum gives 1 g of 5β-dimethoxymethyl-2α-hydroxycyclopentan-1α-acetic acid-γ-lactone, [α]=−16°.

The same procedure gave 5β-dimethoxymethyl-2α-hydroxycyclopentan-1α-propionic acid-δ-lactone and its dl derivatives from 5β-formyl-2α-hydroxycyclopentan-1α-propionic acid-δ-lactone.

EXAMPLE 5

To a solution of 960 mg of dl-5β-dimethoxymethyl-2α,4α-dihydroxycyclopentan-1α-acetic acid-γ-lactone-4-tetrahydropyranyl ether in 16 ml of toluene, cooled to −70° C., is added 8.5 ml of a 0.5 N toluene solution of di-iso-butylaluminum hydride, over a 30 minute period. After a further 30 minutes of stirring at −70° C., 10 ml of a 2 M toluene solution of isopropanol is added dropwise. The solution is warmed to 0° C. and treated with 3 ml of a 30% solution of $NaH_2PO_4$. After 1 hour of stirring, 12 g of anhydrous $Na_2SO_4$ is added. Filtration and evaporation of solvent gives 900 mg of dl-5β-dimethoxymethyl-2α,4α-dihydroxycyclopentan-1α-ethanal-γ-lactol-4-tetrahydropyranyl ether.

EXAMPLE 6

Following the procedure of example 5, a solution of 400 mg of 5β-dimethoxymethyl-2α,4α-dihydroxycyclopentan-1α-acetic acid-γ-lactone-4-dimethyl-tert-butylsilyl ether in 11 ml of toluene, cooled to −70° C., is treated dropwise with 5.9 ml of a 0.5 N toluene solution of di-iso-butylaluminum hydride to give 0.43 g of 5β-dimethoxymethyl-2α,4α-dihydroxycyclopentan-1α-ethanal-γ-lactol-4-dimethyl-tert-butylsilyl ether.

EXAMPLE 7

Under a nitrogen atmosphere, a solution of 628 mg of 5β-dimethoxymethyl-2α,4α-dihydroxycyclopentan-1α-propanoic acid-δ-lactone-4tetrahydropyranyl ether in 11 ml of toluene, cooled to −70° C., is treated dropwise with 5.9 ml of a 0.5 M toluene solution of di-iso-butylaluminum hydride. After 30 minutes at −70° C., 10.9 ml of a 2 M toluene solution of isopropanol is added dropwise. The temperature is allowed to rise to 0° C. and 2 ml of 30% $NaH_2PO_4$ is added. After one hour of stirring, 8.3 g of anhydrous $Na_2SO_4$ is added and the mixture is filtered. Evaporation of the organic phase under vacuum gives 620 mg of 5β-dimethoxymethyl-2α,4α-dihydroxycyclopentan-1α-propanal-δ-lactol-4-tetrahydropyranyl ether.

EXAMPLE 8

Using one of the procedures outlined in examples 5, 6 and 7, a 4-acetal (4-tetrahydropyranyl ether; 4-dioxanyl ether) and a 4-dimethylbutylsilyl ether of the following compounds are prepared:
5β-dimethoxymethyl-2α,4α-dihydroxycyclopentan-1α-ethanal-γ-lactol, in its dl and optically active form (or nat-);
5α-dimethoxymethyl-2β,4β-dihydroxycyclopentan-1β-ethanal-γ-lactol (or ent- form);
5β-dimethoxymethyl-2α,4α-dihydroxycyclopentan-1α-propanal-δ-lactol, in its dl and optically active form (or nat-);

5β-dimethoxymethyl-2β,4β-dihydroxycyclopentan-1β-propanal-δ-lactol (or ent- form).

EXAMPLE 9

0.29 ml of absolute ethanol in 3.5 ml of toluene is added dropwise to a solution of $5 \times 10^{-3}$ mol of sodium (2-methoxyethoxy)aluminum hydride (1.4 ml of a 70% benzene solution diluted with 5 ml of toluene) cooled to 0° C. 8.2 ml of the alanate solution so prepared is added, at −30° C., to 0.98 g of dl-5β-benzyloxymethyl-2α-hydroxycyclopentan-1α-propionic acid-δ-lactone in 22 ml of toluene. After 45 minutes, excess reagent is quenched with 6 ml of a 0.5 M toluene solution of isopropanol. The mixture is warmed to 0° C., 4 ml of 30% NaH$_2$PO$_4$ is added, and the resulting mixture is stirred for 2 hours. The inorganic salts are removed by filtration and the solution is evaporated to dryness to give 0.94 g of dl-5β-benzyloxymethyl-2α-hydroxycyclopentan-1α-propanal-δ-lactol.

Using the procedure reported above, or one of those from examples 4 to 7, the following compounds were prepared from their corresponding γ-lactones:
5β-benzyloxymethyl-2α-hydroxycyclopentan-1α-ethanal-γ-lactol;
5β-benzyloxymethyl-2α-hydroxycyclopentan-1α-propanal-δ-lactol;
5β-dimethoxymethyl-2α-hydroxycyclopentan-1α-ethanal-γ-lactol;
5β-dimethoxymethyl-2α-hydroxycyclopentan-1α-propanal-δlactol.

EXAMPLE 10

With stirring and external cooling to maintain a reaction temperature of 20°–22° C., a solution of 1.05 g of potassium tert-butylate in 10 ml of DMSO is added dropwise to a solution of 1.8 g of 4-carboxybutyl-triphenylphosphonium bromide and 0.38 g of 5β-dimethoxymethyl-2α,4α-dihydroxycyclopentan-1α-ethanal-γ-lactol-4-tetrahydropyranyl ether. After the addition, the mixture is held at room temperature for 1 hour and then diluted with 16 ml of ice/water. The aqueous phase is extracted with ether (5×8 ml) and ether:benzene (70:30, 5×6 ml); the organic layers, after re-extraction with 0.5 M NaOH (2×10 ml), are discarded. The combined alkaline aqueous phase is acidified to pH 4.8 with 30% NaH$_2$PO$_4$ and then extracted with ethyl ether:pentane (1:1, 5×15 ml); from the combined organic phases, after drying over Na$_2$SO$_4$ and solvent removal, one obtains 0.45 g of 5-cis-7-(2'α,4'α-dihydroxy-5'β-dimethoxymethylcyclopentan-1'α-yl)-hept-5-enoic acid-4'-tetrahydropyranyl ether. This in turn is converted to the corresponding methyl ester upon treatment with diazomethane in ether. An analytic sample is prepared by adsorbing 100 mg of the crude product on 1 g of silica gel and eluting with benzene:ethyl ether (85:15). N.M.R.:

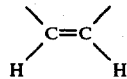

5.46 p.p.m. multiplet.

EXAMPLE 11

In an anhydrous nitrogen atmosphere, a suspension of 0.39 g of a 75% oil dispersion of NaH in DMSO (13.5 ml) is heated to 60°–65° C. for 3½ hours; after cooling to room temperature and while maintaining the reaction mixture at 20°–22° C., the following are added, in order: 2.66 g of 3-carboxypropyltriphenylphosphonium bromide in 6 ml of DMSO and 0;6 g of 5β-dimethoxymethyl-2α,4α-dihydroxycyclopentan-1α-propanal-δ-lactol-4-tetrahydropyranyl ether in 3 ml of DMSO. The mixture is stirred for 3 hours, and then diluted with 35 ml of water. The aqueous phase is extracted with ethyl ether (5×12 ml) and ethyl ether:benzene (70:30, 7×12 ml); the combined organic extract, after re-extraction with 0.5 N NaOH (2×15 ml), is discarded. The combined alkaline aqueous extract is acidified to pH 4.3 with 30% aqueous NaH$_2$PO$_4$ and extracted with ethyl ether:pentane (1:1) to give, after washing until neutral, drying over Na$_2$SO$_4$, and removal of the solvent, 0.71 g of 4-cis-7-(2'α,4'α-dihydroxy-5'β-dimethoxymethyl-cyclopent-1'α-yl)-hept-4-enoic acid. Treatment with diazomethane affords the corresponding methyl ester.

EXAMPLE 12

The methyl esters of the following acids were prepared from lactols made according to the procedures in examples 4 to 8 by treatment with a Wittig reagent (prepared from 4-carboxybutyl-triphenylphosphonium bromide or 3-carboxypropyltriphenylphosphonium bromide) and successive esterification with diazomethane, in their optically active or dl forms:
4-cis-7-(2'α-hydroxy-5'β-benzyloxymethylcyclopent-1'α-yl)-hept-4-enoic;
4-cis-7-(2'α-hydroxy-5'β-dimethoxymethyl-cyclopent-1'α-yl)-hept-4-enoic;
5-cis-7-(2'α-hydroxy-5'β-dimethoxymethyl-cyclopent-1'α-yl)-hept-5-enoic;
5-cis-7-(2'α-hydroxy-5'β-benzyloxymethyl-cyclopent-1'α-yl)-hept-5-enoic;
5-cis-7-(2'α,4'α-dihydroxy-5'β-dimethoxymethyl-cyclopent-1'α-yl)-hept-5-enoic and its 4'-dioxanyl, tetrahydropyranil and dimethyl-tert-butylsilyl)-ethers;
4-cis-7-(2'α,4'α-dihydroxy-5'β-dimethoxymethyl-cyclopent-1'α-yl)-hept-4-enoic and its 4'-(dioxanyl, tetrahydropyranyl and dimethyl-tert-butylsilyl)-ethers;
4-cis-6-(2'α,4'α-dihydroxy-5'β-dimethoxymethyl-cyclopent-1'α-yl)-hex-4-enoic and its 4'-(tetrahydropyranylether;
5-cis-8-(2'α,4'α-dihydroxy-5'β-dimethoxymethyl-cyclopent-1'α-yl)-oct-5-enoic and its 4'-tetrahydropyranylether.

EXAMPLE 13

A solution of 1.06 g of the methyl ester of 5-cis-7-(2'α,4'α-dihydroxy-5'β-dimethoxymethyl-cyclopent-1'α-yl)-hept-5-enoic acid-4'-tetrahydropyranyl ether in 5 ml of methanol is added to 0.84 g of mercuric acetate in methanol. After 30 minutes at room temperature, a solution of 250 mg of sodium borohydride in 2 ml of water is added with stirring and external cooling. After 20 minutes of stirring, the mixture is acidified to pH 6.5 with aqueous monosodium phosphate, the methanol is removed under vacuum, and the residue is taken up in water/ethyl ether. The organic phase, upon removal of the solvent, affords 1.02 g of 5-(6'-exo-dimethoxymethyl-7'-endo-hydroxy-2'-oxa-bicyclo[3.3.0]octan-3'ƒ-yl)-pentanoic acid methyl ester-7'-tetrahydropyranyl ether.

EXAMPLE 14

A solution of 1.59 g of 4-cis-7-(2'α,4'α-dihydroxy-5'β-dimethoxymethyl-cyclopent-1'α-yl)-hept-4-enoic methyl ester-4'-tetrahydropyranyl ether in 6 ml of THF is added to a solution of 1.26 g of mercuric acetate in 4 ml of water diluted with 4 ml of THF. The mixture is stirred for 1½ hours until precipitation is complete. 180 mg of sodium borohydride (in 2.5 ml of water) is then added and the resulting mixture is stirred for 30 minutes. The solution is decanted from the precipitate, which is then washed with THF. The aqueous/organic decanted solution is concentrated under reduced pressure and the residue extracted with ethyl acetate. The combined organic extract, after washing with water until neutral, affords upon removal of the solvent 0.98 g of 4-(7'-exo-dimethoxymethyl-8'-endo-hydroxy-2'-oxa-bicyclo[3.4.0]nonan-3' -yl)-butanoic acid methyl ester-8'-tetrahydropyranyl ether.

EXAMPLE 15

Starting from the esters prepared as described in examples 9 to 11, by reaction with a mercuric salt and subsequent reductive demercuration as described in the procedures in examples 13 and 14, the following bicyclic derivatives are obtained:

5-(6'-exo-benzyloxymethyl-2'-oxa-bicyclo[3.3.0]octan-3' -yl)-pentanoic acid methyl ester;
5-(6'-exo-dimethoxymethyl-2'-oxa-bicyclo[3.3.0]octan-3' -yl)-pentanoic acid methyl ester;
4-(7'-exo-benzyloxymethyl-2'-oxa-bicyclo[3.4.0]nonan-3' -yl)-butanoic acid methyl ester;
4-(7'-exo-dimethoxymethyl-2'-oxa-bicyclo[3.4.0]nonan-3' -yl)-butanoic acid methyl ester;
a 7'-acetal ether (tetrahydropyranyl ether, dioxanyl ether), and a 7'-dimethyl-tert-butylsilyl ether of 5-(6'-exo-dimethoxy methyl-7'-endo-hydroxy-2'-oxa-bicyclo[3.3.0]octan-3' -yl)-pentanoic acid methyl ester;
an 8'-acetal ether (tetrahydropyranyl ether, dioxanyl ether) and an 8'-dimethyl-tert-butylsilyl ether of 4-(7'-exo-dimethoxymethyl-8'-endo-hydroxy-2'-oxa-bicyclo[3.4.0]nonan-3' -yl)-butanoic acid methyl ester,
4-(6'-exo-dimethoxymethyl-7'-endo-hydroxy-2'-oxa-bicyclo[3.3.0]octan-3' -yl)-butanoic acid methyl ester-7'-tetrahydropyranyl ether;
5-(7'-exo-dimethoxymethyl-8'-endo-hydroxy-2'-oxa-bicyclo[3.4.0]nonan-3' -yl)-pentanoic acid methyl ester-8'-tetrahydropyranyl ether.

All these compounds are obtained in the d,l-, nat- and ent-forms.

EXAMPLE 16

A solution of 0.48 g of bromine in 5 ml of methylene chloride is added dropwise, with stirring, to a solution of 0.27 g of pyridine and 1.2 g of 5-cis-7-(2'α,4'α-dihydroxy-5'β-dimethoxymethyl-cyclopent-1'α-yl)-hept-5-enoic acid methyl ester-4'-tetrahydropyranyl ether in 6 ml of methylene chloride, cooled to 0° C. Stirring is continued for ten minutes following the addition. The organic phase is washed with 5 ml of a pH 7 buffer solution 10% in sodium thio sulfate and then with water until neutral. After drying over $Na_2SO_4$, removal of the solvent affords 1.38 g of 5-bromo-5-(6'-exo-dimethoxymethyl-7'-endo-hydroxy-2'-oxa-bicyclo[3.3.0]octan-3' -yl)-pentanoic acid methyl ester-7'-tetrahydropyranyl ether.

EXAMPLE 17

1.24 g of N-iodosuccinimide is added to a solution of 2 g of 5-cis-7-(2'α,4'α-dihydroxy-5'β-dimethoxymethyl-cyclo pent-1'α-yl)-hept-5-enoic acid methyl ester-4'-tetrahydropyranyl ether in 15 ml of carbon tetrachloride. The mixture is stirred for 3 hours and 30 ml of ethyl ether is added. The organic phase is washed with 1 N $Na_2S_2O_3$ and then with water until neutral. Removal of the solvent affords 2.48 g of 5-iodo-5'-(6'-exo-dimethoxymethyl-7'-endo-hydroxy-2'-oxa-bicyclo[3.3.0]octan-3' -yl)-pentanoic acid methyl ester-7'-tetrahydropyranyl ether.

EXAMPLE 18

422 mg of N-bromosuccinimide is added with stirring to a solution of 0.78 g of 4-cis-7-(2'α,4'α-dihydroxy-5'β-dimethoxy methyl-cyclopent-1'α-yl)-hept-4-enoic acid methyl ester-4-tetrahydropyranyl ether in 11 ml of $CCl_4$. After four hours of stirring, ethyl ether is added; the solution is then washed with water, 1 N $Na_2S_2O_3$, and water until neutral. Evaporation to dryness gives 0.98 g of 4-bromo-4-(7'-exo-dimethoxymethyl-8'-endo-hydroxy-2'-oxa-bicyclo[3.4.0]nonan-3' -yl)-butanoic acid methyl ester-8'-tetrahydropyranyl ether.

EXAMPLE 19

To a suspension of 0.25 g of dry $CaCO_3$ in a solution of 346 mg of 5-cis-7-(2'α-hydroxy-5'β-benzyloxymethyl-cyclopent-1'α-yl)-hept-5-enoic acid methyl ester in 10 ml of $CCl_4$ cooled to 0°–5° C. is added with stirring a solution of 75 mg of chlorine in 3 ml of $CCl_4$. After stirring for 2 hours, the inorganic salts are removed by filtration. The solution is washed with a 7% aqueous solution of KI and $Na_2S_2O_3$ and then with water until neutral. The residue upon evaporation to dryness is adsorbed on silica gel and eluted with cyclohexane:ethyl ether (80:20) to give 0.27 g of 5-chloro-5-(6'-exo-benzyloxymethyl-2'-oxa-bicyclo[3.3.0]octan-3' -yl)-pentanoic acid methyl ester.

EXAMPLE 20

A solution of 0.39 g of 5-cis-7-(2'α,4'α-dihydroxy-5'β-dimethoxymethyl-cyclopent-1'α-yl)-hept-5-enoic acid methyl ester-4'-dioxanyl ether and 98 mg of pyridine in 10 ml of dichloromethane is cooled to −40° C. A solution of 81 mg of chlorine in 6 ml of $CH_2Cl_2$ is then added over a period of 30 minutes. After 10 minutes of stirring, the mixture is heated to room temperature. The organic phase is washed with a 7% solution of KI and $Na_2S_2O_3$ and then with water until neutral. Removal of the solvent affords 0.39 g of 5-chloro-5-(6'-exo-dimethoxymethyl-7'-endo-hydroxy-2'-oxa-bicyclo[3.3.0]octan-3' -yl)-pentanoic acid methyl ester-4'-dioxanyl ether.

EXAMPLE 21

280 mg of iodine in $CCl_4$ is added to a solution of 0.39 g of 4-cis-7-(2'α,4'α-dihydroxy-5β-dimethoxymethyl-cyclopent-1'α-yl)-hept-4-enoic acid methyl ester-4'-tetrahydropyranyl ether and 82 mg of pyridine in 10 ml of $CCl_4$. Stirring is continued until the color disappears; 30 ml of ethyl ether is then added. The organic phase is washed with water, then a solution 7% inKI and $Na_2S_2O_3$, and then water until neutral. Removal of the solvent affords 0.48 g of 4-iodo-4-(7'-exo-dimethoxymethyl-8'-endo-hydroxy-2'-oxa-bicyclo[3.4.0]nonan-3' -yl)-butanoic acid methyl ester-8'-tetahydropyranyl ether.

EXAMPLE 22

To a solution of 0.34 g of 5-cis-7-(2'α-hydroxy-5'β-benzyloxymethyl-cyclopent-1'α-yl)-hept-5-enoic acid methyl ester in 6 ml of methanol is added with stirring a solution of 0.325 g of mercuric acetate in water:methanol (1:9, 6 ml). The mixture is stirred for 15 minutes, reduced to 3 ml under vacuum, and then added to 5 ml of a saturated solution of NaCl in water. The precipitate is then extracted with methylene chloride. The organic phase is washed with water and evaporated to dryness to give 0.52 g of crude 5-chloromercurio-5-(6'-exo-benzyloxymethyl-2'-oxa-bicyclo[3.3.0]octan-3' ʃ-yl)-pentanoic acid methyl ester. A solution of this in methylene chloride (10 ml) is treated with 80 mg of pyridine in 2 ml of $CH_2Cl_2$ and then dropwise with stirring with a solution of 150 mg of $Br_2$ in $CH_2Cl_2$. After 20 minutes of stirring at room temperature, the organic phase is washed with water, then 7% KI and $Na_2S_2O_3$, and water until neutral. Evaporation to dryness gives 0.34 g of 5-bromo-5-(6'-exo-benzyloxymethyl-2'-oxa-bicyclo[3.3.0]octan-3' ʃ-yl)-pentanoic acid methyl ester. Mass spectrum $M^+$424,426 m/e $M^+$-HBr 344 m/e $M^+$-$CHBr(CH_2)_3CO_2CH_3$=231 m/e.

EXAMPLE 23

10.5 mg of p-toluenesulfonic acid monohydrate is added to a solution of 0.26 g of 5-iodo-5-(6'-exo-dimethoxymethyl-7'-endo-hydroxy-2'-oxa-bicyclo∂3.3.0]octan-3' ʃ-yl)-pentanoic acid methyl ester-7'-tetrahydropyranyl ether and the resulting mixture is left ar room temperature for 30 minutes. 10 mg of pyridine is then added and the solution is evaporated to dryness. The residue is taken up in ethyl ether/water. After drying over $Na_2SO_4$, the organic phase gives upon solvent evaporation 0.23 g of crude 5-iodo-5-(6'exo-dimethoxymethyl-7'-endo-hydroxy-2'-oxa-bicyclo[3.3.-0]octan-3' ʃ-yl)-pentanoic acid methyl ester. Separation by chromatography on silica gel with methylene chloride: ethyl ether (75:25) as eluent affords 84 mg of 5-iodo-5-(6'-exo-dimethoxymethyl-7'-endo-hydroxy-2'-oxa-bicyclo[3.3.0]octan-3'-endo-yl)-pentanoic acid methyl ester and 55 mg of the 3 exo isomer.

Referring the spectrometric data, the prostaglandin numbering will be used; thus the above diastereoisomers can be named as follows: the endo diastereoisomer: 6βH-6,9α-oxide-11α-hydroxy-12β-dimethoxy-formylacetal-ω(20→13)tetranor-prostanoic acid methyl ester and the exo diastereoisomer 6°H-6,9α-oxide-11α-hydroxy-12β-dimethoxy-formylacetal-ω(20→13)tetranor-prostanoic acid methyl ester.

Analytical data:

endo diastereoisomer: TLC more polar-one spot

Mass spectrum (m/e; % intensity fragment): 442 0.002 $M^+$; 412 4 $M^+$—$CH_2O$, 315/314 3 $M^+$-iodine/HI 283 11 315-$CH_3OH$, 75 100 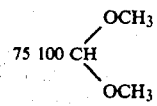

N.M.R. (solvent $CDCl_3$, TMS internal standard) p.p.m.: 3.49 and 3.52 s, 3H/3H,

3.64 s, 3H, $CO_2\underline{CH_3}$; 4.00 m, 3H (protons at $C_5$, $C_9$, $C_{11}$); 4.29 d, 1H,

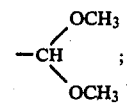

4.60 m, 1H, <u>6βH</u>

$^{13}$C—MR (at 20 MHz in $C_6D_6$ solution TMS int. standard) p.p.m. 172.9, 36.5, 33.1, 25.6, 41.8, 81.0, 38.1, 55.5, 83.1, 41.5, 74.2, 44.6, 108.0, 54.2, 54.1, 51.0.

exo diastereoisomer: TLC less polar-one spot

Mass spectrum: 442 0.01 $M^+$, 366 3 $M^+$+$CH_2CH(OCH_3)_2$, 315 4 $M^+$-I; 283 10 $M^+$-I—$CH_3OH$; 75 100 $CH(OCH_3)_2^+$ N.M.R.: p.p.m. 3.34 and 3.37 3H/3H s

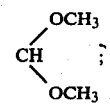

3.5 and 4.1 m 1 H and 2 M protons at $C_5$, $C_9$, $C_{11}$ uncertain assignment, 3.65, s3H, $CO_2CH_3$; 4.21, d1H

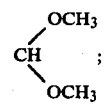

4.35 m, 1H, 6αH $^{13}$CMR; p.p.m. 173.0, 37.0, 33.1, 25.5, 40.1, 84.4, 39.7, 57.2, 83.7, 40.5, 75.9, 44.0, 107.3, 54.0, 53.8, 51.1.

EXAMPLE 24

A solution of 980 mg of 4-bromo-4-(7'-exo-dimethoxy methyl-8'-endo-hydroxy-2'-oxa-bicyclo[3.4.0]nonan-3'ʃ -yl)-butanoic acid methyl ester-8'-tetrahydropyranyl ether in 6 ml of anhydrous methanol is treated at room temperature for 30 minutes with 48 mg of p-toluenesulfonic acid. 2% aqueous $NaHCO_3$ is added and the mixture is extracted with ethyl ether. From the organic phase, after washing until neutral and evaporation of the solvent, one obtains 0.68 g of a crude product which after purification on silica gel with methylene chloride: ethyl ether (80:20) as eluent affords 0.30 g of 4-bromo-4-(7'-exo-dimethoxymethyl-8'-endo-hydroxy-2'-oxa-bicyclo[3.4.0]nonan-3'-exo-yl)-butanoic acid methyl ester and 0.29 g of the 3'-endo isomer.

EXAMPLE 25

Starting from acids prepared according to the procedure of example 11 and performing their halocyclization as described in one of the examples 16 to 22, the following halobicyclic compounds are prepared:

5-chloro-5-(6'-exo-dimethoxymethyl-7'-endo-hydroxy-2'-oxa-bicyclo[3.3.0]octan-3' ʃ -yl)-pentanoic acid methyl ester-7'-tetrahydropyranyl ether (and 7'-dioxanyl ether and 7'-dimethylbutylsilyl ether);

4-chloro-4-(7'-exo-dimethoxymethyl-8'-endo-hydroxy-2'-oxa-bicyclo[3.4.0]nonan-3'ƒ -yl)-butanoic acid methyl ester-8'-tetrahydropyranyl ether (and 8'-dioxanyl and 8'-dimethylbutyl silyl ethers);

5-chloro-5-(6'-exo-dimethoxymethyl-2'-oxa-bicyclo[3.3.0]octan-3'ƒ -yl)-pentanoic acid methyl ester;

5-chloro-5-(6'-exo-benzyloxymethyl-2'-oxa-bicyclo[3.3.0]octan-3'ƒ -yl)-pentanoic acid methyl ester;

4-chloro-4-(7'-dimethoxymethyl-2'-oxa-bicyclo[3.4.0]nonan-3'ƒ -yl)-butanoic acid methyl ester;

4-chloro-4-(7'-exo-benzyloxymethyl-2'-oxa-bicyclo[3.4.0]nonan-3'ƒ -yl)-butanoic acid methyl ester;

5-bromo-5-(6'-exo-dimethoxymethyl-7'-endo-hydroxy-2'-oxa-bicyclo[3.3.0]octan-3'ƒ -yl)-pentanoic acid methyl ester-7'-tetrahydropyranyl ether (and 7'-dioxanyl and 7'-dimethylbutyl silyl ethers);

4-bromo-4-(7'-exo-dimethoxymethyl-8'-endo-hydroxy-2'-oxa-bicyclo[3.4.0]nonan-3'ƒ -yl)-butanoic acid methyl ester-8'-tetrahydropyranyl ether (and 8'-dioxanyl and 8'-dimethylbutyl silyl ethers);

5-bromo-5-(6'-exo-dimethoxymethyl-2'-oxa-bicyclo[3.3.0]octan-3'ƒ -yl)-pentanoic acid methyl ester;

5-bromo-5-6'-exo-benzyloxymethyl-2'-oxa-bicyclo[3.3.0]octan-3'ƒ -yl)-pentanoic acid methyl ester;

4-bromo-4-(7'-exo-dimethoxymethyl-2'-oxa-bicyclo[3.4.0]nonan-3'-yl)-butanoic acid methyl ester;

4-bromo-4-(7'-exo-benzyloxymethyl-2'-oxa-bicyclo[3.4.0]-nonan-3'ƒ -yl)-butanoic acid-methyl ester;

5-iodo-5-(6'-exo-dimethoxymethyl-7'-endo-hydroxu-2'-oxa-bicyclo[3.3.0]octan-3'ƒ -yl)-pentanoic acid methyl ester-7'-tetrahydropyranyl ether (and 7'-dioxanyl and 7'-dimethylbutylsilyl ethers);

4-iodo-4-(7'-exo-dimethoxymethyl-8'-endo-hydroxy-2'-oxa-bicyclo[3.4.0]nonan-3'ƒ -yl)-butanoic acid methyl ester-8'-tetrahydropyranyl ether (and 8'-dioxanyl and 8'-dimethylbutyl silyl ethers);

5-iodo-5-(6'-exo-dimethoxymethyl-2'-oxa-bicyclo[3.3.0]octan-3'ƒ -yl)-pentanoic acid methyl ester;

5-iodo-5-(6'-exobenzyloxymethyl-2'-oxa-bicyclo[3.3.0]octan-3'ƒ -yl)-pentanoic acid methyl ester;

4-iodo-4-(7'-exo-benzyloxymethyl-2'-oxa-bicyclo[3.4.0]nonan-3'ƒ -yl)-butanoic acid methyl ester;

4-iodo-4-(7'-exo-dimethoxymethyl-2'-oxa-bicyclo[3.4.0]nonan-3'ƒ -yl)-butanoic acid methyl ester.

EXAMPLE 26

Selective de-acetalization or de-silylization of the ethers described in example 25, according to the procedure in examples 23 and 24 affords the 3' -oxiran-hydroxide-formyl acetales derivatives, which give the following upon separation of isomers:

5-chloro-5-(6'-exo-dimethoxymethyl-7'-endo-hydroxy-2'-oxa-bicyclo[3.3.0]octan-3'ƒ -yl)-pentanoic acid methyl ester, and its individual 3'-exo and 3'-endo isomers;

4-chloro-4-(7'-exo-dimethoxymethyl-8'-endo-hydroxy-2'-oxa-bicyclo[3.4.0]nonan-3'ƒ -yl)-butanoic acid methyl ester, and its individual 3'-exo and 3'-endo isomers;

5-bromo-5-(6'-exo-dimethoxymethyl-7'-endo-hydroxy-2'-oxa-bicyclo[3.3.0]octan-3'ƒ -yl)-pentanoic acid methyl ester, and its individual 3'-exo and 3'-endo isomers;

endo isomer: TLC an SiO$_2$ more polar one spot N.M.R.: (CDCl$_3$) p.p.m. 3.4 d,6H,

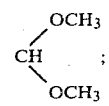

3.65, s,3H  CO$_2$CH$_3$  4.00  m,4H  (protons at C$_4$,C$_5$,C$_9$,C$_{11}$); 4.17 d,1,

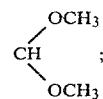

4.5 m,1H, 6βH

—CMR: 173.0, 35.0, 33.3, 23.6, 59.4, 80.6, 36.4, 55.6, 83.3, 41.6, 74.3, 44.5, 108.0, 54.4, 54.2, 51.1 exo isomer: TLC on SiO$_2$ less polar isomer one spot N.M.R.: (CDCl$_3$) p.p.m.: 3.37 d,

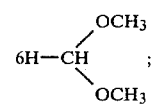

3.66 s,3H,CO$_2$CH$_3$ 4.00 m,4H, protons at C$_4$,C$_5$,C$_9$,C$_{11}$;

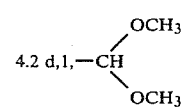

4.32 m,1H, 6αH

—CMR: 173.0, 35.5, 33.3, 23.6, 57.7, 84.2, 38.2, 57.9; 83.6, 40.5, 76.0, 43.9, 107.2, 53.8, 53.8, 51.0.

4-bromo-4-(7'-exo-dimethoxymethyl-8'-endo-hydroxy-2'-oxa-bicyclo[3.4.0]nonan-3'ƒ -yl)-butanoic acid methyl ester and its individual isomers, 3'-exo and 3'-endo;

5-iodo-5-(6'-exo-dimethoxymethyl-7'-endo-hydroxy-2'-oxa-bicyclo[3.3.0]octan-3'ƒ -yl)-pentanoic acid methyl ester and its individual 3'-exo and 3'-endo isomers;

4-iodo-4-(7'-exo-dimethoxymethyl-8'-endo-hydroxy-2'-oxa-bicyclo[3.4.0]nonan-3'ƒ -yl)-butanoic acid methyl ester and its individual 3'-exo and 3'-endo isomers.

EXAMPLE 27

With stirring under nitrogen, a benzene solution (30 ml) of 2.8 g of 5-iodo-5-(6'-exo-dimethoxymethyl-7'-endo-hydroxy-2'-oxa-bicyclo[3.3.0]octan-3'ƒ -yl)-pentanoic acid methyl ester-7'-tetrahydropyranyl ether is treated with a solution of 2.8 g of tributyltin hydride in 8 ml of benzene. The mixture is held at 55° C. for 8 hours and then overnight at room temperature. The benzene layer is washed with 2×10 ml of a 5% NaHCO$_3$ solution and then with water until neutral. The residue upon solvent evaporation is adsorbed on 10 g of silica gel and eluted with benzene and benzene:ethyl ether (85:15) to give 1.94 g of 5-(6'-exo-dimethoxymethyl-7'-endo-hydroxy-2'-oxa-bicyclo[3.3.0]octan-3'ƒ -yl)-pentanoic acid methyl ester-7'-tetrahydropyranyl ether.

EXAMPLE 28

60 mg of p-toluenesulfonic acid is added to a solution of 1.98 g of 5-(6'-exo-dimethoxymethyl-7'-endo-hydroxy-2'-oxa-bicyclo[3.3.0]octan-3'-yl)-pentanoic acid methyl ester-7'-tetrahydropyranyl ether in 10 ml of anhydrous methanol. After 30 minutes at room temperature, this is added to 20 ml of 20% aqueous $NaHCO_3$. The mixture is extracted with ethyl ether; the combined ether extract, after drying over $Na_2SO_4$, is evaporated to dryness. The residue is adsorbed on 100 g of silica gel and eluted with methylene chloride:ethyl ether (94:6) to give 0.64 g of 5-(6'-exo-dimethoxymethyl-7'-endo-hydroxy-2'-oxa-bicyclo[3.3.0]octan-3'-exo-yl)-pentanoic acid methyl ester, 0.52 g of the 3'-endo isomer and 0.12 g of the 3'-yl.

N.M.R. ($CDCl_3$) endo isomer 4.6 p.p.m. m,1H 6$\beta$H, T.L.C. more polar; exo isomer 4.3 p.p.m. m,1H 6$\alpha$H, T.L.C. less polar.

0.32 g of the 3'-endo isomer is dissolved in pyridine (0.8 ml) and treated for 8 hours at room temperature with 0.3 ml of acetic anhydride. The mixture is then poured into ice/water, and, after acidifying to pH 4.2, is extracted with ethyl ether. The combined extract, after washing until neutral, is evaporated to give 0.315 g of 5-(6'-exo-dimethoxy methyl-7'-endo-hydroxy-2'-oxa-bicyclo[3.3.0]octan-3'-exo-yl)pentanoic acid methyl ester-7'-acetate.

EXAMPLE 29

A solution of 1.32 g of 4-(7'-exo-dimethoxymethyl-8'-endo-hydroxy-2'-oxa-bicyclo[3.4.0]nonan-3'-yl)-butanoic acid methyl ester-8'-tert butylmethylsilyl either in 10 ml of anhydrous methanol is treated with 55 mg of p-toluenesulfonic acid for 2 hours at room temperature. 0.1 ml of pyridine is added, the solvent is removed under vacuum, and the residue is taken up in water-/ethyl ether. The organic phase gives, upon removal of the solvent, 1.1 g of the crude 8'-hydroxy-3'-yl derivative. Chromatography of this on silica gel with benzene:ethyl ether (80:20) as eluent separates this into 4-(7'-exo-dimethoxymethyl-8'-endo-hydroxy-2'-oxabicyclo[3.4.0]nonan-3'-endo-yl)-butanoic acid methyl ester (0.42 g) and the 3'-exo-yl isomer (0.34 g).

EXAMPLE 30

Using the procedure in examples 28 and 29, methanolysis of the ethers (acetal or silyl) described in example 15 gives the corresponding free alcohols.

EXAMPLE 31

Upon acetylation with pyridine (0.6 ml) and acetic anhydride (0.3 ml) 0.2 g of 5-iodo-5-(6'-exo-dimethoxymethyl-7'-endo-hydroxy-2'-oxa-bicyclo[3.3.0]octan-3'-endo-yl)-pentanoic acid methyl ester gives 0.21 g of the corresponding 7'-acetoxy derivative.

N.M.R. ($CDCl_3$) p.p.m.: 2.03 s, 3H OCO$\underline{CH}_3$; 3.36–3.40 s,s 3H/3H

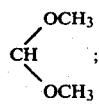

3.66 s 3H CO$_2\underline{CH}_3$; 4.00 m 2H protons at $C_5,C_9$; 4.27 d 1H

4.6 m 1H 6$\beta$H 5.0 m 1H proton at $C_{11}$

[The spectrometric data for the 6$\alpha$H isomer acetate are respectively the following 2.03; 3.34–338, 3.66 s+m 4H CO$_2\underline{CH}_3$ and one of $C_5,C_9$ protons 4.1 m 1H other of $C_5,C_9$ protons 4.2, 4.4 m 1H 6$\underline{\alpha H}$, 5.1]. A solution of the 5-iodo-3'-endo-acetate in benzene (5 ml) is treated with 0.4 g of tributyltin hydride for 10 hours at 50° C. After the benzene phase is washed with 5% $NaHCO_3$ and water, evaporation of the solvent and purification on silica gel (10 g) with a benzene:ethyl ether (80:20) eluent afford 0.105 g of 5-(6'-exo-dimethoxymethyl-7'-endo-hydroxy-2'-oxa-bicyclo[3.3.0] octan-3'-endo-yl)-pentanoic acid methyl ester-7'-acetate, identical in all respects with a sample prepared by the procedure in example 28.

EXAMPLE 32

Using the procedure of examples 27 and 31, the reduction with tributyltin hydride of one of the halo-derivatives synthesized in examples 16–26 gives the corresponding derivative in which halogen is replaced by hydrogen. These are identical in every way with the compounds prepared according to the procedures of examples 15, 28, 29 and 30.

EXAMPLE 33

5.4 mg of hydroquinone and a solution of 1.63 g of oxalic acid in 48 ml of water are added to a solution of 4 g of 5-(6'-exo-dimethoxymethyl-7'-endo-hydroxy-2'-bicyclo[3.3.0] octan-3'-yl)-pentanoic acid methyl ester in 180 ml of acetone. After 12 hours at 40° C., the acetone is removed at reduced pressure and the mixture is extracted with ethyl acetate (3×25 ml). The combined organic extract is washed until neutral with a 10% ammonium sulfate solution and dried over $Na_2SO_4$. Removal of the solvent affords 3.21 g of 5-(6'-exoformyl-7'-endo-hydroxy-2'-oxa-bicyclo[3.3.0]octan-3'-yl) - pentanoic acid methyl ester. The 6'-exo-formyl-3'-endo and the 6'-exo-formyl-3'-exo derivatives are prepared from the corresponding individual isomers.

EXAMPLE 34

Using the procedure of example 33, starting from the corresponding bicyclo[3.3.0]octan-6'-exo-dimethoxymethyl and bicyclo[3.4.0]nonan-7'-exo-dimethoxymethyl derivatives, the following compounds are prepared, either as individual 3'-exo and 3'endo or 3' isomers:

5-(6'-exo-formyl-2'-oxa-bicyclo[3.3.0]octan-3'-yl)-pentanoic acid methyl ester;

4-(7'-exo-formyl-2'-oxa-bicyclo[3.4.0]nonan-3'-yl)-butanoic acid methyl ester;

5-(6'-exo-formyl-7'-endo-hydroxy-2'-oxa-bicyclo[3.3.0]octan-3'-yl)-pentanoic acid methyl ester;

4-(7'-exo-formyl-8'-endo-hydroxy-2'-oxa-bicyclo[3.4.0]nonan-3'-yl)-butanoic acid methyl ester;

5-chloro-5-(6'-exo-formyl-2'-oxa-bicyclo[3.3.0]octan-3'-yl)-pentanoic acid methyl ester;

4-chloro-4-(7'-exo-formyl-2'-oxa-bicyclo[3.4.0]nonan-3'-yl)butanoic acid methyl ester;

5-chloro-5-(6'-exo-formyl-7'-endo-hydroxy-2'-oxa-bicyclo [3.3.0]octan-3'-yl)-pentanoic acid methyl ester;

4-chloro-4-(7'-exo-formyl-8'-endo-hydroxy-2'-oxa-bicyclo [3.4.0]nonan-3'-yl)-butanoic acid methyl ester;

5-bromo-5-(6'-exo-formyl-2'-oxa-bicyclo[3.3.0]octan-3'-yl)-pentanoic acid methyl ester;

4-bromo-4-(7'-exo-formyl-2'-oxa-bicyclo[3.4.0]nonan-3'-yl)butanoic acid methyl ester;

5-bromo-5-(6'-exo-formyl-7'-endo-hydroxy-2'-oxa-bicyclo [3.3.0]octan-3'-yl)-pentanoic acid methyl ester;

4-bromo-4-(7'-exo-formyl-8'-endo-hydroxy-2'-oxa-bicyclo [3.4.0]nonan-3'-yl)-butanoic acid methyl ester;

5-iodo-5-(6'-exo-formyl-2'-oxa-bicyclo[3.3.0]octan-3'-yl)pentanoic acid methyl ester;

4-iodo-4-(7'-exo-formyl-2'-oxa-bicyclo[3.4.0]nonan-3'-yl)butanoic acid methyl ester;

5-iodo-5-(6'-exo-formyl-7'-endo-hydroxy-2'-oxa-bicyclo[3.3.0] octan-3'-yl)-pentanoic acid methyl ester;

4-iodo-4-(7'-exo-dormyl-8'-endo-hydroxy-2'-oxa-bicyclo [3.4.0]nonan-3'-yl)-butanoic acid methyl ester;

5-(6'-exo-formyl-7'-endo-hydroxy-2'-oxa-bicyclo[3.3.0]octan-3'-yl)-pentanoic acid methyl ester-7'-acetate;

5-iodo-5-(6'-exo-formyl-7'-endo-hydroxy-2'-oxa-bicyclo[3.3.0]octan-3'-yl-pentanoic acid methyl ester-7'-acetate;

5-(7'-exo-formyl-8'-endo-hydroxy-2'-oxa-bicyclo[3.4.0] nonan-3'-yl)-pentanoic acid methyl ester;

4-(6'-exo-formyl-7'-endo-hydroxy-2'-oxa-bicyclo[3.3.0]octan-3'-yl)-butanoic acid methyl ester.

EXAMPLE 35

To a solution of 1.2 g of 5-(6'-exo-benzyloxymethyl-2'-oxa-bicyclo[3.3.0]octan-3'-yl)-pentanoic acid methyl ester in methanol: methyl acetate (10 ml:10 ml) is added 2 ml of a 0;1 N methanol solution of HCl. After 0.15 g of PtO₂ is added, the mixture is hydrogenated at ambient temperature and pressure until 1 molar equivalent of hydrogen is absorbed. After the removal of the gas under vacuum and washing with nitrogen, the suspension is filtered, neutralized, and evaporated to dryness. The residue is taken up in water/ethyl acetate, and the organic phase yields 0.84 g of 5-(6'-exo-hydroxymethyl-2'-oxa-bicyclo[3.3.0]octan-3'-yl)-pentanoic acid methyl ester. This is then oxidized to the 6'-exo-formyl derivative by the procedure in example 1, using dicyclohexylcarbodiimide in DMSO:benzene (25:75).

EXAMPLE 36

To a solution of 18.1 g of 5β-tetrahydropyranyloxymethyl-2α,4α-dihydroxy-cyclopent-1α-acetic acid-α-lactone-4-tetrahydropyranyl ether in 150 ml of toluene cooled to −70° C. is added in 30 minutes 128 ml of a 5 M solution of di-iso-butylaluminum hydride (1.2 M/M). After 30 minutes at −70° C., 128 ml of a 2 M toluene solution of isopropanol is added and the solution is brought to 0° C. Then 10 ml of a saturated aqueous solution of NaH₂PO₄ is added and the mixture is stirred for four hours. Following the addition of 10 g of anhydrous Na₂SO₄ and 10 g of filtering earth, the solution is filtered and evaporated to dryness to give 18.1 g of 5β-tetrahydropyranyloxymethyl-2α,4α-dihydroxy-cyclopent-1α-ethanal-α-lactol-4-tetrahydropyranyl ether. A solution of this in 24 ml of anhydrous DMSO is added dropwise to a solution of the ylide prepared as follows: 9.6 g of 80% sodium hydride in 300 ml of DMSO is heated for four hours at 60° C. Then after the mixture is brought to 18°-20° C., 67 g of 4-carboxybutyltriphenyl phosphonium bromide dissolved in 80 ml of anhydrous DMSO is added while maintaining a temperature of 20°-22° C. to generate a bright red color. After four hours of stirring, 600 ml of water is added and the mixture is extracted with ethyl ether:benzene (70:30) to remove the triphenylphosphine oxide. The benzene organic phase is re-extracted with 0.1 N NaOH and then with water until neutral; it is then discarded. The alkaline aqueous phase is acidified to pH 5-4.8 and then extracted with ethyl ether:pentane (1:1) to give 21.6 g of 5-cis-7-(2'α,4'α-dihydroxy-5'β-tetrahydropyranyloxymethyl-cyclopent-1α-yl)-hept-5-enoic acid-4'-tetrahydropyranyl ether, which may be converted to its methyl ester by treatment with diazomethane in ether. 7.72 g of this ester in 28 ml of tetrahydrofuran is added dropwise to a yellow-brown suspension formed by adding 28 ml of THF to a solution of 6.13 g of mercuric acetate in 28 ml of water. After the mixture is stirred for 20 minutes at room temperature, it is cooled in an ice:water bath and 810 mg of NaBH₄ in 14 ml of water is added dropwise. Elemental mercury precipitates out, the suspension is decanted, the tetrahydrofuran is evaporated at reduced pressure and the residue is extracted with ethyl ether. Removal of the solvent affords 7.5 g of 5-(6'-exo-tetrahydropyranyloxymethyl-7'-hydroxy-2'-oxa-bicyclo[3.3.0]octan-3'-yl)-pentanoic acid methyl ester-7'-tetrahydropyranyl ether; 0.42 g of p-toluenesulfonic acid is then added to a solution of this in 30 ml of methanol. After 2 hours at room temperature, the solution is concentrated under vacuum and water is added. After extraction with ether and chromatography on silica gel with ethyl ether as eluent, one obtains 2.4 g of 5-(6'-exo-hydroxymethyl-7'-hydroxy-2'-oxa-bicyclo[3.3.0]octan-3'-exo-yl)-pentanoic acid methyl ester and 2.6 g of the 3'-endo isomer.

EXAMPLE 37

2.5 g of N-iodosuccinimide is added to a solution of 4.26 g of 5-cis-7-(2'α,4'α-dihydroxy-5'β-tetrahydropyranyloxymethyl-cyclopent-1'α-yl)-hept-5-enoic acid-4'-tetrahydropyranyl ether is $CH_2Cl_2:CCl_4$ (10 ml:10 ml) and the resulting mixture is stirred for four hours. 30 ml of anhydrous methanol containing 130 mg of p-toluenesulfonic acid is added and stirring is continued for another 2 hours. 0.2 ml of pyridine is added, the mixture is reduced to small volume, and the residue is taken up in water/ethyl acetate. After washing with $Na_2S_2O_3$ and then water until neutral, the organic phase is evaporated to dryness to give a residue that is adsorbed on silica gel and eluted with ethyl ether to give 2.2 g of 5-iodo-5-(6'-exohydroxymethyl-7'-hydroxy-2'-oxa-bicyclo[3.3.0]octan-3'-exo-yl)-pentanoic acid methyl ester and 1.85 g of the 3'-endo isomer.

EXAMPLE 38

Following the procedure of example 37, but using the methyl ester instead of the acid and N-bromoacetamide instead of N-iodosuccinimide, the 5-bromo-5-(6'-exohydroxymethyl-7'-hydroxy-2'-oxa-bicyclo[3.3.0]octan-3'-yl)-pentanoic acid methyl ester is prepared. Silica gel chromatography allows the separation into the 3'-exo and 3'-endo isomers.

EXAMPLE 39

A solution of 0.86 g of pyridine and 2.2 g of 5-cis-7-(2'α,4'α-dihydroxy-5'β-tetrahydropyranyloxymethyl-cyclopent-1'α-yl)-hept-5-enoic acid methyl ester-4'-tetrahydropyranyl ether in dichloromethane (20 ml) is cooled to −30° C. and 0.38 g of chlorine in 10 ml of CCl$_4$:CH$_2$Cl$_2$ (1:1) is added. The mixture is stirred for 2 hours, warmed to room temperature, and washed with 2 N H$_2$SO$_4$ and then water until neutral. After evaporation of the solvent, the residue is dissolved in methanol (10 ml) and treated with 0.1 g of p-toluenesulfonic acid. The solution is then concentrated, diluted with water, and extracted with ethyl acetate. Removal of the solvent and purification of the residue on silica gel afford 0.6 g of 5-chloro-5-(6'-exo-hydroxymethyl-7'-endo-hydroxy-2'-oxa-bicyclo[3.3.0]octan-3'-exo-yl)-pentanoic acid and 0.71 g of the 3'-endo isomer.

EXAMPLE 40

To a solution of 0.356 g of 5-iodo-5-(6'-exo-hydroxymethyl-7'-endo-hydroxy-2'-oxa-bicyclo[3.3.0]octan-3'-exo-yl)-pentanoic acid methyl ester in 4.8 ml of benzene:DMSO (75:25) are added, in order, 0.28 g of dicyclohexylcarbodiimide and 0.4 ml of a pyridinium trifluoroacetate solution (see example 1). After 3 hours of stirring, 8 ml of benzene and then aqueous oxalic acid (94 mg in 1.2 ml) are added. The precipitate is removed by filtration and the benzene solution is washed with water until neutral. Removal of the solvent affords 0.32 g of 5-iodo-5-(6'-exo-formyl-7'-endo-hydroxy-2'-oxa-bicyclo[3.3.0]octan-3'-exo-yl)-pentanoic acid methyl ester.

EXAMPLE 41

Upon oxidation of the 6'-exo-hydroxymethyl-7'-endo-hydroxy derivatives prepared according to examples 36–39, following the procedure of example 40, the corresponding 6'-exo-formyl derivatives are prepared.

EXAMPLE 42

A solution of 3.4 g of (2-oxo-heptyl)dimethoxyphosphonate in 50 ml of dimethoxyethane is added dropwise to a suspension of 0.45 g of 80% NaH (mineral oil dispersion). After stirring for 1 hour, a solution of 2.7 g of 5-(6'-exo-formyl-7'-endo-hydroxy-2'-oxa-bicyclo[3.3.0]octan-3'-yl)-pentanoic acid methyl ester in 40 ml of dimethoxyethane is added. In 10 minutes this is diluted with 50 ml of a 30% aqueous solution of monobasic sodium phosphate. The organic phase is separated, the aqueous phase is re-extracted, and the combined organic extract is evaporated. Purification of the crude product on 50 g of silica gel (cyclohexane:ethyl ether, 50:50) gives 1.1 g of 5-[6'-exo-(3''-oxo-oct-1''-trans-en-1''-yl)-7'-endo-hydroxy-2'-oxa-bicyclo[3.3.0]octan-3'-endo-yl]-pentanoic acid methyl ester or 13t-6$\beta$H-6(9$\alpha$)-oxide-11$\alpha$-hydroxy-15-oxo-prost-13-enoic acid methyl ester and 0.98 g of 5-[6'-exo-(3''-oxo-oct-1''-trans-en-1''-yl)-7'-endo-hydroxy-2'-oxa-bicyclo[3.3.0]octan-3'-exo-yl]-pentanoic acid methyl ester or 13t-6$\alpha$H-6(9$\alpha$)-oxide-11$\alpha$-hydroxy-15-oxo-prost-13-enoic acid methyl ester, plus 0.9 g of a 1:1 mixture of the two isomers (3'-exo and 3'-endo, or 6$\alpha$H and 6$\beta$H). This last mixture is separated into its two isomeric components by thin layer chromatography with ethyl ether. They show the following absorptions, respectively: $\lambda_{max}^{MeOH} = 230$ m$\mu$, $\epsilon = 13,070$; $\lambda_{max}^{MeOH} = 228$ m$\mu$, $\epsilon = 12,200$.

N.M.R. (CDCl$_3$) 0.9 t 3H C$_{20}$–CH$_3$, 3.68 s 3H CO$_2$CH$_3$, 6.16 d 1H vinylic proton at C$_{14}$ (J$_{H14-H15}$ 16 Hz); 6.71 q 1H vinylic proton at C$_{13}$ (J$_{H13}$ 9 Hz).

By the same procedure, from the corresponding 5-H and 5-halo compounds, the following prostenoic acid derivatives are prepared:

13t-6$\alpha$H-6(9$\alpha$)-oxide-15-oxo-prost-13-enoic acid methyl ester;

13t-6$\alpha$H-6(9$\alpha$)-oxide-5-chloro-15-oxo-prost-13-enoic acid methyl ester;

13t-6$\alpha$H-6(9$\alpha$)-oxide-5-bromo-15-oxo-prost-13-enoic acid methyl ester;

13t-6$\alpha$H-6(9$\alpha$)-oxide-5-iodo-15-oxo-prost-13-enoic acid methyl ester;

13t-6$\alpha$H-6(9$\alpha$)-oxide-5-chloro-11$\alpha$-hydroxy-15-oxo-prost-13-enoic acid methyl ester;

13t-6$\alpha$H-6(9$\alpha$)-oxide-5-bromo-11$\alpha$-hydroxy-15-oxo-prost-13-enoic acid methyl ester, N.M.R. = 3.67 s 3H CO$_2$CH$_3$; 3.95 m 4H C$_5$,C$_9$,C$_{11}$ protons and Hx/Hy proton at C$_4$; 4.3 m 1H 6$\alpha$H; 6.15 d 1H C$_{14}$ proton; 6.63 q 1H C$_{13}$ proton;

13t-6$\alpha$H-6(9$\alpha$)-oxide-5-iodo-11$\alpha$-hydroxy-15-oxo-prost-13-enoic acid methyl ester, N.M.R. 0.9 s 3H C$_{20}$CH$_3$, 3.53 m 1H proton at C$_5$, 3.6 s 3H CO$_2$CH$_3$ 3.9 m H proton at C$_4$, 4.1 m 2H proton at C$_9$, C$_{11}$; 4.4 m 1H 6$\alpha$H; 6.2 d 1H proton at C$_{14}$ 6.75 q 1H proton at C$_{13}$;

13t-6$\beta$H-6(9$\alpha$)-oxide-15-oxo-prost-13-enoic acid methyl ester;

13t-6$\beta$H-6(9$\alpha$)-oxide-5-chloro-15-oxo-prost-13-enoic acid methyl ester;

13t-6$\beta$H-6(9$\alpha$)-oxide-5-bromo-15-oxo-prost-13-enoic acid methyl ester;

13t-6$\beta$H-6(9$\alpha$)-oxide-5-ido-15-oxo-prost-13-enoic acid methyl ester;

13-t-6$\beta$H-6(9$\alpha$)-oxide-5-chloro-11$\alpha$-hydroxy-15-oxo-prost-13-enoic acid methyl ester;

13-t-6$\beta$H-6(9$\alpha$)-oxide-5-bromo-11$\alpha$-hydroxy-15-oxo-prost-13-enoic acid methyl ester, N.M.R.: 3.65 s 3H CO$_2$CH$_3$; 4.00 m 3H proton at C$_5$,C$_9$,C$_{11}$, 4.6 m 1H 6$\beta$H; 6.2 d 1 H proton at C$_{14}$; 6.64 q 1H proton at C$_{13}$;

13t-6$\beta$H-6(9$\alpha$)-oxide-5-iodo-11$\alpha$-hydroxy-15-oxo-prost-13-enoic acid methyl ester; N.M.R. 3.66 s 3H CO$_2$CH$_3$, 3.96 m 3H protons at C$_9$,C$_{11}$ and C$_5$, 4.6 m 1H 6$\beta$H, 6.21 d 1H proton at C$_{14}$ 6.75 q 1H proton at C$_{13}$.

EXAMPLE 43

A solution of 2.16 g of (2-oxo-octyl)dimethylphosphonate in 20 ml of benzene is added dropwise to a suspension of 292 mg of NaH (75% mineral oil dispersion) in 30 ml of benzene. After 30 minutes of stirring, a solution of 2.6 g of 4-bromo-4-(7'-exo-formyl-8'-endo-hydroxy-2'-oxa-bicyclo[3.4.0]nonan-3'-yl)-butanoic acid methyl ester in 20 ml of benzene is added drop by drop. Stirring is continued for another 30 minutes, and 24 ml of a 30% aqueous solution of NaH$_2$PO$_4$ is added. The organic phase is separated, and the aqueous phase is reextracted with benzene. The organic layers are combined and evaporated to dryness. The residue is purified on silica gel (50 g) with CH$_2$Cl$_2$:ethyl ether (120:40) as eluent to give 0.52 g of 4-bromo-4-[7'-exo-(3''-oxo-oct-1''-trans-1''-enyl)-8'-endo-hydroxy-2'-oxa-bicyclo[3.4.0]nonan-3'-endo-yl]-butanoic acid methyl ester or 13-trans-4-bromo-4-bromo-5$\beta$H-5(9$\alpha$)-oxide-11$\alpha$-hydroxy-15-oxo-prost-13-enoic acid methyl ester and 1.45 g of 4-bromo-4-[7'-exo-(3''-oxo-oct-1''-trans-1''-enyl)-8'-endo-hydroxy-2'-oxa-bicyclo[3.4.0]nonan-3'-exo-yl]-butanoic acid methyl ester or 13-trans-4-bromo-5$\alpha$H-5(9$\alpha$)-oxide-11$\alpha$-hydroxy-15-oxo-prost-13-enoic acid methyl ester. Methanolic solutions of these two compounds absorb in the UV at $\lambda_{max}^{MeOH} = 230$ m$\mu$, $\epsilon = 10,640$, and $\lambda_{max}^{MeOH} = 229$ m$\mu$, $\epsilon = 11,600$, respectively.

The same procedure, starting from the 4-H and 4-halo bicyclo derivatives, gives the following prostenoic acids:

13-trans-5βH-5(9α)-oxide-15-oxo-prost-13-enoic acid methyl ester;
13-trans-5βH-5(9α)-oxide-11α-hydroxy-15-oxo-prost-13-enoic acid methyl ester;
13-trans-4-chloro-5βH-5(9α)-oxide-15-oxo-prost-13-enoic acid methyl ester;
13-trans-4-chloro-5βH-5(9α)-oxide-11α-hydroxy-15-oxo-prost-13-enoic acid methyl ester;
13-trans-4-bromo-5βH-5(9α)-oxide-15-oxo-prost-13-enoic acid methyl ester;
13-trans-4-bromo-5βH-5(9α)-oxide-11α-hydroxy-15-oxo-prost-13-enoic acid methyl ester;
13-trans-4-iodo-5βH-5(9α)-oxide-15-oxo-prost-13-enoic acid methyl ester;
13-trans-4-iodo-5βH-5(9α)-oxide-11α-hydroxy-15-oxo-prost-13-enoic acid methyl ester;
13-trans-5αH-5(9α)-oxide-15-oxo-prost-13-enoic acid methyl ester;
13-trans-5αH-5(9α)-oxide-11α-hydroxy-15-oxo-prost-13-enoic acid methyl ester;
13-trans-4-chloro-5αH-5(9α)-oxide-15-oxo-prost-13-enoic acid methyl ester;
13-trans-4-chloro-5αH-5(9α)-oxide-11α-hydroxy-15-oxo-prost-13-enoic acid methyl ester;
13-trans-4-bromo-5αH-5(9α)-oxide-15-oxo-prost-13-enoic acid methyl ester;
13-trans-4-bromo-5αH-5(9α)-oxide-11α-hydroxy-15-oxo-prost-13-enoic acid methyl ester;
13-trans-4-iodo-5αH-5(9α)-oxide-15-oxo-prost-13-enoic acid methyl ester;
13-trans-4-iodo-5αH-5(9α)-oxide-11α-hydroxy-15-oxo-prost-13-enoic acid methyl ester.

EXAMPLE 44

By the procedure of example 42, the reaction of 620 mg of (2-oxo-3-methyl-4-butoxybutyl)phosphonate with 74 mg of NaH (75%) and 0.43 g of 5-(6'-exo-formyl-7'-endo-hydroxy-2'-oxa-bicyclo[3.3.0]octan-3'β-yl)-pentanoic acid methyl ester in dimethoxethane gives, after chromatograhy on silica gel (25 g) with 1:1 ethyl ether:hexane as eluent, 0.15 g of 13t-6αH-6(9α)-oxide-11α-hydroxy-15-oxo-16-methyl-16-butoxy-18,19,20-trinor-prost-13-enoic and acid methyl ester (λ$_{max}$=238 mμ, ε=14,500) and 300 mg of the 6βH-isomer (λ$_{max}$=237 mμ, ε=12,280).

Mass spectrum: m/e 410 M+, m/e 392 M+ —$^H{_2}$O; m/e 379 M+ —OCH₃; m/e 295 M+ —115, m/e 115

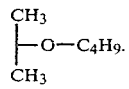

The two isomers present similar spectra with minimal differences at level of secondary fragmentation.

Using the same procedure the 5-chloro, 5-bromo and 5-iodo 13t-6 ⸘H-6(9α)-oxide-11α-hydroxy-15-oxo-16-methyl-16-butoxy-18,19,20-trinor-prost-13-enoic acid methyl ester.

EXAMPLE 45

By the procedure of example 44, from 4-(7'-exo-formyl-7'-endo-hydroxy-2'-oxa-bicyclo[3.4.0]nonan-3'β-yl)-butanoic acid methyl ester and the 4-iodo bicyclic derivative the following are obtained:

13t-5βH-5(9α)-oxide-11α-hydroxy-15-oxo-16-methyl-16-butoxy-18,19,20-trinor-prost-13-enoic acid methyl ester;
13t-4-iodo-5βH-5(9α)-oxide-11α-hydroxy-15-oxo-16-methyl-16-butoxy-18,19,20-trinor-prost-13-enoic acid methyl ester;
13t-5αH-5(9α)-oxide-11α-hydroxy-15-oxo-16-methyl-16-butoxy-18,19,20-trinor-prost-13-enoic acid methyl ester;
13t-4-iodo-5αH-5(9α)-oxide-11α-hydroxy-15-oxo-16-methyl-16-butoxy-18,19,20-trinor-prost-13-enoic acid methyl ester.

EXAMPLE 46

To a suspension of 45 mg of 80% NaH in 10 ml of benzene is added a solution of 375 mg of (2-oxo-3,3-dimethyl-heptyl)dimethylphosphonate in 10 ml of benzene, followed 30 minutes later by a solution of 0.305 g of 5-iodo-5-(6'-exo-formyl-2'-bicyclo[3.3.0]octan-3'β-yl)-pentanoic acd methyl ester. After stirring for 45 minutes, the mixture is diluted with 10% aqueous NaH₂PO₄. The organic phase is washed until neutral, dried and concentrated to small volume. Adsorption on silica gel and elution with cyclohexane:ethyl ether (90:10) give 0.12 g of 13t-5-iodo-6βH-6(9α)-oxide-15-oxo-16,16-dimethyl-prost-13-enoic acid methyl ester and 0.095 g of 13t-5-iodo-6αH-6(9α)-oxide-15-oxo-16,16-dimethyl-13-enoic acid methyl ester.

EXAMPLE 47

By substituting in the procedure of example 46 the formyl derivatives prepared according to example 34, the following 16,16-dimethyl derivatives are prepared:
13t-6βH-6(9α)-oxide-15-oxo-16,16-dimethyl-prost-13-enoic acid methyl ester;
13t-6βH-6(9α)-oxide-11α-hydroxy-15-oxo-16,16-dimethyl-prost-13-enoic acid methyl ester;
13t-5βH-5(9α)-oxide-15-oxo-16,16-dimethyl-prost-13-enoic acid methyl ester;
13t-5βH-5(9α)-oxide-11α-hydroxy-15-oxo-16,16-dimethyl-prost-13-enoic acid methyl ester;
13t-5-chloro-6βH-6(9α)-oxide-15-oxo-16,16-dimethyl-prost-13-enoic acid methyl ester;
13t-5-chloro-6βH-6(9α)-oxide-11α-hydroxy-15-oxo-16,16-dimethyl-prost-13-enoic acid methyl ester;
13t-4-chloro-5βH-5(9α)-oxide-15-oxo-16,16-dimethyl-prost-13-enoic acid methyl ester;
13t-4-chloro-5βH-5(9α)-oxide-11α-hydroxy-15-oxo-16,16-dimethyl-prost-13-enoic acid methyl ester;
13t-5-bromo-6βH-6(9α)-oxide-15-oxo-16,16-dimethyl-prost-13-enoic acid methyl ester;
13t-5-bromo-6βH-6(9α)-oxide-11α-hydroxy-15-oxo-16,16-dimethyl-prost-13-enoic acid methyl ester;
13t-4-bromo-5βH-5(9α)-oxide-15-oxo-16,16-dimethyl-prost-13-enoic acid methyl ester;
13t-bromo-5βH-5(9α)-oxide-11α-hydroxy-15-oxo-16,16-dimethyl-prost-13-enoic acid methyl ester;
13t-5-iodo-6βH-6(9α)-oxide-15-oxo-16,16-dimethyl-prost-13-enoic acid methyl ester;
13t-5-iodo-6βH-6(9α)-oxide-11α-hydroxy-15-oxo-16,16-dimethyl-prost-13-enoic acid methyl ester;
13t-4-iodo-5βH-5(9α)-oxide-15-oxo-16,16-dimethyl-prost-13-enoic acid methyl ester;
13t-4-iodo-5βH-5(9α)-oxide-11α-hydroxy-15-oxo-16,16-dimethyl-prost-13-enoic acid methyl ester;
13t-6αH-6(9α)-oxide-15-oxo-16,16-dimethyl-prost-13-enoic acid methyl ester;

13t-6αH-6(9α)-oxide-11α-hydroxy-15-oxo-16,16-dimethyl-prost-13-enoic acid methyl ester.

13t-5αH-5(9α)-oxide-15-oxo-16,16-dimethyl-prost-13-enoic acid methyl ester;

13t-5αH-5(9α)-oxide-11α-hydroxy-15-oxo-16,16-dimethyl-prost-13-enoic acid methyl ester;

13t-5-chloro-6αH-6(9α)-oxide-15-oxo-16,16-dimethyl-prost-13-enoic acid methyl ester;

13t-5-chloro-6αH-6(9α)-oxide-11α-hydroxy-15-oxo-16,16-dimethyl-prost-13-enoic acid methyl ester;

13t-4-chloro-5αH-5(9α)-oxide-15-oxo-16,16-dimethyl-prost-13-enoic acid methyl ester;

13t-4-chloro-5αH-5(9α)-oxide-11α-hydroxy-15-oxo-16,16-dimethyl-prost-13-enoic acid methyl ester;

13t-5-bromo-6αH-6(9α)-oxide-15-oxo-16,16-dimethyl-prost-13 enoic acid methyl ester;

13t-5-bromo-6αH-6(9α)-oxide-11α-hydroxy-15-oxo-16,16-dimethyl-prost-13-enoic acid methyl ester;

13t-4-bromo-5αH-5(9α)-oxide-15-oxo-16,16-dimethyl-prost-13-enoic acid methyl ester;

13t-4-bromo-5αH-5(9α)-oxide-11α-hydroxy-15-oxo-16,16-dimethyl-prost-13-enoic acid methyl ester;

13t-5-iodo-6αH-6(9α)-oxide-15-oxo-16,16-dimethyl-prost-13-enoic acid methyl ester;

13t-5-iodo-6αH-6(9α)-oxide-11α-hydroxy-15-oxo-16,16-dimethyl-prost-13-enoic acid methyl ester;

13t-4-iodo-5αH-5(9α)-oxide-15-oxo-16,16-dimethyl-prost-13-enoic acid methyl ester;

13t-4-iodo-5αH-5(9α)-oxide-11α-hydroxy-15-oxo-16,16-dimethyl-prost-13-enoic acid methyl ester;

EXAMPLE 48

To a suspension of 178 mg of NaH (75% mineral oil dispersion) in 15 ml of benzene is added dropwise a solution of 1.55 g of [2-oxo-3(S,R)-fluoro-4-cyclohexyl-butyl]-dimethylphosphonate in 10 ml of anhydrous benzene. After 30 minutes of stirring, a solution of 1 g of 5-(6'-exo-formyl-7'-endo-hydroxy-2'-oxa-bicyclo[3.3.0]octan-3' -yl)-pentanoic acid methyl ester is added and stirring is continued for another hour. The mixture is neutralized with 30% aqueous $NaH_2PO_4$, and the organic phase is separated, concentrated and adsorbed on silica gel. Elution with $CH_2Cl_2$:Et$_2$O (90:10) gives, 0.62 g of 13t-6αH-6(9α)-oxide-11α-hydroxy-15-oxo-16(S,R)-fluoro-17-cyclohexyl-18,19,20-trinor-prost-13-enoic acid methyl ester ($\lambda_{max}^{MeOH}=238$ mμ, $\epsilon=12,765$) and 0.31 g of the 6βH isomer ($\lambda_{max}^{MeOH}=238$ mμ, $\epsilon=9,870$).

The N.M.R. data for the former compound are the following (CDCl$_3$) p.p.m. 3.64 s 3H CO$_2$CH$_3$, 3.8 m 1H C$_9$ proton, 4.03 q 1H proton at C$_{11}$, 4.3 m 1H 6αH, 5.00 and 5.55 t,t ½ H,½ H proton at C$_{16}$ $J_{HF}$ 55 Hz, 6.54 q 1H proton at C$_{14}$ 6.9 q 1H proton at C$_{13}$ $J_{H14-H12}$ 3.5 Hz, $J_{H13-H12}$ 7.5 Hz, $J_{H13-H14}$ 15.5 Hz.

Treating this compound with pyridine and acetic anhydride it is converted into the 11α-acetoxy derivative, for which the N.M.R. data are: (CHCl$_3$) p.p.m. 2.02 s 3H OCOCH$_3$, 3.64 s 3H CO$_2$CH$_3$, 3.8 proton at C$_9$, 4.25 m 1H 6αH; 4.66, 5.22 t,t ½H,½H proton at C$_{16}$; 4.97 q 1H proton at C$_{11}$; 6.51 proton at C$_{14}$, 6.90 proton at C$_{13}$;

For the diastereoisomeric hydroxy ketones the mass spectrum shows the following masses: M+ 424 m/e and then M+—H$_2$O, M+—HF, M+—CH$_3$OH/CH$_2$O M+—CH$_2$=CHOH (basis ion) M+—115 M+—44-59 and M+—(CHF—CH$_2$—C$_6$H$_{11}$).

In mass spectrum of exo-diastereoisomer the following masses are predominant: M+—CH$_3$OH and M+—44-28; in that of endo-diastereoisomer the predominant ones are M+—CH$_3$O and M+—44-18.

From the 5-bromo derivative, 13t-5-bromo-6βH-6(9α)-oxide-11α-hydroxy-15-oxo-16(S,R)-fluoro-17-cyclohexyl-18,19,20-trinor-prost-13-enoic acid methyl ester is prepared.

EXAMPLE 49

Substituting in the procedure of example 48 a phosphonate chosen from (2-oxo-4-cyclohexyl-butyl)-dimethylphosphonate and (2-oxo-4-phenyl-butyl)-dimethylphosphonate, the following were prepared:

13t-6βH-6(9α)-oxide-11α-hydroxy-15-oxo-17-cyclohexyl-18,19,20-trinor-prost-13-enoic acid methyl ester, 13t-6βH-6(9α)-oxide-11α-hydroxy-15-oxo-17-phenyl-18,19,20-trinor-prost-13-enoic acid methyl ester and their 6βH isomers.

EXAMPLE 50

To a suspension of 178 mg of NaH (75% mineral oil dispersion) in anhydrous tetrahydrofuran at 0° C. is added dropwise with stirring a solution of 1.63 g of 2-oxo-3-(m-chlorophenoxy)-propyl-dimethylphosphonate in 10 ml of anhydrous THF. After 30 minutes of stirring, a solution of 1 g of 5-(6'-exo-formyl-7'-oxa-bicyclo[3.3.0]octan-3' -yl)-pentanoic acid methyl ester is added and stirring is continued for another hour. The mixture is acidified with aqueous NaH$_2$PO$_4$, the organic phase is separated, and the aqueous phase is re-extracted with benzene. From the combined organic extract, after chromatography on silica gel with CH$_2$Cl$_2$:Et$_2$O (95:5) as eluent, one obtains of 0.43 g of 13t-6αH-6(9α)-oxide-11α-hydroxy-15-oxo-16-m-chlorophenoxy-17,18,19,20-tetranor-prost-13-enoic acid methyl ester ($\lambda_{max}^{MeOH}=227$ mμ, $\epsilon=16,800$) and 0.11 g of the 6βH isomer ($\lambda_{max}=224$ mμ, $\epsilon=16,900$). Both the diastereoisomers show the mass peak m/e 436 in according to C$_{23}$H$_{29}$ClO$_6$. This ion is involved in the following fragmentation: M+—H$_2$O, M+—OCH$_3$/CH$_3$OH, M+—44, M+—(O—C$_6$H$_4$Cl), M+—H$_2$O—(O—C$_6$H$_4$Cl) and M+—(CH$_2$)$_4$—CO$_2$CH$_3$, so furthermore confirming the proposed structure. The following differences are between the two diastereoisomers: the exo 6αH isomer shows a peak at M+-32 and a little intense peak at M+-44 on the other hand the endo 6βH isomer shows a peak at M+-31 and on intense peak M+-44.

EXAMPLE 51

The substitution of a phosphonate chosen from 2-oxo-3-(m-trifluoromethylphenoxy)-propyl-dimethylphosphonate and 2-oxo-3-(p-fluorophenoxy)-propyl-dimethylphosphonate in the procedure of example 50 leads to the following compounds, respectively:

13t-6βH-6(9α)-oxide-11α-hydroxy-15-oxo-16m-trifluoromethyl phenoxy-17,18,19,20-tetranor-prost-13-enoic acid methyl ester, 13t-6βH-6(9α)-oxide-11α-hydroxy-15-oxo-16-p-fluoro phenoxy-17,18,19,20-tetranor-prost-13-enoic acid methyl ester, and their 6αH isomers.

The mass spectra of all the compounds agree with the proposed structure for example showing the mass peak M+-115; an interesting difference between the endo- and exo- trifluoromethyl analogous is that the mass peaks M+—CH$_3$OH and M+—CF$_3$—C$_6$H$_4$—OH are in the exo-isomer and the mass peak M+—CH$_3$O and M+—CF$_3$—C$_6$H$_4$—O are in the endo-isomer.

EXAMPLE 52

The substitution of (2-oxo-3S-methyl-butyl)-dimethyl phosphonate for the phosphonate in the procedure of example 48 gave 13t-6βH-6(9α)-oxide-11α-hydroxy-15-oxo-16S-methyl-prost-13-enoic acid methyl ester and its 6βH isomer. To a solution of 2.2 g of the 6βH isomer in 2.6 ml of pyridine, cooled to 0° C., is added 1.05 ml of acetic anhydride. The solution is held at 0° C. overnight and then added to an excess of cold 0.05 N sulfuric acid. Extraction with ethyl ether and evaporation to dryness give 2.3 g of 13t-6βH-6(9α)-oxide-11α-hydroxy-15-oxo-16S-methyl-prost-13-enoic acid methyl ester-11-acetate ($\lambda_{max}^{MeOH}=229$ mµ, $\epsilon=12,050$).

875 mg of bromine in glacial acetic acid is added dropwise to a solution of the latter compound in 10 ml of glacial acetic acid, until a light orange color appears. 1.52 g of anhydrous potassium carbonate is then added and the resulting mixture is held at 80° C. for 4–5 hours to complete the precipitation of potassium bromide. Excess acetic acid is removed under vacuum, water is added, and the pH is brought to pH 6.8 with alkaline hydrate. This is then extracted with ethyl ether and the organic phase is reduced in volume. Adsorption on silica gel and elution with methylene chloride:ethyl ether (70:30) gives 2.01 g of 13t-6βH-6(9α)-oxide-11α-hydroxy-14-bromo-15-oxo-16S-methyl-prost-13-enoic acid methyl ester-11-acetate, $\lambda_{max}^{MeOH}=249$ mµ, $\epsilon=11,450$. The 6αH isomer is similarly prepared.

EXAMPLE 53

A solution of 2.06 g of (2-oxo-3S-methylheptyl)-dimethyl phosphonate in 20 ml of dimethoxyethane is added dropwise to a suspension of 0.265 g of NaH (80% mineral oil dispersion) in DME (10 ml). After stirring for 30 minutes, 1.6 g of N-bromosuccinimide is added and vigorous stirring is continued for 10 minutes. 1.35 g of 5-(6'-exo-formyl-7'-endo-hydroxy-2'-oxa-bicyclo[3.3.0]octan-3'ξ-yl)-pentanoic acid methyl ester in 5 ml of dimethoxyethane is then added. The mixture is stirred for 1 hour and 20 ml of 30% $NaH_2PO_4$ is added. After the usual work-up, crude 14-bromoenone is obtained. Separation on silica gel with methylene chloride: ethyl ether (85:15) gives 0.9 g of 13t-6βH-6(9α)-oxide-11α-hydroxy-14-bromo-15-oxo-16S-methyl-prost-13-enoic acid methyl ester and 0.92 g of the 6αH isomer. Upon treatment with 0.4 ml of pyridine and 0.2 ml of acetic anhydride, 0.2 g of the 6βH isomer gives 0.205 g of the 11-acetoxy derivative, identical in all respects with that made by the procedure of example 52.

EXAMPLE 54

A solution of 0.43 g of (2-oxo-octyl)-dimethylphosphonate in 10 ml of benzene is added dropwise to a suspension of 54 mg of NaH (80% mineral oil dispersion) in 5 ml of benzene. After 1 hour, when the evolution of $H_2$ has ceased, 0.32 g of N-bromo succinimide is added all at once. To the carbanion thus prepared, of (1-bromo-2-oxo-octyl)-dimethylphosphonate is added a solution of 270 mg of 5-(6'-exo-formyl-7'-endo-hydroxy-2'-oxa-bicyclo[3.3.0]octan-3'ξ -yl)-pentanoic acid methyl ester in 8 ml of benzene. After 30 minutes, the reaction is quenched by the addition of 20 ml of a 10% solution of $NaH_2PO_4$. The organic phase, after being washed until neutral, gives 0.31 g of 13t-6βH-6(9α)-oxide-11α-hydroxy-14-bromo-15-oxo-20-methyl-prost-13-enoic acid methyl ester; this is then separated into the 6αH and 6βH isomers.

EXAMPLE 55

Upon substitution of the (2-oxo-octyl)-dimethylphosphonate in the procedure of example 54 with (2-oxo-4-cyclohexylbutyl)-dimethylphosphonate and (2-oxo-4-phenyl-butyl)-dimethylphosphonate, the following compounds were prepared:
13t-6βH-6(9α)-oxide-11α-hydroxy-14-bromo-15-oxo-17-cyclohexyl-18,19,20-trinor-prost-13-enoic acid methyl ester;
13t-6βH-6(9α)-oxide-11α-hydroxy-14-bromo-15-oxo-17-phenyl-18,19,20-trinor-prost-13-enoic acid methyl ester.

EXAMPLE 56

By substituting the formyl derivatives in examples 53, 54 and 55 with 5-iodo-5-(6'-exo-formyl-7'-endo-hydroxy-2'-oxa-bicyclo[3.3.0]octan-3'ξ -yl)-pentanoic acid methyl ester, 4-iodo-4-(7'-exo-formyl-8'-endo-hydroxy-2'-oxa-bicyclo[3.4.0]nonan-3'ξ -yl)-butanoic acid methyl ester, and the corresponding 4-H derivative, the following compounds were prepared:
13t-5-iodo-6βH -6(9α)-oxide-11α-hydroxy-14-bromo-15-oxo-16S-methyl-prost-13-enoic acid methyl ester;
13t-4-iodo-5βH-5(9α)-oxide-11α-hydroxy-14-bromo-15-oxo-16S-methyl-prost-13-enoic acid methyl ester;
13t-5βH-5(9α)-oxide-11α-hydroxy-14-bromo-15-oxo-16S-methyl-prost-13-enoic acid methyl ester;
13t-5-iodo-6βH-6(9α)-oxide-11α-hydroxy-14-bromo-15-oxo-20-methyl-prost-13-enoic acid methyl ester;
13t-4-iodo-5βH-5(9α)-oxide-11α-hydroxy-14-bromo-15-oxo-20-methyl-prost-13-enoic acid methyl ester;
13t-5βH-5(9α)-oxide-11α-hydroxy-14-bromo-15-oxo-20-methyl-prost-13-enoic acid methyl ester;
13t-5-iodo-6βH-6(9α)-oxide-11α-hydroxy-14-bromo-15-oxo-17-cyclohexyl-18,19,20-trinor-prost-13-enoic acid methyl ester;
13t-5βH-5(9α)-oxide-11α-hydroxy-14-bromo-15-oxo-17-cyclohexyl-18,19,20-trinor-prost-13-enoic acid methyl ester;
13t-5-iodo-6βH-6(9α)-oxide-11α-hydroxy-14-bromo-15-oxo-17-phenyl-18,19,20-trinor-prost-13-enoic acid methyl ester;
13t-5βH-5(9α)-oxide-11α-hydroxy-14-bromo-15-oxo-17-phenyl-18,19,20-trinor-prost-13-enoic acid methyl ester.

EXAMPLE 57

A solution of 0.61 g of 2-oxo-octyl-triphenylphosphonium bromide in 6 ml of DMSO is added to a solution of 0.15 g of potassium t-butylate in 3 ml of DMSO while keeping the reaction temperature at 16°–19° C. 0.27 g of 5-(6'-exo-formyl-7'-endo-hydroxy-2'-oxa-bicyclo[3.3.0]octan-3'ξ -yl)-pentanoic acid methyl ester in 8 ml of anhydrous tetrahydrofuran is then added.

After 30 minutes of stirring, an equal volume of water is added and the mixture is extracted with ethyl ether. The combined organic extract is washed until neutral and the solvent is evaporated. Chromatography on silica gel (cyclohexane:ethyl ether, 40:60) gives 0.21 g of 13t-6 H-6(9α)-oxide-11α-hydroxy-15-oxo-20-methyl-prost-13-enoic acid methyl ester. Subsequent preparative thin layer chromatography ($SiO_2$-$Et_2O$) allows separation of the 6αH and 6βH isomers.

EXAMPLE 58

A solution of d,l-13t-6αH-6(9α)-oxide-11α-hydroxy-15-oxo-13-enoic acid methyl ester (exo-isomer at greatest R$_f$), (0.9 g), in dry ethyl ether (30 ml) is dripped on to a stirred 0.1 M solution of Zn(BH$_4$)$_2$ in dry ethyl ether (30 ml), over 15 minutes. After 2 hours, the excess reagent is decomposed by cautious addition of saturated NaCl solution and aqueous 2 N sulfuric acid. The organic layer is separated, washed to neutral and evaporation to dryness affording a residue which is adsorbed on silica gel, eluted with ethyl ether to yield 0.38 g of 13t-6αH-6(9α)-oxide-11α,15R-dihydroxy-prostenoic acid methyl ester, as an oil, and 0.42 g of d,l-13t-6αH-6(9α)-oxide-11α,15S-dihydroxy-prostenoic acid methyl ester, m.p. 69°-71° C. (mass spectrum m/e 350 M+-18, 319 M+-18-CH$_3$O; 318 M+-18—CH$_3$OH). A solution in methanol (4 ml) of this ester is treated with 60 mg of lithium hydroxide and water (0.8 ml) for 8 hours at room temperature. The methanol is removed in vacuum, the residue is diluted with water and extracted with ethyl ether to remove neutral impurities. The alkaline phase is treated with aqueous saturated NaH$_2$PO$_4$ solution until to pH 5 and then extracted with ethyl ether. The later organic phases are collected to yield after evaporation of the solvents the free acid d,l-13t-6αH-6(9α)-oxide-11α,15S-dihydroxy-prostenoic acid, m.p. 105°-106° C. The 15R-hydroxy compound is a non-crystallizable oil.

In the same way using nat-keto compound in the reduction reaction with Zn(BH$_4$)$_2$ we obtained besides the 15-epi alcohol, the nat-13t-6αH-6(9α)-oxide-11α,15S-dihydroxy-prostenoic acid methyl ester, m.p. 71°-72° C. [α]$_D$=+10.2°, [α]$_{365}$·=+32.2° (CHCl$_3$) and after saponification the free acid m.p. 101°-102° C. [α]$_D$=+6.34°, [α]$_{365}$·=+33.2° (CHCl$_3$).

Starting from the endo-diastereoisomers (more polar compounds), the following esters were obtained:
13t-6βH-6(9α)-oxide-11α,15R-dihydroxy-prostenoic acid methyl ester (d,l, nat-, ent- oils);
13t-6βH-6(9α)-oxide-11α,15S-dihydroxy-prostenoic acid methyl ester (d,l, nat-, [α]$_D$=+24.5°, [α]$_{365}$·=+52.9° (CHCl$_3$) oil; ent- [α]$_D$=−22°, oil), and after saponification the following free acids:
13t-6βH-(9α)-oxide-11α,15R-dihydroxy-prostenoic acid (d,l, nat-, ent- oils);
13t-6βH-6(9α)-oxide-11α,15S-dihydroxy-prostenoic acid (d,l oil, nat-, m.p. 78°-80° C. [α]$_D$=+32.5°, [α]$_{365}$·=+11.6° (EtOH), ent- m.p. 78°-79° C., [α]$_D$=−31° (EtOH).

EXAMPLE 59

With the temperature of the reaction mixture kept at around −5° to −8° C., a solution of 159 mg of NaBH$_4$ in 7 ml of propan-2-ol, is gradually added to a solution of 0.332 g of anhydrous CaCl$_2$ in propan-2-ol (7 ml); then, under stirring, a solution of 0.38 g of 13t-6αH-6(9α)-oxide-11α-hydroxy-15-oxo-16(S,R)-fluoro-17-cyclohexyl-18,19,20-trinor-prost-13-enoic acid methyl ester in 3 ml of propan-2-ol is added to the above prepared Ca(BH$_4$)$_2$ in a period of 40 minutes. The reaction mixture is kept under stirring at a temperature ranging at ±5° C., then the excess reagent is destroyed by addition of 5 ml of acetone and 2 ml of water. The solvent is evaporated under vacuum and the residue is partitioned among water, 0.1 N H$_2$SO$_4$ and ethyl acetate. The organic extracts are collected, washed until neutral and after evaporation of solvent the residue chromatographed on silica gel (30 g) using CH$_2$Cl$_2$-ethyl ether 70:30 as eluent. The eluate yields 0.21 g of 13t-6αH-6(9α)-oxide-11α,15R-dihydroxy-16(S,R)-fluoro-17-cyclohexyl-18,19,20-trinor-prost-13-enoic acid methyl ester, and 0.14 g of the 15S-epimer, m.p. 83°-84° C. (from ethyl ether). In the same way, reduction of the 6βH-isomer (220 mg) yields 0.1 g of 13t-6βH-6(9α)-oxide-11α,15R-dihydroxy-16(S,R)-fluoro-17-cyclohexyl-18,19,20-trinor-prost-13-enoic acid methyl ester, m.p. 63°-64° C. (from isopropylic ether), and 60 mg of 15S-alcohol.

EXAMPLE 60

A solution of 0.15 g of 13t-6αH-6(9α)-oxide-11α-hydroxy-15-keto-16-methyl-16-butoxy-18,19,20-trinor-prostenoic acid methyl ester in methanol (5 ml) is cooled at −5°+−10° C. and reduced by addition of a solution of NaBH$_4$ (30 mg) in water (0.5 ml). The reaction mixture is neutralized by addition of 15% aqueous NaH$_2$PO$_4$ solution after 15 minutes and then evaporated in vacuum. The aqueous residue is extracted with ethyl ether to yield a crude mixture of epimeric 15R,15S-alcohols. Chromatographic separation on silica gel (CH$_2$Cl$_2$-ethyl ether 70:30 as eluent) affords respectively 13t-6αH-6(9α)-oxide-11α,15R-dihydroxy-16-methyl-16-butoxy-18,19,20-trinor-prostenoic acid methyl ester (45 mg) and 15S-hydroxy-epimer (62 mg).

EXAMPLE 61

By reduction of 13t-5αH-5(9α)-oxide-11α-hydroxy-15-keto-16-methyl-16-butoxy-18,19,20-trinor-prostenoic acid methyl ester, under the same trial conditions as in the procedure ester, under the same trial conditions as in the procedure of example 60 followed by chromatographic separation of the epimeric alcohols (300 mg) on silica gel (12 g) with methylene chloride-ethyl ether 75:25 eluent, we respectively obtained 100 mg of 13t-5αH-5(9α)-oxide-11α,15R-dihydroxy-16-methyl-16-butoxy-18,19,20-trinor-prostenoic acid methyl ester, and 110 mg of 15S-epimer. These are then saponified to yield the corresponding free acids.

EXAMPLE 62

Dropwise, to a stirred 0.12 M solution of zincborohydride in ethyl ether (8 ml) a solution of 0.135 g of 13t-5-bromo-6αH-6(9α)-oxide-11α-hydroxy-15-oxo-prostenoic acid methyl ester in 2 ml of anhydrous Et$_2$O is added. The mixture is stirred for 2 hours and the excess reagent is decomposed with water-2 H$_2$SO$_4$. The organic phase is separated, washed to neutral and evaporated to dryness. After TLC on silica gel with ethyl ether-ethyl acetate 90:10, 38 mg of 13t-5-bromo-6αH-6(9α)-oxide-11α,15R-dihydroxy-prostenoic acid methyl ester and 46 mg of 15S-epimer were obtained.

EXAMPLE 63

Starting from 13t-5,14-dibromo-6βH-6-9(9α)-oxide-11α-hydroxy-15-oxo-prostenoic acid methyl ester (0.2 g) and using a mixture of CH$_2$Cl$_2$-ethyl ether 60:40, during the chromatographic separation on silica gel, we obtained 0.056 g of 13t-5,14-dibromo-6βH-6(9α)-oxide-11α,15R-dihydroxy-prostenoic acid methyl ester and 0.098 g of 15S-isomer. A solution of this product in methanol is then hydrolized with aqueous LiOH to yield 72 mg of 13t-5,14-dibromo-6αH-6(9α)-oxide-11α,15S-dihydroxy-prostenoic acid.

EXAMPLE 64

Using, in the procedure of example 60, isopropanol as solvent and NaBH$_4$ (45 mg), the reduction of 13t-6βH-6(9α)-oxide-11α-hydroxy-15-oxo-16-(m-trifluoromethyl)-phenoxy-17,18,19,20-tetranor-prost-13-enoic acid methyl ester (0.47 g) yields 0.20 g of 13t-6βH-6(9α)-oxide-11α,15S-dihydroxy-16-(m-trifluoromethyl)-phenoxy-17,18,19,20-tetranor-prost-13-enoic acid methyl ester, $[\alpha]_D = +33.3°$ (MeOH) and 0.18 g of 15R-epimer. The 6αH-15S-alcohol epimer is an oil with $[\alpha]_D = +12°$ (MeOH).

EXAMPLE 65

A solution in dry ethyl ether (20 ml) of 13t-16S-methyl-6αH-6(9α)-oxide-11α-hydroxy-15-oxo-prost-13-enoic acid methyl ester (0.002 M, 0.72 g) is added to a stirred etheral solution of zinc borohydride (0.01 M, 100 ml). The excess reagent is destroyed, after 30–45 minutes, by addition of 2 N-sulphuric acid in NaCl saturated aqueous solution. The organic phase is washed until neutral and evaporated to dryness. The residue is chromatographied on silica gel (25 g) using methylenechloride:ethyl ether (80:20) as eluent affording (7.5.10$^{-4}$ M, 0.27 g) of the 15R-hydroxy-isomer and (1.1.10$^{-4}$ M; 0.38 g) of the 15S-alcohol: 13t-16S-methyl-6αH-6(9α)-oxide-11α,15S-dihydroxy-prost-13-enoic acid methyl ester. Using this procedure, the following methyl esters were obtained:

13t-6βH-6(9α)-oxide-16S-methyl-11α,15S-dihydroxy-prost-13-enoic acid;
13t-6βH-6(9α)-oxide-16R-methyl-11α,15S-dihydroxy-prost-13-enoic acid;
13t-6βH-6(9α)-oxide-16,16-dimethyl-11α,15S-dihydroxy-prost-13-enoic acid;
13t-6αH-6(9α)-oxide-20-methyl-11α,15S-dihydroxy-prost-13-enoic acid, m.p. 57°–59° C. $[\alpha]_D = +14°$, $[\alpha]_{365°} = +47°$ (CHCl$_3$);
13t-6βH-6(9α)-oxide-20S-methyl-11α,15S-dihydroxy-prost-13-enoic acid, m.p. 38°–39° C., $[\alpha]_D = +21.7°$, $[\alpha]_{365°} = +77°$ (CHCl$_3$);
13t-5-bromo-6βH-6(9α)-oxide-16S-methyl-11α,15S-dihydroxy-prost-13-enoic acid;
13t-5-bromo-6βH-6(9α)-oxide-16R-methyl-11α,15S-dihydroxy-prost-13-enoic acid;
13t-5-bromo-6βH-6(9α)-oxide-16,16-dimethyl-11α,15S-dihydroxy-prost-13-enoic acid;
13t-5-bromo-6βH-6(9α)-oxide-11α,15S-dihydroxy-20-methyl-prost-13-enoic acid, $[\alpha]_D = +38°$;
13t-5-iodo-6βH-6(9α)-oxide-16S-methyl-11α,15S-dihydroxy-prost-13-enoic acid;
13t-5-iodo-6βH-6(9α)-oxide-16S-methyl-11α,15S-dihydroxy-prost-13-enoic acid;
13t-5-iodo-6βH-6(9α)-oxide-16R-methyl-11α,15S-dihydroxy-prost-13-enoic acid;
13t-5-iodo-6βH-6(9α)-oxide-16,16-dimethyl-11α,15S-dihydroxy-prost-13-enoic acid;
13t-5-iodo-6βH-6(9α)-oxide-11α,15S-dihydroxy-20-methyl-prost-13-enoic acid, $[\alpha]_D = +23°$, $[\alpha]_{365°} = +78°$ (CHCl$_3$);
13t-5-chloro-6βH-6(9α)-oxide-16S-methyl-11α,15S-dihydroxy-prost-13-enoic acid;
13t-5βH-5(9α)-oxide-16S-methyl-11α,15S-dihydroxy-prost-13-enoic acid;
13t-5βH-5(9α)-oxide-16,16-dimethyl-11α,15S-dihydroxy-prost-13-enoic acid;
13t-4-bromo-5βH-5(9α)-oxide-16S-methyl-11α,15S-dihydroxy-prost-13-enoic acid;
13t-4-bromo-5βH-5(9α)-oxide-16R-methyl-11α,15S-dihydroxy-prost-13-enoic acid;
13t-4-bromo-5βH-5(9α)-oxide-16,16-dimethyl-11α,15S-dihydroxy-prost-13-enoic acid;
13t-4-iodo-5βH-5(9α)-oxide-16S-methyl-11α,15S-dihydroxy-prost-13-enoic acid;
13t-4-chloro-5βH-5(9α)-oxide-16S-methyl-11α,15S-dihydroxy-prost-13-enoic acid;
13t-6βH-6(9α)-oxide-16S-methyl-11α,15S-dihydroxy-14-bromo-prost-13-enoic acid;
13t-6βH-6(9α)-oxide-16R-methyl-11α,15S-dihydroxy-14-bromo-prost-13-enoic acid;
13t-6βH-6(9α)-oxide-20-methyl-11α,15S-dihydroxy-14-bromo-prost-13-enoic acid;
13t-6βH-6(9α)-oxide-15(S,R)-20-dimethyl-11α,15S-dihydroxy-14-bromo-prost-13-enoic acid;
13t-5βH-5(9α)-oxide-16S-methyl-11α,15S-dihydroxy-14-bromo-prost-13-enoic acid;
13t-5βH-5(9α)-oxide-16R-methyl-11α,15S-dihydroxy-14-bromo-prost-13-enoic acid;
13t-5βH-5(9α)-oxide-20-methyl-11α,15S-dihydroxy-14-bromo-prost-13-enoic acid;
13t-5βH-5(9α)-oxide-16(S,R)-20-methyl-11α,15S-dihydroxy-14-bromo-prost-13-enoic acid;
13t-5-bromo-6βH-6(9α)-oxide-16S-methyl-11α,15S-dihydroxy-14-bromo-prost-13-enoic acid;
13t-5-bromo-6βH-6(9α)-oxide-16R-methyl-11α,15S-dihydroxy-14-bromo-prost-13-enoic acid;
13t-5-bromo-6βH-6(9α)-oxide-20-methyl-11α,15S-dihydroxy-14-bromo-prost-13-enoic acid;
13t-5-bromo-6βH-6(9α)-oxide-16(S,R)-20-dimethyl-11α,15S-dihydroxy-14-bromo-prost-13-enoic acid;
13t-4-bromo-5βH-5(9α)-oxide-16S-methyl-11α,15S-dihydroxy-14-bromo-prost-13-enoic acid;
13t-4-bromo-5βH-5(9α)-oxide-16R-methyl-11α,15S-dihydroxy-14-bromo-prost-13-enoic acid;
13t-4-bromo-5βN-5(9α)-oxide-20-methyl-11α,15S-dihydroxy-14-bromo-prost-13-enoic acid;
13t-4-bromo-5βH-5(9α)-oxide-16(S,R)-20-dimethyl-11α,15S-dihydroxy-14-bromo-prost-13-enoic acid;
together with their 15R-epimeric alcohols, when the corresponding 15-keto compounds are submitted to reduction followed by chromatographic separation. Separating from 6αH and 5αH diastereoisomeric 15-keto compounds we prepare the corresponding 15S- and 15R-alcohols. All these compounds are then saponified to yield the corresponding free acids.

EXAMPLE 66

A solution of 13t-5-iodo-6βH-6(9α)-oxide-16R-methyl-15-oxo-prost-13-enoic acid methyl ester (0.32 g) in ethyl ether (8 ml) is added to a stirred solution of zinc borohydride in ethyl ether (25 ml). After 30 minutes, the excess reagent was destroyed by addition of a saturated solution of NaCl and N H$_2$SO$_4$. After the usual work up the organic pulse is separated and the crude residue is chromatographed on SiO$_2$ (eluent (CH$_2$Cl$_2$-ethyl ether) to yield 0.16 g of 13t-5-iodo-6βH-6(9α)-oxide-16R-methyl-15S-hydroxy-prost-13-enoic acid methyl ester and 0.095 g of 15R-epimer. Using this procedure the following methyl esters were obtained:

13t-6βH-6(9α)-oxide-15S-hydroxy-16S-methyl-prost-13-enoic acid;
13t-6βH-6(9α)-oxide-15S-hydroxy-16R-methyl-prost-13-enoic acid;
13t-6βH-6(9α)-oxide-15S-hydroxy-16,16-dimethyl-prost-13-enoic acid;

13t-5βH-5(9α)-oxide-15S-hydroxy-16S-methyl-prost-13-enoic acid;
13t-5βH-5(9α)-oxide-15S-hydroxy-16R-methyl-prost-13-enoic acid;
13t-5βH-5(9α)-oxide-15S-hydroxy-16,16-dimethyl-prost-13-enoic acid;
13t-5-bromo-6βH-6(9α)-oxide-15S-hydroxy-16S-methyl-prost-13-enoic acid;
13t-5-bromo-6βH-6(9α)-oxide-15S-hydroxy-16R-methyl-prost-13-enoic acid;
13t-5-bromo-6βH-6(9α)-oxide-15S-hydroxy-16,16-dimethyl-prost-13-enoic acid;
13t-5-bromo-6βH-6(9α)-oxide-15S-hydroxy-20-methyl-prost-13-enoic acid;
13t-5-bromo-6βH-6(9α)-oxide-15S-hydroxy-16S,20-dimethyl-prost-13-enoic acid, together with their 15R-epimeric alcohols, when the corresponding 15-keto compounds are submitted to reduction followed by chromatographic separation.

Starting from 6αH and 5αH diastereoisomeric 15-keto compounds we prepare the corresponding 15S- and 15R-alcohols.

EXAMPLE 67

The following 15S-hydroxy-9α-oxide prostanoic acids methyl esters together with their 15R-epimeric alcohols are obtained after reduction of the corresponding 15-keto compounds using one of the procedures described in examples 58 to 66:

13t-6βH-6(9α)-oxide-11α,15S-dihydroxy-13-prostanoic acid;
13t-14-bromo-6βH-6(9α)-oxide-11α,15S-dihydroxy-13-prostenoic acid;
13t-14-chloro-6βH-6(9α)-oxide-11α,15S-dihydroxy-13-prostenoic acid;
13t-5,14-dibromo-6βH-6(9α)-oxide-11α,15S-dihydroxy-13-prostenoic acid;
13t-6βH-6(9α)-oxide-11α,15S-dihydroxy-20-methyl-13-prostenoic acid;
13t-14-bromo-6βH-6(9α)-oxide-11α,15S-dihydroxy-20-methyl-13-prostenoic acid;
13t-5,14-dibromo-6βH-6(9α)-oxide-11α,15S-dihydroxy-20-methyl-13-prostenoic acid;
13t-5-iodo-6βH-6(9α)-oxide-11α,15S-dihydroxy-20-methyl-13-prostenoic acid;
13t-5-iodo-14-bromo-6βH-6(9α)-oxide-11α,15S-dihydroxy-20-methyl-13-prostenoic acid;
13t-14-bromo-6βH-6(9α)-oxide-11α,15S-dihydroxy-16(S,R)-fluoro-17-cyclohexyl-18,19,20-trinor-prost-13-enoic acid;
13t-5,14-dibromo-6βH-6(9α)-oxide-11α,15S-dihydroxy-16(S,R)-fluoro-17-cyclohexyl-18,19,20-trinor-prost-13-enoic acid;
13t-5-bromo-6βH-6(9α)-oxide-11α,15S-dihydroxy-16(S,R)-fluoro-17-cyclohexyl-18,19,20-trinor-prost-13-enoic acid;
13t-6βH-6(9α)-oxide-11α,15S-dihydroxy-16-difluoro-17-cyclohexyl-18,19,20-trinor-prost-13-enoic acid;
13t-14-bromo-6βH-6(9α)-oxide-11α,15S-dihydroxy-16-difluoro-17-cyclohexyl-18,19,20-trinor-prost-13-enoic acid;
13t-6βH-6(9α)-oxide-11α,15S-dihydroxy-16(S,R)-fluoro-17-phenyl-18,19,20-trinor-prost-13-enoic acid;
13t-14-bromo-6βH-6(9α)-oxide-11α,15S-dihydroxy-16(S,R)-fluoro-17-phenyl-18,19,20-trinor-prost-13-enoic acid;
13t-6βH-6(9α)-oxide-11α,15S-dihydroxy-17-cyclopentyl-18,19,20-trinor-prost-13-enoic acid;
13t-6βH-6(9α)-oxide-11α,15S-dihydroxy-17-cyclohexyl-18,19,20-trinor-prost-13-enoic acid;
13t-14-bromo-6βH-6(9α)-oxide-11α,15S-dihydroxy-17-cyclohexyl-18,19,20-trinor-prost-13-enoic acid;
13t-5,14-dibromo-6βH-6(9α)-oxide-11α,15S-dihydroxy-17-cyclohexyl-18,19,20-trinor-prost-13-enoic acid;
13t-5-bromo-6βH-6(9α)-oxide-11α,15S-dihydroxy-17-cyclohexyl-18,19,20-trinor-prost-13-enoic acid;
13t-5-chloro-6βH-6(9α)-oxide-11α,15S-dihydroxy-17-cyclohexyl-18,19,20-trinor-prost-13-enoic acid;
13t-5-iodo-6βH-6(9α)-oxide-11α,15S-dihydroxy-16-methyl-16-butoxy-18,19,20-trinor-prost-13-enoic acid;
13t-5-iodo-6βH-6(9α)-oxide-11α,15S-dihydroxy-16-methyl-16-propoxy-18,19,20-trinor-prost-13-enoic acid;
13t-5-iodo-6βH-6(9α)-oxide-11α,15S-dihydroxy-16-methyl-16-amyloxy-18,19,20-trinor-prost-13-enoic acid;
13t-5-iodo-6βH-6(9α)-oxide-11α,15S-dihydroxy-17-cycloheptyl-18,19,20-trinor-prost-13-enoic acid;
13t-6βH-6(9α)-oxide-11α,15S-dihydroxy-16-(p-fluoro)-phenoxy-17,18,19,20-tetranor-13-prostenoic acid;
13t-6βH-6(9α)-oxide-11α,15S-dihydroxy-16-phenoxy-17,18,19,20-tetranor-13-prostenoic acid;
13t-6βH-6(9α)-oxide-11α,15S-dihydroxy-16-cyclohexyloxy-17,18,19,20-tetranor-13-prostenoic acid;
13t-6βH-6(9α)-oxide-11α,15S-dihydroxy-16-(m-chloro)-phenoxy-17,18,19,20-tetranor-13-prostenoic acid;
13t-6βH-6(9α)-oxide-11α,15S-dihydroxy-16-(m-trifluoromethyl)-phenoxy-17,18,19,20-tetranor-13-prostenoic acid;
13t-14-bromo-6βH-6(9α)-oxide-11α,15S-dihydroxy-16-(p-fluoro)-phenoxy-17,18,19,20-tetranor-13-prostenoic acid;
13t-14-bromo-6βH-6(9α)-oxide-11α,15S-dihydroxy-16-phenoxy-17,18,19,20-tetranor-13-prostenoic acid;
13t-14-bromo-6βH-6(9α)-oxide-11α,15S-dihydroxy-16-(m-chloro)-phenoxy-17,18,19,20-tetranor-13-prostenoic acid;
13t-14-bromo-6βH-6(9α)-oxide-11α,15S-dihydroxy-16-m-trifluoromethyl)-phenoxy-17,18,19,20-tetranor-13-prostenoic acid;
13t-5-iodo-6βH-6(9α)-oxide-11α,15S-dihydroxy-16-(p-fluoro)-phenoxy-17,18,19,20-tetranor-13-prostenoic acid;
13t-5-iodo-6βH-6(9α)-oxide-11α,15S-dihydroxy-16-phenoxy-17,18,19,20-tetranor-13-prostenoic acid;
13t-5-iodo-6βH-6(9α)-oxide-11α,15S-dihydroxy-16-cyclohexyloxy-17,18,19,20-tetranor-13-prostenoic acid;
13t-5-iodo-6βH-6(9α)-oxide-11α,15S-dihydroxy-16-(m-chloro)-phenoxy-17,18,19,20-tetranor-13-prostenoic acid;
13t-iodo-6βH-6(9α)-oxide-11α,15S-dihydroxy-16-(m-trifluoromethyl)-phenoxy-17,18,19,20-tetranor-13-prostenoic acid;
13t-5βH-5(9α)-oxide-11α,15S-dihydroxy-13-prostenoic acid;
13t-14-bromo-5βH-5(9α)-oxide-11α,15S-dihydroxy-13-prostenoic acid;
13t-14-chloro-5βH-5(9α)-oxide-11α,15S-dihydroxy-13-prostenoic acid;
13t-4,14-dibromo-5βH-5(9α)-oxide-11α,15S-dihydroxy-13-prostenoic acid;
13t-5βH-5(9α)-oxide-11α,15S-dihydroxy-20-methyl-13-prostenoic acid;

13t-14-bromo-5βH-5(9α)-oxide-11α,15S-dihydroxy-20-methyl-13-prostenoic acid;
13t-4,14-dibromo-5βH-5(9α)-oxide-11α,15S-dihydroxy-20-methyl-13-prostenoic acid;
13t-4-iodo-5βH-5(9α)-oxide-11α,15S-dihydroxy-20-methyl-13-prostenoic acid;
13t-4-iodo-14-bromo-5βH-5(9α)-oxide-11α,15S-dihydroxy-20-methyl-13-prostenoic acid;
13t-14-bromo-5βH-5(9α)-oxide-11α,15S-dihydroxy-16(S,R)-fluoro-17-cyclohexyl-18,19,20-trinor-prost-13-enoic acid;
13t-4,14-dibromo-5βH-5(9α)-oxide-11α,15S-dihydroxy-16(S,R)-fluoro-17-cyclohexyl-18,19,20-trinor-prost-13-enoic acid;
13t-4-bromo-5βH-5(9α)-oxide-11α,15S-dihydroxy-16(S,R)-fluoro-17-cyclohexyl-18,19,20-trinor-prost-13-enoic acid;
13t-5βH-5(9α)-oxide-11α,15S-dihydroxy-16(S,R)-fluoro-17-phenyl-18,19,20-trinor-prost-13-enoic acid;
13t-14-bromo-5βH-5(9α)-oxide-11α,15S-dihydroxy-16(S,R)-fluoro-17-phenyl-18,19,20-trinor-prost-13-enoic acid;
13t-5βH-5(9α)-oxide-11α,15S-dihydroxy-17-cyclopentyl-18,19,20-trinor-prost-13-enoic acid;
13t-5βH-5(9α)-oxide-11α,15S-dihydroxy-17-cyclohexyl-18,19,20-trinor-prost-13-enoic acid;
13t-14-bromo-5βH-5(9α)-oxide-11α,15S-hydroxy-17-cyclohexyl-18,19,20-trinor-prost-13-enoic acid;
13t-4,14-dibromo-5βH-5(9α)-oxice-11α,15S-dihydroxy-17-cyclohexyl-18,19,20-trinor-prost-13-enoic acid;
13t-5βH-5(9α)-oxide-11α,15S-dihydroxy-16-phenoxy-17,18,19,20-tetranor-13-prostenoic acid;
13t-4-iodo-5βH-5(9α)-oxide-11α,15S-dihydroxy-16-phenoxy-17,18,19,20-tetranor-13-prostenoic acid;
13t-4-iodo-5βH-5(9α)-oxide-11α,15S-dihydroxy-16-cyclohexyloxy-17,18,19,20-tetranor-13-prostenoic acid;
13t-4-iodo-5βH-5(9α)-oxide-11α,15S-dihydroxy-16-(m-chloro)-phenoxy-17,18,19,20-tetranor-13-prostenoic acid;
13t-4-iodo-5βH-5(9α)-oxide-11α,15S-dihydroxy-16-(m-trifluoromethyl)-phenoxy-17,18,19,20-tetranor-13-prostenoic acid.

In similar way, we prepare the diasteroisomeric αH-9α-oxide-15S- and αH-9α-oxide-15R-alcohols when we use αH-9α-oxide-15-keto diasteroisomer as strting material.

All these esters are then saponified to obtain the free acids.

EXAMPLE 68

0.46 g of 13t-5βH-5(9α)-oxide-16S-methyl-11α-hydroxy-15-oxo-prost-13-enoic acid methyl ester are treated with pyridine (2 ml) and acetic anhydride (1 ml). After 6 hours at room temperature the mixture is diluted with brine, acidified to pH 4.5–4.8 and extracted with ethyl ether. The combined organic phases are then evaporated to dryness yielding 0.48 g of 11-acetoxy-derivative ($\lambda_{max}^{MeOH}=229$ mμ, $\epsilon=11.058$). A solution of this compound in ethyl ether is then added dropwise to a solution of Zn(BH$_4$)$_2$ in ethyl ether. After 30 minutes the excess reagent is decomposed with a N solution of H$_2$SO$_4$ and after the usual worke-up, 0.47 g of 13t-5βH-5(9α)-oxide-16S-methyl-11α,15(S,R)-dihydroxy-13-prostenoic acid methyl ester 11-acetate are obtained. A solution of this mixture in CH$_2$Cl$_2$ (5 ml) cooled to about $-5°$ C., $-10°$ C., is treated with a solution of BF$_3$ etherate ($1.2\times10^{-4}$ M) in CH$_2$Cl$_2$ and then with a 5% solution of diazomethane in CH$_2$Cl$_2$ until a persistent yellow coloration. The reaction mixture is evaporated to half volume under vacuum, washed with a 5% aqueous NaHCO$_3$ solution and water to neutral, and evaporated to dryness to yield 0.47 g of 13t-5βH-5(9α)-oxide-16S-methyl-11α-hydroxy-15(S,R)-methoxy-prost-13-enoic acid-11-acetate which is separated in the individual isomers by chromatography on SiO$_2$ using benzene-ethyl ether (85:15) as eluent. On the other hands, 0.21 g of the mixture of 15(S,R)-methoxy-derivatives is dissolved in dry methanol (4 ml) and selectively deacetilated by treatment with 20 mg of K$_2$CO$_3$ for 4 hours at room temperature. After neutralization by dilution with aqueous NaH$_2$PO$_4$, the methanol evaporated under vacuum and the residue is extracted with ethyl ether (2×5) ethyl acetate (2×6 ml). The combined organic phases are evaporated to dryness to yield 180 mg of the crude 13t-5βH-5(9α)-oxide-16S-methyl-11α-hydroxy-15(S,R)-methoxy-prostenoic acid methyl ester, which is then readily separated by means of a silica gel column chromatography using CH$_2$Cl$_2$-ethyl ether 80:20 as eluent to yield the two pure isomers: 15S-methoxy and 15R-methoxy. Using the same procedure the following methyl esters were obtained:

13t-6βH-6(9α)-oxide-16S-methyl-11α-hydroxy-15S-methoxy-prost-13-enoic acid;
13t-6βH-6(9α)-oxide-16R-methyl-11α-hydroxy-15S-methoxy-prost-13-enoic acid;
13t-6βH-6(9α)-oxide-20-methyl-11α-hydroxy-15S-methoxy-prost-13-enoic acid;
13t-5-bromo-6βH-6(9α)-oxide-20-methyl-11α-hydroxy-15S-methoxy-prost-13-enoic acid;
13t-5-bromo-6βH-6(9α)-oxide-11α-hydroxy-15S-methoxy-prost-13-enoic acid;
13t-5-bromo-6βH-6(9α)-oxide-16S-methyl-11α-hydroxy-15S-methoxy-prost-13-enoic acid, and their epimeric 15R-methoxy compounds are obtained starting from the corresponding 11-acetoxy-15-keto compounds.

Using in this procedure the αH-diastereoisomer instead of the βH, the corresponding αH-15-methoxy compounds are also obtained. The same procedure can be also utilized for any 15-keto compound, previously described and analogously an other diazo alkane can be used inside of diazomethane.

EXAMPLE 69

To a solution of 0.26 g of 13t-6βH-6(9α)-oxide-15(S,R)-hydroxy-16S-methyl-prost-13-enoic acid methyl ester in methylene chloride, treated with 0.3 ml of a solution of BF$_3$ etherate in methylene chloride, cooled at $-10\div-8°$ C., a solution of diazoethane in methylene chloride is added until a persistent yellow coloration is formed. The solvent is evaporated under vacuum and the residue chromatographed on silica gel using ethyl ether-methylene chloride 10:90 as eluent to yield 0.115 g of 13t-6βH-6(9α)-oxide-15S-ethoxy-16S-methyl-prostenoic acid methylester, and 0.1 g of 15R-ethoxy isomer. When a mixture of 15S,15R-alcohols, for example 13t-6βH-6(9α)-oxide-11α,15(S,R)-dihydroxy-16S-methyl-prostenoic acid, containing a free 11-hydroxy group is submitted to the procedure of the examples 68 and 69, the simultaneous alkoxylation of the 11-alcoholic function also accurs yielding with diazomethane for example after chromatographic separation the 13t-6βH-6(9α)-oxide-11α,15S-dimethoxy-16S-methyl-prostenoic acid methyl ester beside the 15R-epimeric derivative.

In a similar way the following 15S-alkoxy prostenoic derivatives were obtained:

13t-5βH-5(9α)-oxide-11α,15S-dimethoxy-prostenoic acid;
13t-6βH-6(9α)-oxide-11α,15S-dimethoxy-prostenoic acid;
13t-6βH-6(9α)-oxide-5-bromo-11α,15S-dimethoxy-prostenoic acid;
13t-6βH-6(9α)-oxide-5-iodo-11α,15S-dimethoxy-prostenoic acid;
13t-5βH-5(9α)-oxide-15S-methoxy-16S-methyl-prostenoic acid;
13t-6βH-6(9α)-oxide-15S-methoxy-16S-methyl-prostenoic acid;
13t-6βH-6(9α)-oxide-15S-methoxy-16R-methyl-prostenoic acid;
13t-6βH-6(9α)-oxide-15S-methoxy-16-methyl-16-butoxy-18, 19,20-trinor-prostenoic acid,
and their 15R epimers are obtained and when they are saponified with LiOH in methanol the free acids are prepared. The same procedure can be used to obtain diastereoisomeric αH-9α-oxide derivatives.

EXAMPLE 70

To a stirred solution of 1.33 g of 13t-6αH-6(9α)-oxide-11α-hydroxy-15-oxo-prost-13-enoic acid methyl ester-11-acetate in 6 ml of toluene and 54 ml of benzene, cooled at +4° C., a solution of 1.67 g of methylmagnesium iodide in ethyl ether is added. After 20 minutes, the excess reagent is decomposed with an iced 20% solution of ammonium chloride in water. After dilution with one volume of ethyl ether the organic phase is washed with water, sodium bicarbonate and water, dried over magnesium sulphate, treated with 0.1 ml of pyridine and evaporated to dryness to yield 1.2 g of 13t-6αH-6(9α)-oxide-11α,15(S,R)-dihydroxy-15-methyl-prostenoic acid-methylester-11-acetate, of which 0.2 g are separated into the pure component by thin layer chromatography on silica gel, with benzene-ether 60:40 eluent. 1 g of the mixture of the two alcohols is dissolved in anhydrous methanol (20 ml) and stirred for 4 hours with 0.25 g of $K_2CO_3$. The mixture is evaporated to dryness, the residue is partitioned between ethyl ether and aqueous 15% $NaH_2PO_4$. The organic phase is evaporated in vacuum and the residue is absorbed on silica gel (200 g). Elution with ethyl ether-isopropylic ether 80:20 affords 0.20 g of 13t-6αH-6(9α)-oxide-11α,15R-dihydroxy-15-methyl-prost-13-enoic acid methyl ester, and 0.36 g of 15S-epimer. 0.16 g of this compound are dissolved in 12 ml of methanol and treated with 0.8 ml of water and 0.2 g of $K_2CO_3$. After 5 hours at room temperature the methanol is evaporated under vacuum, the residue is treated with 20% $NaH_2PO_4$ and ethyl acetate. The organic phase yields 0.14 g of 13t-6αH-6(9α)-oxide-11α,15S-dihydroxy-15-methyl-prost-13-enoic acid. The corresponding 6βH-isomers are prepared in the same way.

EXAMPLE 71

To 1.79 g of 13t-5αH-5(9α)-oxide-11α-hydroxy-15-oxo-prost-13-enoic acid methyl ester-11-acetate in 20 ml of anhydrous tetrahydrofurane, 50 ml of 0.3 M ethynylmagnesium bromide in anhydrous tetrahydrofurane is added. Keep shaking for one hour, eliminate the excess reagent by treating with a saturated $NH_4Cl$ solution, concentrate the organic phase under vacuum, and take up with ethyl ether to yield 1.62 g of 13t-5αH-5(9α)-oxide-11α,15(S,R)-dihydroxy-15-ethynyl-prost-13-enoic acid methyl ester-11-acetate, which is dissolved in anhydrous methanol and treated with 250 mg of anhydrous potassium carbonate for 3 hours under shaking. Evaporated under vacuum and dilute with 20% aqueous $NaH_2PO_4$ and ethyl ether. After evaporating the solvent, the organic phase yields 1.41 g of 13t-5αH-5(9α)-oxide-11α,15(S,R)-dihydroxy-15-ethynyl-prostanoic acid methyl ester, which is separated into the two pure 15S-hydroxy and 15R-hydroxy epimer by silica gel chromatography with benzene-ethyl ether 1:1 as eluent, and after saponification of the 15S-hydroxy-epimer with $K_2CO_3$ in methanol, there is yield of the 13t-5αH-5(9α)-oxide-11α,15S-dihydroxy-15-ethynyl-prostenoic acid.

EXAMPLE 72

To a solution in tetrahydrofuran anhydrous (25 ml) of 1.41 g of 13t-5-bromo-6βH-6(9α)-oxide-15-oxo-prost-13-enoic acid methyl ester, a 0.5 M solution of magnesium vinyl bromide in tetrahydrofurane (25 ml) is added at 0°–5° C. and let stand for 4 hours at room temperature. Decompose the excess reagent with a saturated solution of ammonium chloride, distil the tetrahydrofurane under vacuum and take up with ethyl ether. The organic phase is adsorbed on silica gel and eluted with methylene chloride-ethyl ether to yield 0.41 g of 13t-5-bromo-6βH-6(9α)-oxide-15R-hydroxy-15-vinyl-prostenoic acid methyl ester, and 0.62 g of 15S-isomer, which after saponification with LiOH in methanol yields 0.49 g of pure 13t-5-bromo-6βH-6(9α)-oxide-15S-hydroxy-15-vinyl-prostenoic acid.

EXAMPLE 73

A solution of 0.98 g of 13t-5-bromo-6βH-6(9α)-oxide-11α-hydroxy-15-oxo-20-methyl-prostenoic acid methyl ester-11-acetate in 30 ml of benzene-toluene (85:15) is cooled at 3°–4° C. and to this a solution of 0.92 g of phenylmagnesium bromide in ethyl ether-benzene 1:1 is added. Let stand for 5 hours at room temperature, then decompose the excess reagent with an iced solution of 15% $NH_4Cl$, wash the organic phase repeatedly with water to neutral then evaporate. The crude 15-phenyl-15(S,R)-hydroxy derivative is dissolved in anhydrous methanol to which is 0.25 g of $K_2CO_3$ is added, kept shaking for 2 hours. Evaporate to dryness, dilute with aqueous 20% $NaH_2PO_4$ and ethyl ether, and from the organic phase after evaporation of the solvent, there is a yield of 0.81 g of 13t-5-bromo-6βH-6(8α)-oxide-11α,15(S,R)-dihydroxy-15-phenyl-20-methyl-prostenoic acid methyl ester, which after separation on silica gel with ethyl ether elution yields the individual 15S and 15R isomers.

EXAMPLE 74

By reaction of the corresponding 15-oxo-derivative with a reagent selected from the group of an halogenide of methylmagnesium, ethyl magnesium, vinyl magnesium, ethynyl magnesium and phenyl magnesium, working to one of the procedures given in example 70 to 73, the following methylesters were prepared:
13t-6βH-6(9α)-oxide-15S-hydroxy-15-methyl-prostenoic acid;
13t-6βH-6(9α)-oxide-15S-hydroxy-15,20-dimethyl-prostenoic acid;
13t-6βH-6(9α)-oxide-15S-hydroxy-15-ethyl-prostenoic acid;
13t-6βH-6(9α)-oxide-15S-hydroxy-15-ethynyl-prostenoic acid;

13t-6βH-6(9α)-oxide-11α,15S-dihydroxy-15-methyl-prostenoic acid;
13t-6βH-6(9α)-oxide-11α,15S-dihydroxy-15-ethyl-prostenoic acid;
13t-6βH-6(9α)-oxide-11α,15S-dihydroxy-15-vinyl-prostenoic acid;
13t-6βH-6(9α)-oxide-11α,15S-dihydroxy-15-ethynyl-prostenoic acid;
13t-6βH-6(9α)-oxide-11α,15S-dihydroxy-15-phenyl-prostenoic acid;
13t-6βH-6(9α)-oxide-11α,15S-dihydroxy-15,20-dimethyl-prostenoic acid;
13t-5-bromo-6βH-6(9α)-oxide-11α,15S-dihydroxy-15-methyl-prostenoic acid;
13t-5-bromo-6βH-6(9α)-oxide-11α,15S-dihydroxy-15-vinyl-prostenoic acid;
13t-5-bromo-6βH-6(9α)-oxide-11α,15S-dihydroxy-15-ethynyl-prostenoic acid;
13t-5-bromo-6βH-6(9α)-oxide-11α,15S-dihydroxy-15-ethyl-prostenoic acid;
13t-5-bromo-6βH-6(9α)-oxide-11α,15S-dihydroxy-15-phenyl-prostenoic acid;
13t-4-bromo-5βH-5(9α)-oxide-11α,15S-dihydroxy-15-methyl-prostenoic acid;
13t-4-bromo-5βH-5(9α)-oxide-11α,15S-dihydroxy-15,20-dimethyl-prostenoic acid;
13t-4-bromo-5βH-5(9α)-oxide-11α,15S-dihydroxy-15-ethynyl-prostenoic acid;
13t-5βH-5(9α)-oxide-11α,15S-dihydroxy-15-methyl-prostenoic acid;
13t-5βH-5(9α)-oxide-11α,15S-dihydroxy-15,20-dimethyl-prostenoic acid;
13t-5βH-5(9α)-oxide-11α,15S-dihydroxy-15-phenyl-prostenoic acid;
13t-5βH-5(9α)-oxide-11α,15S-dihydroxy-15-ethynyl-prostenoic acid;
13t-5βH-5(9α)-oxide-11α,15S-dihydroxy-15-vinyl-prostenoic acid;
13t-5βH-5(9α)-oxide-11α,15S-dihydroxy-15-methyl-prostenoic acid,
and their 15R-hydroxy epimers.

Analogously, starting from the αH-(9α)-oxide-15-keto-compounds we obtained the corresponding αH-(9α)-oxide-15-substituted alcohols.

EXAMPLE 75

To a solution of 0.5 g of 13t-6βH-6(9α)-oxide-11α,15S-dihydroxy-14-bromo-16S-methyl-prostenoic acid-methyl ester-11-acetate in 2 ml of dimethylformamide, dimethyl-t-butyl silane chloride (0.21 g) and triethylamine (0.16 g) are added. Keep shaking for 2 hours, then dilute with 4 volumes of water and extract with ethyl ether. The organic phase, after the usual washings, evaporation of the solvent, and filtration through silica gel with cyclohexane-ethyl ether 90:10 eluent, yields 0.57 g of 13t-6βH-6(9α)-oxide 11α,15S-dihydroxy-14-bromo-16S-methyl-prostenoic acid methyl ester-11-acetate-15-dimethyl-t.butylsilylether, from which, by transesterification in anhydrous methanol and 0.5 molar equivalents of K₂CO₃, the corresponding 11-hydroxy-derivative is yielded.

EXAMPLE 76

To 0.52 g of 13t-5,14-dibromo-6βH-6(9α)-oxide-11α,15S-dihydroxy-prostenoic acid methyl ester in 10 ml of dichloromethane, 2,3-dihydro-pyrane (0.27 g) and p-toluenesulphonic acid (4 mg) are added. Keep at room temperature for 3 hours, then wash with a 5% solution of KHCO₃ and water to neutral, and evaporate to dryness. Filter through silica gel with cyclohexane-ethyl ether 90:10 as eluent, which yields 0.59 g of 13t-5,14-dibromo-6βH-(9α)-oxide-11α,15S-dihydroxy-prostenoic acid methyl ester-11,15-bis-tetrahydropyranylether.

EXAMPLE 77

The 14-bromo-alcohols yielded by the foregoing examples, when treated with dimethyl-t.butylchlorosilane in dimethylformamide while, working to the procedures as in example 75, or with an acetalic ether such as 2,3-dihydropyrane-1,4-diox-2-ene, 1-ethoxy-ethylene, and working to the procedure of example 76, are then converted into the corresponding silyloxy or the corresponding acetalic ethers.

EXAMPLE 78

Under an atmosphere of inert gas, to a stirred solution of 0.46 g of 13t-14-bromo-6βH-6(9α)-oxide-15S-methoxy-16S-methyl-prost-13-enoic acid methyl ester in anhydrous dimethylsulfoxide (5 ml), potassium tert-butylate (0.15 g) is added and the stirring is continued for 30 minutes. The reaction mixture is diluted with 2 volumes of water and stirred for 15 minutes, then extracted with ethyl ether. The organic phases are re-extracted with 2×5 ml of 0.2 N NaOH and then with water until neutral and evaporated to dryness to give 30 mg of 6βH-6(9α)-oxide-15S-methoxy-16S-methyl-prost-13-ynoic acid methyl ester. The combined aqueous phase are acidified to pH 5.1 and extracted with ethyl ether. After evaporation of the solvent, 0.28 g of 6βH-6(9α)-oxide-15S-methoxy-16S-methyl-prost-13-ynoic acid is obtained.

EXAMPLE 79

Under an atmosphere of inert gas, with stirring and rigorous exclusion of humidity, 0.84 g of trimethylsilylimidazole is added to an anhydrous dimethylsulfoxide solution of 0.445 g of 13t-5αH-5(9α)-oxide-14-bromo-16R-methyl-prost-13-enoic acid. Stirring is continued for 30 minutes and then a solution of 0.19 g of K-tert-butylate is added. After 30 minutes stirring, the mixture is diluted with 3 volumes of water and stirred for 2 more hours. After acidification to pH 5.2, it is extracted with ethyl ether:hexane 80:20 and the organic extracts are dried and evaporated to dryness to give 0.31 g of 5αH-5(9α)-oxide-16R-methyl-prost-13-ynoic acid.

EXAMPLE 80

To a solution of sodium methylsulfinylcarbanion, obtained by heating at 60° C. for 3 hours and 30 minutes a suspension of 50 mg of 80% NaH in 8 ml of anhydrous dimethylsulfoxide, a solution of 13t-6βH-6(9α)-oxide-11α,15S-dimethoxy-14-bromo-16(S,R)-fluoro-20-methyl-prost-13-enoic acid methyl ester (0.86 g) in 5 ml of dimethyl sulfoxide is added with stirring under an atmosphere of inert gas, at a temperature of 18°–20° C. After 40 minutes of stirring an excess of 25% NaH₂PO₄ is poured in and the mixture extracted with ethyl ether to give 0.51 g of 6βH-6(9α)-oxide-11α,15S-dimethoxy-16(S,R)-fluoro-20-methyl-prost-13-ynoic acid methyl ester.

EXAMPLE 81

To a solution of 80 mg of sodium amide in 10 ml of dimethylsulfoxide a solution of 13t-14-bromo-5αH-

5(9α)-oxide-11α,15S-dihydroxy-16-m-trifluoromethylphenoxy-17,18,19,20-tetranor-prost-13-enoic acid-11,15-bis-tetrahydropyranylether (0.65 g) in 5 ml of dimethylsulfoxide is added. It is stirred for 2 hours and then diluted with water and extracted with ethyl ether. The ether extracts, after reextraction with alkali are discarded. The aqueous alkaline extracts are acidified to pH 4.5 and extracted with ethyl ether to give 0.54 g of 5αH-5(9α)-oxide-11α,15S-dihydroxy-16-m-trifluoromethylphenoxy-17,18,19,20-tetranor-prost-13-ynoic acid-11,15-bis-tetrahydropyranyl ether. A solution of this compound (0.23 g) in anhydrous ethanol (5 ml) and 2,2-diethoxypropane (3 ml) is treated with 20 mg of p-toluenesulfonic acid. After 5 hours at room temperature it is neutralized with aqueous NaHCO$_3$, evaporated under vacuum and the residue partitioned between water and ethyl ether. The organic phase is evaporated and after passing the residue through silica gel 0.1 g of 5α-H-5(9α)-oxide-11α,15S-dihydroxy-16-m-trifluoromethylphenoxy-17,18,19,20-tetranor-prost-13-ynoic acid ethyl ester is obtained. Deacetalization carried out on another 0.2 g of product dissolved in 5 ml of acetone and treated with 3.5 ml of 0.2 N oxalic acid for 8 hours at 40° C., after evaporation of the acetone under vacuum, extraction of the aqueous phase with ethyl ether and chromatography on silica gel with ethyl ether:ethyl acetate 95:5 the free acid (95 mg) is obtained.

In the same way, starting from 13t-14-chloro-6αH-6(9α)-oxide-11α,15S-dihydroxy-17-cyclohexyl-18,19,20-trinor-prost-13-enoic acid-11,15-bis-dioxanylether the 6αH-6(9α)-oxide-11α,15S-dihydroxy-17-cyclohexyl-18,19,20trinor-prost-13-ynoic acid is obtained.

EXAMPLE 82

To a solution of 0.48 g of 13t-14-bromo-6βH-6(9α)-oxide-11α,15S-dihydroxy-16-cyclohexyloxy-17,18,19,20-tetranor-prost-13-enoic acid methyl ester in 3 ml of anhydrous dimethylsulfoxide is added after 30 minutes a solution of 1,5-diazabicyclo[5.4.0]undec-5-ene (0.25 g) in 2 ml of anhydrous dimethylformamide and the reaction mixture maintained for 6 hours at 65° C. It is diluted with water acidified to pH 4.5, extracted with ethyl ether. From the organic phase, after evaporation of the solvent and purification on silica gel (eluted with benzene-ethyl ether 80:20), 6βH-(9α)-oxide-11α,15S-dihydroxy-16-cyclohexyloxy-17,18,19,20-tetranor-prost-13-ynoic acid methyl ester (0.29 g) is obtained.

EXAMPLE 83

Using one of the procedures described in examples 78 to 82 and starting from the corresponding 13t-14-halo-prost-13-enoic acids, the following prost-13-ynoic acids are prepared:

6β-H-6(9α)-oxide-11α,15S-dihydroxy-prost-13-ynoic acid;
6βH-6(9α)-oxide-11α,15R-dihydroxy-prost-13-ynoic acid;
6βH-6(9α)-oxide-15-methoxy-prost-13-ynoic acid;
6βH-6(9α)-oxide-11α,15S-dihydroxy-16S-methyl-prost-13-ynoic acid;
6βH-(9α)-oxide-11α,15S-dihydroxy-16S,20-dimethyl-prost-13-ynoic acid;
6βH-6(9α)-oxide-11α,15S-dihydroxy-16R-methyl-prost-13-ynoic acid;
6βH-6(9α)-oxide-11α,15S-dihydroxy-16S-fluoro-prost-13-ynoic acid;
6βH-6(9α)-oxide-11α,15S-dihydroxy-16,16-difluoro-prost-13-ynoic acid;
6βH-6(9α)-oxide-11α,15S-dihydroxy-20-methyl-prost-13-ynoic acid;
6βH-(9α)-oxide-11α,15S-dihydroxy-17-cyclohexyl-18,19,20-trinor-prost-13-ynoic acid;
6βH-6(9α)-oxide-11α,15S-dihydroxy-16-fluoro-17-cyclohexyl-18,19,20-trinor-prost-13-ynoic acid;
6βH-6(9α)-oxide-11α,15S-dihydroxy-16-p-fluoro-phenoxy-17,18,19,20-tetranor-prost-13-ynoic acid;
6βH-6(9α)-oxide-11α,15S-dihydroxy-17-phenyl-18,19,20-trinor-prost-13-ynoic acid;
5βH-5(9α)-oxide-11α,15S-dihydroxy-16S-methyl-prost-13-ynoic acid;
5βH-5(9α)-oxide-11α,15S-dihydroxy-16S,20-dimethyl-prost-13-ynoic acid;
5βH-5(9α)-oxide-11α,15S-dihydroxy-16R-methyl-prost-13-ynoic acid;
5βH-5(9α)-oxide-11α,15S-dihydroxy-16S-fluoro-prost-13-ynoic acid;
5βH-5(9α)-oxide-11α,15S-dihydroxy-prost-13-ynoic acid;
5βH-5(9α)-oxide-11α,15S-dihydroxy-20-methyl-prost-13-ynoic acid.

Starting from αH-(9α)-oxide compounds and using the same procedure, the epimeric αH-(9α)-oxide-13-ynoic compounds are prepared.

EXAMPLE 84

A solution of 0.35 g of mercuric acetate in methanol is added at room temperature, with stirring, to a solution of 0.54 g of 5c,13t-9α,11α,15S-trihydroxy-prostadienoic acid methyl ester-11,15-bis-THP-ether (PGF$_{2α}$-bis-THP-ether-methyl ester). After stirring for 15 minutes, 50 mg of sodium borohydride is added in small portions, the elemental mercury generated is removed by filtration and the methanol is evaporated under vacuum. The residue is partitioned between dichloromethane/water; the organic phase, after washing with sodium bicarbonate and water until neutral, is evaporated to give 0.51 g of crude 13t-11α,15S-dihydroxy-6βH-6(9α)-oxide-prostenoic acid methyl ester-11,15-bis-THP-ether. A solution of this in 10 ml of acetone added to 8 ml of 0.2 N oxalic acid is heated to 40°-45° C. for 6 hours. After the removal of the acetone under vacuum, the aqueous suspension is extracted with ethyl acetate (3×15 ml). The organic phase is washed until neutral and evaporated to dryness. The residue (approximately 0.45 g) is adsorbed on silica gel (50 g) and eluted with ethyl ether collecting fractions of 20 ml. From fractions 11 to 50, 13t-11α,15S-dihydroxy-6αH-6(9α)-oxide-prostenoic acid methyl ester (0.11 g; m.p. 67°-69° C.) is obtained. Then, after a mixture of diastereoisomers as 5–10% of ethyl acetate is added to ethyl ether, 13t-11α,15S-dihydroxy-6βH-6(9α)-oxide-prostenoic acid methyl ester (0.16 g; $[α]_D= +19.62°$ (CHCl$_3$)) is collected. A sample of the later compound, after crystallization, shows m.p. 40°-41° C., $[α]_D= +25.2°$, $[α]_{365°}= +83.8°$ (CHCl$_3$). The crude free acid has $[α]_D= +18.3°$ (EtOH).

A sample is crystallized from pentane-ethyl ether affording pure crystalline 13t-6βH-6(9α)-oxide-11α,15S-dihydroxy-prost-13-enoic acid, m.p. 80°-81° C., $[α]_D= +32.5°$, $[α]_{365°}= +111.6°$ (EtOH). The mass spectrum of the compound shows the following peaks (m/e, intensity, structure): 336 7% [M—H$_2$O]$^+$, 318 3% [M—2H$_2$O]$^+$; 292 100% [M—H$_2$O-44]$^+$; 264 30%

[M—H$_2$O—CH$_2$CHCO$_2$H]$^+$; 235 4% [M—H$_2$O—(CH$_2$)$_4$CO$_2$H].

The mass spectrum of the 6αH-diastereoisomer is substantially similar.

EXAMPLE 85

A solution of 0.19 g of 5c,13t-9α,11α,15S-trihydroxy-15-methyl-PGF$_{2α}$-methyl ester in 2.5 ml of THF is added to 0.3 g of mercuric acetate in 1.5 ml water/3.0 ml THF. After 30 minutes of stirring, 60 mg of sodium borohydride in 1.2 ml of water is added to the deep yellow suspension. After the mercury is separated, the THF is removed under vacuum and the aqueous suspension is extracted repeatedly with ethyl acetate. The organic phase, when washed until neutral and evaporated to dryness, yields 0.16 g of product which is purified by thin layer chromatography to give 0.04 g of 13t-11α,15S-dihydroxy-6αH-6(9α)-oxide-15-methyl-PGF$_{2α}$-methyl ester, [α]$_D$= +6.2° (CHCl$_3$) and 0.034 g of the 6βH-6(9α)-oxide-isomer, [α]$_D$= +19.62° (CHCl$_3$).

EXAMPLE 86

0.43 g of 5c,13t-9α,15S-dihydroxy-16R-methyl-prostadienoic acid methyl ester-15-dioxanyl ether in methanol (2.5 ml) is reacted with a solution of 0.38 g of mercuric bromide in methanol. The reaction mixture is held at room temperature for 15 minutes and overnight at 0° C. The crystalline precipitate which forms is isolated by filtration to give 0.36 g of 13t-15α-hydroxy-16R-methyl-6ξH-6(9α)-oxide-5-bromomercuric prostenoic acid methyl ester, from which the mercury is removed upon treatment with sodium borohydride to give 0.12 g of 13t-15S-hydroxy-16R-methyl-6ξH-6(9α)-oxide-prostenoic acid methyl ester. Column chromatography on silica gel affects the separation into the 6αH-(9α-oxide and 6βH-6(9α)-oxide diastereoisomers.

EXAMPLE 87

A solution of 0.55 g of 5c-9α,11α,15S-trihydroxy-prostenoic acid methyl ester in 2.5 ml of DME is added to a solution of 0.5 g of mercuric acetate in 2 ml of water/4 ml of DME. After 15 minutes, the reaction mixture is treated with a solution of 0.08 g of sodium borohydride in 1.2 ml of water, the mercury is separated, the DME is removed under vacuum, and the residue is extracted several times with dichloromethane. The organic phase is evaporated to dryness, adsorbed on silica gel and eluted with ethyl ether/ethyl acetate to give 0.21 g of 11α,15S-dihydroxy-6αH-6(9α)-oxide-prostenoic acid methyl ester and 0.18 g of the 6βH-6(9α)oxide isomer.

EXAMPLE 88

A solution of 116 mg of 5c-9α,11α,15S-trihydroxy-17-cyclohexyl-20,19,18-trinor-prost-5-en-13-ynoic acid methyl ester-11,15-bis-THP-ether in 1.5 ml of methanol is treated with 64 mg of mercuric acetate in 1.5 ml of methanol. After 10 minutes, 25 mg of sodium borohydride is added. Methanol is removed under vacuum, the mercury is separated and the product is dissolved in water/ethyl acetate. Evaporation of the organic phase to dryness affords crude 11α,15S-dihydroxy-6ξH-6(9α)-oxide-17-cyclohexyl-20,19,18-trinor-prost-13-ynoic acid methyl ester-11,15-bis-THP-ether (100 mg); this is treated in acetone (4 ml) with 2.5 ml of 0.2 N oxalic acid overnight at 40° C. After removal of the acetone under vaacuum, the mixture is extracted with ethyl acetate. Evaporation of solvent gives a residue which is purified on silica gel (eluent, ethyl ether) to give 28 mg of 11α,15S-dihydroxy-17-cyclohexyl-20,19,18-trinor-6αH-6H-(9α)-oxide-prost-13-ynoic acid methyl ester, [α]$_D$= +17.2°, [α]$_{365°}$= +54°, and 12.5 mg of the 6βH-6(9α)-oxide-isomer, [α]$_D$= +26.5°, [α]$_{365°}$= +84° (EtOH); M$^+$ 406, M—H$_2$O$^+$ 388. Under the same conditions, 5c-9α,11α,15S-trihydroxy-16S-methyl-prost-5-en-13-ynoic acid methyl ester-11,15-bis-THP-ether gives 11α,15S-dihydroxy-16S-methyl-6αH-6(9α)-oxide-prost-13-ynoic acid methyl ester and its 6βH-6(9α)-oxide isomer.

EXAMPLE 89

0.24 g of 13t-11α,15S-dihydroxy-6αH,6(9α)-oxide-16-methyl-16-butoxy-20,19,18-trinor-prostenoic acid methyl ester and 0.13 g of the 6β-H-6(9α)-oxide isomer are obtained from the reaction of 1.01 molar equivalent of mercuric acetate (636 mg) in 10 ml of methanol and 1.1 g of 5c,13t-9α,11α,15S-trihydroxy-16-methyl-16-butoxy-20,19,18-trinor-prostadienoic acid methyl ester-11,15-bis-THP-ether in 5 ml of methanol. The mercury compound so prepared is reduced in situ by the cautious addition of 85 mg of sodium borohydride in small portions. The methanolic solution is then decanted from the solid residue and reduced in volume. 10 ml of 0.2 N aqueous oxalic acid and 20 ml of acetone are added, and the resulting mixture is held at 50° C. for 12 hours. The organic solvents are removed under vacuum, and the resulting solution is saturated with sodium sulfate and extracted with ethyl acetate. The organic phase is washed with 30% ammonium sulfate (2×5 ml) and 2.5 ml of water; after drying over NaSO$_4$, it is evaporated to give a crude residue which is purified on silica gel using an eluent containing an increasing fraction of benzene-methyl acetate, to give the isomeric 6αH-6(9α)-oxide and 6βH-6(9α)-oxide. From the above reaction with 16-m-chloro-phenoxy,16-p-fluorophenoxy, and 16-m-trifluoromethyl-phenoxy-5c,13t-9α,11α,15S-trihydroxy-20,19,18,17-tetranor-prost-5,13-dienoic acid methyl ester-11,15-bis-THP-ether and the analogous 17-phenyl-18,19,20-trinor-derivative were obtained respectively:

13t-11α,15S-dihydroxy-6βH-6(9α)-oxide-17-phenyl-20,19,18-trinor-prostenoic acid methyl ester, [α]$_D$= +28°;

13t-11α,15S-dihydroxy-6βH-6(9α)-oxide-16-m-chlorophenoxy-20,19,18,17-tetranor-prostenoic acid methyl ester, [α]$_D$= +31°;

13t-11α,15S-dihydroxy-6βH-6(9α)-oxide-16-p-fluorophenoxy-20,19,18,17-tetranor-prostenoic acid methyl ester, [α]$_D$= +30° C.;

13t-11α,15S-dihydroxy-6βH-6(9α)-oxide-16-m-trifluoromethylphenoxy-20,19,18,17-tetranor-prostenoic acid methyl ester, [α]$_D$= +33°;

and their 6αH-6(9α)-oxide isomers which show [α]$_D$ ranging between +8° and 12° in CHCl$_3$.

EXAMPLE 90

Using the 16S-fluoro-17-cyclohexyl-5c,13t-9α,1-1α,15S-trihydroxy-20,19,18-trinor-prosta-5,13-dienoic acid methyl ester-11,15-bis-THP-ether, in the procedure of example 89, the 13t-11α,15S-dihydroxy-6αH-6(9α)-oxide-16S-fluoro-17-cyclohexyl-20,19,18-trinor-prost-13-enoic acid-methyl ester and its 6βH-6(9α)-oxide diastereoisomer are obtained.

EXAMPLE 91

0.12 g of 13t-11α,15S-dihydroxy-6βH-6(9α)-oxide-prost-13-enoic acid methyl ester in 6 ml of methanol is reacted with a 0.5 N aqueous solution of lithium hydrate (2 ml). After six hours, the methanol is removed under vacuum. The residue is diluted with water (2 ml) and extracted with ethyl ether to remove neutral impurities. The alkaline aqueous phase is acidified by treatment with 4 ml of 30% aqueous $NaH_2PO_4$ and extracted several times with ethyl ether. The later combined ether extracts are washed with water (2×1 ml) and dried; removal of the solvent affords 91 mg of 13t-11α,15S-dihydroxy-6βH-6(9α)-oxide-prost-13-enoic acid, m.p. 78°-80° C., $[\alpha]_D = +31°$ (EtOH). This procedure is used for saponification of the esters from the preceding examples to the corresponding free acids.

EXAMPLE 92

11α,15S-dihydroxy-6βH-6(9α)-oxide-16S-methyl-prost-13-ynoic acid (0.11 g) in methylene chloride is treated with 1.5 molar equivalent of diazomethane in methylene chloride. After 15 minutes, solvent is removed under vacuum and the residue adsorbed on silica gel. Elution with ethyl ether/benzene (70:30) gives, in the following order, 12 mg of 11α-hydroxy-15S-methoxy-6βH-6(9α)-oxide-16S-methyl-prost-13-ynoic acid methyl ester and 78 mg of 11α,15S-dihydroxy-6βH-6(9α)-oxide-16S-methyl-prost-13-ynoic acid methyl ester. Using in this procedure diazoethane in side of the diazomethane, 11α-hydroxy-15S-ethoxy-6βH-6(9α)-oxide-16S-methyl-prost-13-ynoic acid ethyl ester is obtained.

EXAMPLE 93

A solution of $I_2$ (0.33 g) in methylene chloride is added to a suspension of finely divided calcium carbonate in 6 ml of methylene chloride containing 0.54 g of 5c,13t-9α,11α,15S-trihydroxy-prostadienoic acid methyl ester-11,15-bis-tetrahydropyranyl ether ($PGF_{2\alpha}$-bis-tetrahydropyranyl ether methyl ester). The reaction mixture is cooled in an ice/water bath and kept in darkness. After three hours of stirring, inorganic compounds are removed by filtration and the organic phase is washed with 0.25 N sodium thiosulfate and water. Removal of the solvent affords 0.66 g of crude 13t-5-iodo-6βH-6(9α)-oxide-11α,15S-dihydroxy-prost-13-enoic acid methyl ester-11,15-bis-tetrahydropyranyl ether. A solution of this in 10 ml of acetone is added to 8 ml of 0.1 N oxalic acid and heated to 45°-46° C. for 4 hours. The acetone is then removed at reduced pressure and the aqueous suspension is extracted with ethyl acetate (3×12 ml); the organic phase is washed until neutral and evaporated to dryness. The residue (0.42 g) is separated on silica gel with ethyl ether eluent. Elution of the high $R_f$ fraction with acetone gives 0.14 g of 13t-5-iodo-6αH-6(9α)-oxide-11α,15S-dihydroxy-prost-13-enoic acid methyl ester, while the low $R_f$ portion is 0.20 g of 13t-5-iodo-6βH-6(9α)-oxide-11α,15S-dihydroxy-prost-13-enoic acid methyl ester. The methyl ester of the following acids were prepared analogously:

13t-16S-methyl-5-iodo-6βH-6(9α)-oxide-11α,15S-dihydroxy-prost-13-enoic acid;
13-t-20-methyl-5-iodo-6βH-6(9α)-oxide-11α,15S-dihydroxy-prost-13-enoic acid, $[\alpha]_D = +23°$, $[\alpha]_{365°} = +78°$ ($CHCl_3$);
13t-5-iodo-6βH-6(9α)-oxide-11α,15S-dihydroxy-18,19,20-trinor-17-cyclohexyl-prost-13-enoic acid;
13t-5-iodo-6αH-6(9α)-oxide-11α,15S-dihydroxy-18,19,20-trinor-17-cyclohexyl-prost-13-enoic acid;
13t-5-iodo-6βH-(9α)-oxide-11α,15S-dihydroxy-18,19,20-trinor-17-phenoxy-prost-13-enoic acid;
13t-5-iodo-6αH-6(9α)-oxide-11α,15S-dihydroxy-18,19,20-trinor-17-phenoxy-prost-13-enoic acid;
13t-5-iodo-6βH-6(9α)-oxide-15S-hydroxy-prost-13-enoic acid;
13t-5-iodo-6αH-6(9α)-oxide-15S-hydroxy-prost-13-enoic acid;
13t-5-iodo-6βH-6(9α)-oxide-11α,15S-dihydroxy-prost-13-ynoic acid;
13t-5-iodo-6αH-6(9α)-oxide-11α,15S-dihydroxy-prost-13-ynoic acid;
5-iodo-6βH-6(9α)-oxide-16S-methyl-11α,15S-dihydroxy-prost-13-ynoic acid;
5-iodo-6βH-6(9α)-oxide-20-methyl-11α,15S-dihydroxy-prost-13-ynoic acid, $[\alpha]_D = +20°$ ($CHCl_3$).

EXAMPLE 94

To a solution of 0.22 g of 5c,13t-9α,11α,15S-trihydroxy-15-methyl-$PGF_{2\alpha}$-methyl ester in 10 ml of $CH_2Cl_2$ and 0.1 ml of pyridine is added dropwise a solution of 180 mg of iodine in methylene chloride. The resulting mixture is stirred for 1 hour. After dilution with water and washing of the organic phase with 0.1 N sodium thiosulfate and water until neutral, the solution is evaporated in vacuum to a small volume and adsorbed on a silica gel plate 0.5 mm in thickness. After development with ethyl ether and elution with acetone, 0.052 g of 13t-15-methyl-5-iodo-6βH-6(9α)-oxide-11α,15S-dihydroxy-prost-13-enoic acid methyl ester and 0.021 g of the isomeric 5-iodo-6αH-6(9α)-oxide are obtained.

EXAMPLE 95

0.288 g of 5c-16,16-dimethyl-9α,11α,15S-trihydroxy-prost-5-enoic acid methyl ester in a solution of 60 mg of pyridine in methylene chloride (8 ml) is reacted with 115 ml of bromine in methylene chloride. After 30 minutes, starting material has completely disappeared; the organic phase is washed with water, then 5% aqueous metabisulfite, and then water until neutral to give, after removal of the solvent and purification by TLC on silica gel with ethyl ether as eluent, 0.083 g of 16,16-dimethyl-5-bromo-6βH-6(9α)-oxide-prostanoic acid methyl ester and 0.04 g of 6αH-diacetereoisomer.

The following compounds were prepared analogously:
13t-16,16-dimethyl-5-bromo-6βH-6(9α)-oxide-11α,15S-dihydroxyprost-13-enoic acid;
13t-16,16-dimethyl-5-bromo-6α-H-6(9α)-oxide-11α,15S-dihydroxyprost-13-enoic acid.

EXAMPLE 96

To a solution of hydrotribromide pyrrolidone (1.1 molar equivalents) in anhydrous tetrahydrofuran (6 ml) is added a solution of 5c,13t-9α,11α,15S-trihydroxy-18,19,20-trinor-17-cyclohexyl-prost-5,13-dienoic acid methyl ester-11,15-bis-tetrahydropyranyl ether (0.7 g) in 6 ml of tetrahydrofuran. The mixture is stirred for 12 hours, the precipitate which forms is removed by filtration, and the tetrahydrofuran solution is diluted with 2 volumes of acetone and treated with 4 g of potassium iodide. After 4 hours at room temperature, the iodine liberated is decomposed with sodium metabisulfate. 1.5 volumes of 0.1 N aqueous oxalic acid is then added and the mixture heated to 48° C. for 4 hours. The mixture is reduced under vacuum and extracted with ethyl acetate. Separation on TLC gives 0.14 g of 13t-5-bromo-6αH-6(9α)-oxide-11α,15S-dihydroxy-18,19,20-trinor-17-cyclohexyl-prost-13-enoic acid methyl ester and 0.11 g of the 5-bromo-6βH-6(9α)-oxide. Using the procedures of the examples 95 and 96, the following 6(9α)-oxides were obtained:

5-bromo-6βH-6(9α)-oxide-11α,15S-dihydroxy-18,19,20-trinor-17-cyclohexyl-prost-13-ynoic acid methyl ester;

5-bromo-6βH-6(9α)-oxide-11α,15S-dihydroxy-prostanoic acid;

13t-5-bromo-6βH-6(9α)-oxide-11α,15S-dihydroxy-prost-13-enoic acid;

13t-20-methyl-5-bromo-6βH-6(9α)-oxide-11α,15S-dihydroxy-prost-13-enoic acid;

13t-15-methyl-5-bromo-6βH-6(9α)-oxide-11α,15S-dihydroxy-prost-13-enoic acid;

13t-15-methyl-5-bromo-6αH-6(9α)-oxide-11α,15S-dihydroxy-prost-13-enoic acid;

13t-16S-methyl-5-bromo-6βH-6(9α)-oxide-11α,15S-dihydroxy-prost-13-enoic acid;

13t-5-bromo-6βH-6(9α)-oxide-11α,15S-dihydroxy-18,19,20-trinor-17-cyclohexyl-prost-13-enoic acid;

13t-5-bromo-6βH-6(9α)-oxide-11α,15S-dihydroxy-17,18,19,20-tetranor-16-m-trifluoromethyl-phenoxy-prost-13-enoic acid.

EXAMPLE 97

A solution of $0.1 \times 10^{-3}$ M of a methyl ester, prepared according to examples 93 to 96 in 2 ml of methanol is treated with 1 ml of an aqueous solution of lithium hydrate ($0.2 \times 10^{-3}$ moles). The mixture is stirred for 3 hours, evaporated nearly to dryness, diluted with 5 ml of water, and extracted with ethyl ether.

The organic phase is washed with 0.1 N LiOH (2 N) and water, and is then discarded. The aqueous phase is acidified to pH 4.8 with 30% aqueous $NaH_2PO_4$ and extracted with ethyl ether to give the free acid.

We claim:

1. A compound of formula (I)

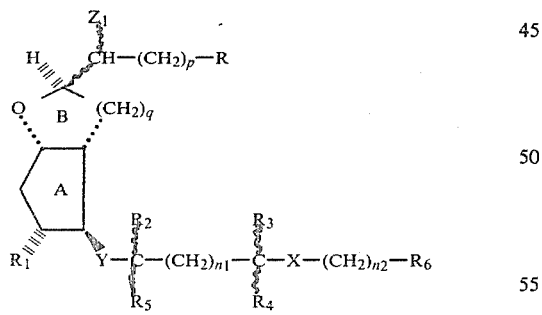

wherein

R is a member selected from the group consisting of
(a) —$COOR_c$ wherein $R_c$ is hydrogen, $C_1$-$C_{12}$ alkyl or $C_2$-$C_{12}$ alkenyl; or
(b)

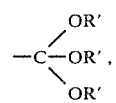

wherein each of the R' groups, which are the same or different, is $C_1$-$C_6$ alkyl or phenyl;

$Z_1$ is hydrogen or halogen;

p is zero or an integer of 1 to 7;

q is 1;

$R_1$ is hydrogen, hydroxy, $C_1$-$C_6$ alkoxy, benzyloxy, $C_2$-$C_{12}$ alkanoyloxy or benzoyloxy;

Y is a member selected from the group consisting of —$CH_2$—$CH_2$—, —C≡C—,

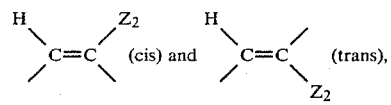

wherein $Z_2$ is hydrogen or halogen;

one of $R_2$ and $R_5$ is hydrogen, $C_1$-$C_6$ alkyl, $C_2$-$C_6$ alkenyl, $C_2$-$C_6$ alkynyl or phenyl, α-naphthyl or β-naphthyl, and the other is hydroxy, $C_1$-$C_6$ alkoxy, benzyloxy, or $R_2$ and $R_5$, taken together, form an oxo group;

each of $R_3$ and $R_4$, which are the same or different, may be hydrogen, $C_1$-$C_6$ alkyl or fluorine or $R_3$ and $R_4$, taken together, with the carbon atom to which they are linked, form the radical

or the radical

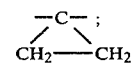

each of $n_1$ and $n_2$, which are the same or different, is zero or an integer of 1 to 6;

X is a member selected from the group consisting of —O—, —S— and —$(CH_2)_m$—, wherein m is zero or 1;

$R_6$ is tetrahydro thienyl or a heterobicyclic ring selected from the group consisting of thiabicyclooctyl and thiabicyclo-nonyl, and the pharmaceutically or veterinarily acceptable salts thereof.

2. A compound of formula (I)

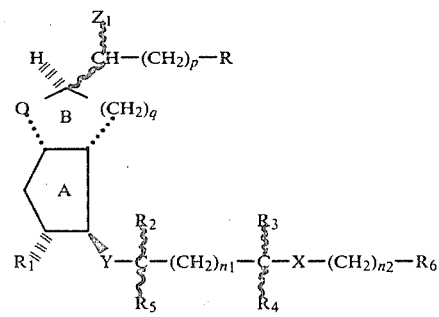

wherein

R is a member selected from the group consisting of
(a) —$COOR_c$ wherein $R_c$ is hydrogen, $C_1$-$C_{12}$ alkyl or $C_2$-$C_{12}$ alkenyl; or
(b)

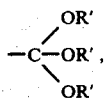

wherein each of the R' groups, which are the same or different, is $C_1$–$C_6$ alkyl or phenyl;

$Z_1$ is hydrogen or halogen;

p is zero or an integer of 1 to 7;

q is 1;

$R_1$ is hydrogen, hydroxy, $C_1$–$C_6$ alkoxy, benzyloxy, $C_2$–$C_{12}$ alkanoyloxy or benzoyloxy;

Y is a member selected from the group consisting of —$CH_2$—$CH_2$—, —C≡C—,

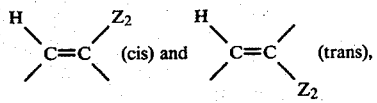

wherein $Z_2$ is hydrogen or halogen;

one of $R_2$ and $R_5$ is hydrogen, $C_1$–$C_6$ alkyl, $C_2$–$C_6$ alkenyl, $C_2$–$C_6$ alkynyl or phenyl, α-naphthyl or β-naphthyl, and the other is hydroxy, $C_1$–$C_6$ alkoxy, benzyloxy, or $R_2$ and $R_5$, taken together, form an oxo group;

each of $R_3$ and $R_4$, which are the same or different, may be hydrogen, $C_1$–$C_6$ alkyl or fluorine or $R_3$ and $R_4$, taken together, with the carbon atom to which they are linked, form the radical

or the radical

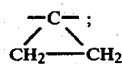

each of $n_1$ and $n_2$, which are the same or different, is zero or an integer of 1 to 6;

X is a member selected from the group consisting of —O—, —S— and —$(CH_2)_m$—, wherein m is zero or 1;

$R_6$ is tetrahydrothienyl or a heterobicyclic ring selected from the group consisting of 2-thiabicyclo[3.3.0]octyl, 2-thia-bicyclo[3.4.0]nonyl and their aromatic analogs, and the pharmaceutically or veterinarily acceptable salts thereof.

3. The compound of any of claims 1 or 2 wherein R is a free or salified carboxy group.

4. The compound of any of claims 1 or 2 wherein R is an esterified carboxy group of formula —$COOR_c$ wherein $R_c$ is $C_1$–$C_{12}$ alkyl or $C_2$–$C_{12}$ alkenyl.

5. The compound of any of claims 1 or 2 wherein p is an integer of 1 to 3.

6. The compound of any of claims 1 or 2 wherein $R_1$ is hydrogen or hydroxy.

7. The compound of any of claim 1 or 2 wherein $R_3$ and $R_4$ are independently selected from the group consisting of hydrogen, $C_1$–$C_6$ alkyl and fluorine.

8. The compound of any of claims 1 or 2 wherein $n_1$ is zero or an integer of 1 to 3.

9. The compound of any of claims 1 or 2 wherein $n_2$ is an integer of 1 to 3.

10. The compound 13t-6β-H-6,9α-oxide-11α,15S-dihydroxy-17-(2'-tetrahydrothienyl)-20,19,18-trinor-prost-13-enoic acid and the pharmaceutically or veterinarily acceptable salts thereof.

11. A pharmaceutical or veterinary composition, suitable for use as a hypotensive agent, said composition comprising a therapeutically effective amount of a compound as claimed in any of claims 1 to 10, and a pharmaceutically and/or veterinarily acceptable carrier and/or diluent.

12. A pharmaceutical or veterinary composition, suitable for use as a vasodilatory agent, said composition comprising a therapeutically effective amount of a compound as claimed in any of claims 1 to 10, and a pharmaceutically and/or veterinarily acceptable carrier and/or diluent.

13. A pharmaceutical or veterinary composition, suitable for use as an anti-aggregating agent, said composition comprising a therapeutically effective amount of a compound as claimed in any of claims 1 to 10, and a pharmaceutically and/or veterinarily acceptable carrier and/or diluent.

14. A pharmaceutical or veterinary composition, suitable for use as an anti-thrombotic agent, said composition comprising a therapeutically effective amount of a compound as claimed in any of claims 1 to 10, and a pharmaceutically and/or veterinarily acceptable carrier and/or diluent.

15. A pharmaceutical or veterinary composition, suitable for use as a luteolytic agent, said composition comprising a therapeutically effective amount of a compound as claimed in any of claims 1 to 10, and a pharmaceutically and/or veterinarily acceptable carrier and/or diluent.

16. A pharmaceutical or veterinary composition, suitable for use as a cytoprotective agent active on the mucous membranes of the gastrointestinal tract, said composition comprising a therapeutically effective amount of a compound as claimed in any of claims 1 to 10, and a pharmaceutically and/or veterinarily acceptable carrier and/or diluent.

17. A pharmaceutical or veterinary composition, suitable for use as an anti-secretory agent, said composition comprising a therapeutically effective amount of a compound as claimed in any of claims 1 to 10, and a pharmaceutically and/or veterinarily acceptable carrier and/or diluent.

18. A pharmaceutical or veterinary composition, suitable for use as a bronchodilatory agent, said composition comprising a therapeutically effective amount of a compound as claimed in any of claims 1 to 10, and a pharmaceutically and/or veterinarily acceptable carrier and/or diluent.

19. A pharmaceutical or veterinary composition, suitable for use as an anti-asthmatic agent, said composition comprising a therapeutically effective amount of a compound as claimed in any of claims 1 to 10, and a pharmaceutically and/or veterinarily acceptable carrier and/or diluent.

20. A pharmaceutical or veterinary composition, suitable for use as an uterus stimulant, said composition comprising a therapeutically effective amount of a compound as claimed in any of claims 1 to 10, and a pharmaceutically and/or veterinarily acceptable carrier and/or diluent.

* * * * *